US011891603B2

(12) United States Patent
Yokota et al.

(10) Patent No.: US 11,891,603 B2
(45) Date of Patent: *Feb. 6, 2024

(54) ANTISENSE OLIGONUCLEOTIDES THAT BIND TO EXON 51 OF HUMAN DYSTROPHIN PRE-MRNA

(71) Applicant: The Governors of the University of Alberta, Edmonton (CA)

(72) Inventors: Toshifumi Yokota, Edmonton (CA); Yusuke Echigoya, Kanagawa (JP)

(73) Assignee: THE GOVERNORS OF THE UNIVERSITY OF ALBERTA, Alberta (CA)

( * ) Notice: Subject to any disclaimer, the term of this patent is extended or adjusted under 35 U.S.C. 154(b) by 77 days.

This patent is subject to a terminal disclaimer.

(21) Appl. No.: 17/466,833

(22) Filed: Sep. 3, 2021

(65) Prior Publication Data
US 2021/0395741 A1    Dec. 23, 2021

Related U.S. Application Data

(63) Continuation of application No. 16/632,827, filed as application No. PCT/CA2018/050881 on Jul. 20, 2018, now Pat. No. 11,142,767.

(30) Foreign Application Priority Data

Jul. 21, 2017 (GB) ..................... 1711809

(51) Int. Cl.
C07H 21/04 (2006.01)
C12N 15/113 (2010.01)
A61P 21/00 (2006.01)

(52) U.S. Cl.
CPC ............ *C12N 15/113* (2013.01); *A61P 21/00* (2018.01); *C12N 2310/11* (2013.01); *C12N 2310/3513* (2013.01); *C12N 2320/33* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,694,778 A | 9/1987 | Learn et al. |
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,334,711 A | 8/1994 | Sproat et al. |
| 5,506,337 A | 4/1996 | Summerton et al. |
| 5,521,063 A | 5/1996 | Summerton et al. |
| 5,627,053 A | 5/1997 | Usman et al. |
| 5,698,685 A | 12/1997 | Summerton et al. |
| 5,716,824 A | 2/1998 | Beigelman et al. |
| 5,736,557 A | 4/1998 | Hofheinz et al. |
| 5,889,136 A | 3/1999 | Scaringe et al. |
| 6,008,400 A | 12/1999 | Scaringe et al. |
| 6,111,086 A | 8/2000 | Scaringe |
| 6,194,551 B1 | 2/2001 | Idusogie et al. |
| 6,528,624 B1 | 3/2003 | Idusogie et al. |
| 6,538,124 B1 | 3/2003 | Idusogie et al. |
| 6,821,783 B1 | 11/2004 | Comely et al. |
| 6,884,869 B2 | 4/2005 | Senter et al. |
| 7,364,731 B2 | 4/2008 | Idusogie et al. |
| 7,452,987 B2 | 11/2008 | Giese et al. |
| 7,498,258 B2 | 3/2009 | Hiatt |
| 7,498,298 B2 | 3/2009 | Doronina et al. |
| 7,736,647 B2 | 6/2010 | Boumsell et al. |
| 7,791,195 B2 | 9/2010 | Kim |
| 7,833,992 B2 | 11/2010 | Vargeese et al. |
| 7,850,975 B2 | 12/2010 | Mullis |
| 7,893,245 B2 | 2/2011 | Giese et al. |
| 7,923,547 B2 | 4/2011 | Mcswiggen et al. |
| 7,943,762 B2 | 5/2011 | Weller et al. |
| 8,084,582 B2 | 12/2011 | Dahiyat et al. |
| 8,084,598 B1 | 12/2011 | Bentwich |
| 8,090,542 B2 | 1/2012 | Khvorova et al. |
| 8,202,979 B2 | 6/2012 | Mcswiggen et al. |
| 8,248,352 B2 | 8/2012 | Kim et al. |
| 8,273,866 B2 | 9/2012 | Mcswiggen et al. |
| 8,288,352 B2 | 10/2012 | Doronina et al. |
| 8,324,370 B2 | 12/2012 | Giese et al. |
| 8,324,371 B2 | 12/2012 | Popplewell et al. |
| 8,361,979 B2 | 1/2013 | Aartsma-Rus et al. |

(Continued)

FOREIGN PATENT DOCUMENTS

| | | |
|---|---|---|
| AU | 2013204438 A1 | 5/2013 |
| CN | 102625840 A | 8/2012 |

(Continued)

OTHER PUBLICATIONS

El-Sayed et al. ("Delivery of macromolecules using arginine-rich cell-penetrating peptides: ways to overcome endosomal entrapment." The AAPS journal 11.1 (2009): 13-22).*
Aartsma-Rus et al. Guidelines for antisense oligonucleotide design and insight into splice-modulating mechanisms. Mol Ther 17(3):548-53 (2009).
Aartsma-Rus et al. Targeted exon skipping as a potential gene correction therapy for Duchenne muscular dystrophy. Neuromuscul Disord. 12 Suppl 1:S71-7 (2002).
Abramova et al. Novel oligonucleotide analogues based on morpholino nucleoside subunits-antisense technologies: new chemical possibilities. Indian Journal of Chemistry 48B:1721-1726 (2009).

(Continued)

*Primary Examiner* — Kimberly Chong
(74) *Attorney, Agent, or Firm* — WILSON SONSINI GOODRICH & ROSATI

(57) ABSTRACT

The present invention relates to a therapeutic antisense oligonucleotide which binds to exon 51 of the human dystrophin pre-mRNA to induce exon skipping, and conjugates and compositions thereof for the treatment of DMD.

10 Claims, 8 Drawing Sheets
Specification includes a Sequence Listing.

(56) References Cited

U.S. PATENT DOCUMENTS

| | | | |
|---|---|---|---|
| 8,461,325 B2 | 6/2013 | Popplewell et al. | |
| 8,501,703 B2 | 8/2013 | Bennett et al. | |
| 8,501,930 B2 | 8/2013 | Rozema et al. | |
| 8,591,910 B2 | 11/2013 | Mullis | |
| 8,604,184 B2 | 12/2013 | Mullis et al. | |
| 8,609,105 B2 | 12/2013 | Senter et al. | |
| 8,618,277 B2 | 12/2013 | Beigelman et al. | |
| 8,637,483 B2 * | 1/2014 | Wilton | C12N 15/113 536/24.5 |
| 8,648,185 B2 | 2/2014 | Mcswigen et al. | |
| 8,697,688 B2 | 4/2014 | Howard et al. | |
| 8,835,402 B2 | 9/2014 | Kole et al. | |
| 8,865,883 B2 * | 10/2014 | Sazani | C12N 15/111 435/375 |
| 8,895,722 B2 | 11/2014 | Iversen et al. | |
| 8,933,215 B2 | 1/2015 | Giese et al. | |
| 8,936,910 B2 | 1/2015 | Mitsch et al. | |
| 8,969,526 B2 | 3/2015 | Baehner et al. | |
| 9,078,911 B2 | 7/2015 | Lu | |
| 9,089,614 B2 | 7/2015 | Lin et al. | |
| 9,096,877 B2 | 8/2015 | Johnson et al. | |
| 9,139,828 B2 | 9/2015 | Platenburg et al. | |
| 9,175,286 B2 | 11/2015 | Wilton et al. | |
| 9,181,551 B2 | 11/2015 | Mcswiggen et al. | |
| 9,222,092 B2 | 12/2015 | Giese et al. | |
| 9,228,187 B2 | 1/2016 | Wilton et al. | |
| 9,243,251 B2 | 1/2016 | Popplewell et al. | |
| 9,243,252 B2 | 1/2016 | Popplewell et al. | |
| 9,249,416 B2 | 2/2016 | Wilton et al. | |
| 9,260,471 B2 | 2/2016 | Cancilla et al. | |
| 9,416,361 B2 | 8/2016 | Iversen et al. | |
| 9,434,948 B2 | 9/2016 | Sazani et al. | |
| 9,441,229 B2 | 9/2016 | Wilton et al. | |
| 9,447,415 B2 | 9/2016 | Wilton et al. | |
| 9,447,417 B2 | 9/2016 | Sazani et al. | |
| 9,481,905 B2 | 11/2016 | Chen et al. | |
| 9,499,818 B2 | 11/2016 | Van Deutekom | |
| 9,528,109 B2 | 12/2016 | De Kimpe et al. | |
| 9,598,496 B2 | 3/2017 | Kurosawa et al. | |
| 9,605,019 B2 | 3/2017 | Verdine et al. | |
| 9,657,294 B2 | 5/2017 | Beigelman et al. | |
| 9,695,211 B2 | 7/2017 | Wada et al. | |
| 9,695,423 B2 | 7/2017 | Giese et al. | |
| 9,732,344 B2 | 8/2017 | Beigelman et al. | |
| 9,765,338 B2 | 9/2017 | Bennett et al. | |
| 9,771,588 B2 | 9/2017 | Mcswiggen et al. | |
| 9,796,974 B2 | 10/2017 | Rajeev et al. | |
| 9,890,379 B2 | 2/2018 | De Kimpe et al. | |
| 9,926,557 B2 | 3/2018 | De Kimpe et al. | |
| 9,982,257 B2 | 5/2018 | Butler et al. | |
| 10,000,754 B2 | 6/2018 | Beigelman et al. | |
| 10,704,060 B2 | 7/2020 | Gersbach et al. | |
| 11,142,767 B2 | 10/2021 | Yokota et al. | |
| 11,179,472 B2 | 11/2021 | Levin et al. | |
| 11,311,627 B1 | 4/2022 | Levin et al. | |
| 11,400,163 B2 | 8/2022 | Levin et al. | |
| 2002/0142980 A1 | 10/2002 | Thompson et al. | |
| 2008/0311557 A1 | 12/2008 | Elsemore et al. | |
| 2009/0092985 A1 | 4/2009 | Cardozo et al. | |
| 2011/0081362 A1 | 4/2011 | Elledge et al. | |
| 2011/0263686 A1 | 10/2011 | Wilton et al. | |
| 2011/0294753 A1 | 12/2011 | De Kimpe et al. | |
| 2011/0301218 A1 | 12/2011 | Bozzoni et al. | |
| 2012/0065169 A1 | 3/2012 | Hanson et al. | |
| 2012/0094299 A1 | 4/2012 | Ranum et al. | |
| 2012/0172415 A1 | 7/2012 | Voit et al. | |
| 2012/0270925 A1 | 10/2012 | Wilton et al. | |
| 2012/0289457 A1 | 11/2012 | Hanson | |
| 2013/0024919 A1 | 1/2013 | Wetter et al. | |
| 2013/0028919 A1 | 1/2013 | Howard et al. | |
| 2013/0172238 A1 | 7/2013 | Mitsch et al. | |
| 2013/0309256 A1 | 11/2013 | Lyon et al. | |
| 2014/0127239 A1 | 5/2014 | Howard | |
| 2014/0194610 A1 | 7/2014 | Verdine et al. | |
| 2014/0246970 A1 | 9/2014 | Park et al. | |
| 2014/0254851 A1 | 9/2014 | Chen | |
| 2014/0286970 A1 | 9/2014 | Jeffrey et al. | |
| 2014/0294851 A1 | 10/2014 | Nguyen | |
| 2014/0296321 A1 | 10/2014 | Iversen | |
| 2014/0315862 A1 | 10/2014 | Kaye | |
| 2015/0037360 A1 | 2/2015 | Smith | |
| 2015/0105539 A1 | 4/2015 | Miao et al. | |
| 2015/0105540 A1 | 4/2015 | Miao et al. | |
| 2015/0110791 A1 | 4/2015 | Zhang et al. | |
| 2015/0211006 A1 | 7/2015 | Butler et al. | |
| 2015/0361428 A1 * | 12/2015 | Bestwick | A61P 21/04 435/320.1 |
| 2016/0002637 A1 | 1/2016 | Sazani et al. | |
| 2016/0053262 A1 | 2/2016 | Platenburg et al. | |
| 2016/0102135 A1 | 4/2016 | Escobar-Cabrera | |
| 2016/0193355 A1 | 7/2016 | Qin et al. | |
| 2016/0201089 A1 | 7/2016 | Gersbach et al. | |
| 2016/0237426 A1 | 8/2016 | Hanson | |
| 2016/0298111 A1 | 10/2016 | Bestwick et al. | |
| 2016/0304864 A1 | 10/2016 | De Kimpe et al. | |
| 2016/0304877 A1 | 10/2016 | Swayze et al. | |
| 2016/0367687 A1 | 12/2016 | Manoharan et al. | |
| 2017/0067048 A1 | 3/2017 | Wakayama et al. | |
| 2017/0107512 A1 | 4/2017 | De Kimpe et al. | |
| 2017/0204410 A1 | 7/2017 | Watanabe et al. | |
| 2017/0204414 A1 | 7/2017 | Van Deutekom et al. | |
| 2017/0281795 A1 | 10/2017 | Geall et al. | |
| 2017/0342416 A1 | 11/2017 | Mcswiggen et al. | |
| 2018/0016574 A1 | 1/2018 | Bestwick et al. | |
| 2018/0044675 A1 | 2/2018 | Watanabe et al. | |
| 2018/0112214 A1 | 4/2018 | De Kimpe et al. | |
| 2018/0127758 A1 | 5/2018 | Bennett | |
| 2018/0163209 A1 | 6/2018 | Bennett et al. | |
| 2018/0305689 A1 | 10/2018 | Sætrom et al. | |
| 2018/0369400 A1 | 12/2018 | Levin et al. | |
| 2019/0240346 A1 | 8/2019 | Sugo et al. | |
| 2020/0282074 A1 | 9/2020 | Levin et al. | |
| 2022/0096647 A1 | 3/2022 | Geall et al. | |
| 2022/0235354 A1 | 7/2022 | Darimont et al. | |
| 2022/0313833 A1 | 10/2022 | Levin et al. | |

FOREIGN PATENT DOCUMENTS

| | | |
|---|---|---|
| CN | 103003430 A | 3/2013 |
| CN | 106459955 A | 2/2017 |
| EP | 0336675 A1 | 10/1989 |
| EP | 0334656 B1 | 3/1994 |
| EP | 1579015 A2 | 9/2005 |
| EP | 1068241 B1 | 10/2007 |
| EP | 2119783 A1 | 11/2009 |
| EP | 2049664 B1 | 9/2011 |
| EP | 2386636 A2 | 11/2011 |
| EP | 2278004 B1 | 10/2012 |
| EP | 2602322 A1 | 6/2013 |
| EP | 2796425 A1 | 10/2014 |
| EP | 2344637 B1 | 12/2014 |
| EP | 1423406 B2 | 11/2015 |
| EP | 3031920 A1 | 6/2016 |
| EP | 2421971 B1 | 7/2016 |
| EP | 2287306 B2 | 10/2016 |
| EP | 3118311 A1 | 1/2017 |
| EP | 3030658 A4 | 3/2017 |
| EP | 2287305 B2 | 11/2017 |
| EP | 2486141 B1 | 1/2018 |
| EP | 2902406 B1 | 1/2018 |
| EP | 2595664 B1 | 10/2018 |
| WO | WO-9104753 A1 | 4/1991 |
| WO | WO-9207065 A1 | 4/1992 |
| WO | WO-9315187 A1 | 8/1993 |
| WO | WO-9726270 A2 | 7/1997 |
| WO | WO-9734631 A1 | 9/1997 |
| WO | WO-9813526 A1 | 4/1998 |
| WO | WO-0149698 A1 | 7/2001 |
| WO | WO-03071872 A1 | 9/2003 |
| WO | WO-2004009851 A2 | 1/2004 |
| WO | WO-2004083446 A2 | 9/2004 |
| WO | WO-2006000057 A1 | 1/2006 |
| WO | WO-2006021724 A2 | 3/2006 |
| WO | WO-2006112705 A2 | 10/2006 |

(56) References Cited

FOREIGN PATENT DOCUMENTS

| | | |
|---|---|---|
| WO | WO-2008036127 A2 | 3/2008 |
| WO | WO-2009005793 A2 | 1/2009 |
| WO | WO-2009026933 A1 | 3/2009 |
| WO | WO-2009054725 A2 | 4/2009 |
| WO | WO-2009099942 A2 | 8/2009 |
| WO | WO-2009099991 A2 | 8/2009 |
| WO | WO-2009144481 A2 | 12/2009 |
| WO | WO-2009147368 A1 | 12/2009 |
| WO | WO-2010048586 A1 | 4/2010 |
| WO | WO-2010050801 A1 | 5/2010 |
| WO | WO-2010050802 A2 | 5/2010 |
| WO | WO-2011057350 A1 | 5/2011 |
| WO | WO-2011078797 A2 | 6/2011 |
| WO | WO-2011150408 A2 | 12/2011 |
| WO | WO-2012109296 A1 | 8/2012 |
| WO | WO-2012138487 A2 | 10/2012 |
| WO | WO-2013030569 A2 | 3/2013 |
| WO | WO-2013112053 A1 | 8/2013 |
| WO | WO-2013166155 A1 | 11/2013 |
| WO | WO-2014007620 A2 | 1/2014 |
| WO | WO-2014080251 A1 | 5/2014 |
| WO | WO-2014140277 A1 | 9/2014 |
| WO | WO-2014140317 A2 | 9/2014 |
| WO | WO-2014145090 A1 | 9/2014 |
| WO | WO-2014177042 A1 | 11/2014 |
| WO | WO-2014197748 A2 | 12/2014 |
| WO | WO-2014197854 A1 | 12/2014 |
| WO | WO-2015021457 A2 | 2/2015 |
| WO | WO-2015038426 A1 | 3/2015 |
| WO | WO-2015048792 A1 | 4/2015 |
| WO | WO-2015057699 A2 | 4/2015 |
| WO | WO-2015069587 A2 | 5/2015 |
| WO | WO-2015075747 A1 | 5/2015 |
| WO | WO-2015107425 A2 | 7/2015 |
| WO | WO-2016187425 A1 | 11/2016 |
| WO | WO-2016207240 A1 | 12/2016 |
| WO | WO-2017059131 A1 | 4/2017 |
| WO | WO-2017109494 A1 | 6/2017 |
| WO | WO-2017148879 A1 | 9/2017 |
| WO | WO-2017173408 A1 | 10/2017 |
| WO | WO-2017192679 A1 | 11/2017 |
| WO | WO-2017221883 A1 | 12/2017 |
| WO | WO-2018002812 A1 | 1/2018 |
| WO | WO-2018118599 A1 | 6/2018 |
| WO | WO-2018129384 A1 | 7/2018 |
| WO | WO-2019014772 A1 | 1/2019 |
| WO | WO-2019060775 A1 | 3/2019 |
| WO | WO-2020132584 A1 | 6/2020 |
| WO | WO-2020219820 A1 | 10/2020 |
| WO | WO-2021003573 A1 | 1/2021 |

OTHER PUBLICATIONS

Agarwal et al. A Pictet-Spengler ligation for protein chemical modification. PNAS 110(1):46-51 (2013).
Albarran et al. Efficient intracellular delivery of a pro-apoptotic peptide with a pH-responsive carrier. React Funct Polym 71:261-265 (2011).
Arechavala-Gomeza et al. Comparative analysis of antisense oligonucleotide sequences for targeted skipping of exon 51 during dystrophin pre-mRNA splicing in human muscle. Hum Gene Ther. 18(9):798-810 (2007).
Axup et al. Synthesis of site-specific antibody-drug conjugates using unnatural amino acids. PNAS 109(40):16101-16106 (2012).
Baumer et al. Antibody-mediated delivery of anti-KRAS-siRNA in vivo overcomes therapy resistance in colon cancer. Clin Can Res 21(6):1383-1394 (2015).
Beduneau et al. Design of targeted lipid nanocapsules by conjugation of whole antibodies and antibody Fab' fragments. Biomaterials 28(33):4978-4990 (2007).
Beigelman et al. Chemical modification of hammerhead ribozymes. Catalytic activity and nuclease resistance. J Biol Chem 270:25702-25708 (1995).
Bell et al. Epidermal Growth Factor Receptor Mutations and Gene Amplification in Non-Small-Cell Lung Cancer: Molecular Analysis of the IDEAL/INTACT Gefitinib Trials. J Clin Oncol 23(31):8081-8092 (2005).
Bird et al. Single-chain antigen-binding proteins. Science 242:423-442 (1988).
Blaney et al. Traceless solid-phase organic synthesis. Chem. Rev. 102:2607-2024 (2002.
Brown et al. Dystrophic phenotype induced in vitro by antibody blockade of muscle alpha-dystroglycan-laminin interaction. J Cell Sci 112:209-216 (1999).
Bulmus et al. A new pH-responsive and glutathione-reactive, endosomal membrane-disruptive polymeric carrier for intracellular delivery of biomolecular drugs. J Controlled Release 93:105-120 (2003).
Burke et al. siRNA-mediated knockdown of P450 oxidoreductase in rats: a tool to reduce metabolism by CYPs and increase exposure of high clearance compounds. Pharm. Res. 31(12):3445-3460 (2014).
Burlina et al. Chemical engineering of RNase resistant and catalytically active hammerhead ribozymes. Bioorg Med Chem 5:1999-2010 (1997).
Casi et al. Site-specific traceless coupling of potent cytotoxic drugs to recombinant antibodies for pharmacodelivery. J Am Chem Soc 134(13):5887-5892 (2012).
Castaneda et al. Acid-cleavable thiomaleamic acid linker for homogeneous antibody-drug conjugation, Chem. Commun. 49:8187-8189 (2013).
Chen et al. Strand-specific 5'-O-methylation of siRNA duplexes controls guide strand selection and targeting specificity. RNA 14:263-274 (2008).
Clackson et al. Making antibody fragments using phage display libraries. Nature 352(6336):624-628 (1991).
Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Collins et al. Duchenne's muscular dystrophy: animal models used to investigate pathogenesis and develop therapeutic strategies. Int J Exp Pathol 84:165-172 (2003).
Crouse et al. Expression and amplification of engineered mouse dihydrofolate reductase minigenes. Mol Cell Biol 3(2):257-266 (1983).
Cuellar et al. Systematic evaluation of antibody-mediated siRNA delivery using an industrial platform of THIOMAB-siRNA conjugates. Nucleic Acids Res 43(2):1189-1203 (2015).
Dawson et al. Modulation of Reactivity in Native Chemical Ligation through the Use of Thiol Additives. J. Am. Chem. Soc. 119:4325-4329 (1997).
Dawson et al. Synthesis of proteins by native chemical ligation. Science 266(5186):776-779 (1994).
De Angelis et al. Chimeric snRNA molecules carrying antisense sequences against the splice junctions of exon 51 of the dystrophin pre-mRNA induce exon skipping and restoration of a dystrophin synthesis in Delta 48-50 DMD cells. PNAS USA 99:9456-9461 (2002).
Debinski et al. Monovalent immunotoxin containing truncated form of Pseudomonas exotoxin as potent antitumor agent. Cancer Research 52(19):5379-5385 (1992).
Deleavey et al. Designing chemically modified oligonucleotides for targeted gene silencing. Chem Biol. 19(8):937-954 (2012).
Dietel et al. A 2015 update on predictive molecular pathology and its role in targeted cancer therapy: a review focussing on clinical relevance. Cancer Gene Ther 22(9):417-430 (2015).
Dimasi et al. Development of a trispecific antibody designed to simultaneously and efficiently target three different antigens on tumor cells. Mol Pharm 12(9):3490-3501 (2015).
Domingo et al. Transferrin receptor as a target for antibody—drug conjugates. Methods in Enzymology 112:238-247 (1985).
Duncan et al. A polymer-Triton X-100 conjugate capable of pH-dependent red blood cell lysis: a model system illustrating the

(56) References Cited

OTHER PUBLICATIONS possibility of drug delivery within acidic intracellular compartments. J Drug Target 2:341-347 (1994).
Earnshaw et al. Modified oligoribonucleotides as site-specific probes of RNA structure and function. Biopolymers (Nucleic Acid Sciences) 48:39-55 (1998).
Echigoya et al. In Silico Screening Based on Predictive Algorithms as a Design Tool for Exon Skipping Oligonucleotides in Duchenne Muscular Dystrophy. PLoS One 10(3):e0120058 (2015).
El-Sayed et al. Delivery of macromolecules using arginine-rich cell-penetrating peptides: ways to overcome endosomal entrapment. The AAPS journal 11(1):13-22 (2009).
El-Sayed et al. Rational design of composition and activity correlations for pH-responsive and glutathione-reactive polymer therapeutics. J Control Release 104:417-427 (2005).
Feener et al. Alternative splicing of human dystrophin mRNA generates isoforms at the carboxy terminus. Nature 338:509-511 (Apr. 6, 1989).
Flanary et al. Antigen delivery with poly(propylacrylic acid) conjugation enhanced MHC-1 presentation and T-cell activation. Bioconjugate Chem. 20:241-248 (2009).
Gao et al. Effective Dystrophin Restoration by a Novel Muscle-Homing Peptide—Morpholino Conjugate in Dystrophin-Deficient mdx Mice. Mol Ther. 22(7):1333-1341 (2014).
Gaziova et al. Chemically defined polyethylene glycol siRNA conjugates with enhanced gene silencing effect. Bioorg Med Chem 22(7):2320-2326 (2014).
Goldspiel et al. Human gene therapy. Clin Pharm 12:488-505 (1993).
Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).
Hackeng et al. Protein synthesis by native chemical ligation: Expanded scope by using straightforward methodology. PNAS USA 96:10068-10073 (1999).
Hanes et al. In vitro selection and evolution of functional proteins by using ribosome display. PNAS USA 94:4937-4942 (1997).
Hayash et al. Skin-specific in vivo gene and oligonucleotides transfer into fetal rats as novel model of tissue-specific overexpression of transgene or knock-out by antisense oligonucleotides. Gene Therapy 3:878-885 (1996).
Hejesen et al. A traceless aryl-triazene linker for DNA-directed chemistry. Org Biomol Chem 11(15):2493-2497 (2013).
Henry et al. pH-responsive poly(styrene-alt-maleic anhydride) alkylamide copolymers for intracellular drug delivery. Biomacromolecules 7:2407-2414 (2006).
Hitachi et al. Role of microRNAs in skeletal muscle hypertrophy. Front Physiol 16(4):408 (2014).
Hoffman et al. Restoring Dystrophin Expression in Duchenne Muscular Dystrophy Muscle: Progress in Exon Skipping and Stop Codon Read Through. Am J Pathol 179(1):12-22 (2011).
Hu et al. Site-specific Antibody-polymer Conjugates for siRNA Delivery. J Am Chem Soc 135(37):13885-13891 (2013).
Huang et al. Mechanisms of resistance to EGFR tyrosine kinase inhibitors. Acta Pharma Sinica B 5(5):390-401 (2015).
Hudson et al. Cellular delivery of hammerhead ribozymes conjugated to a transferrin receptor antibody. Int J Pharmaceuticals 182(1):49-58 (1999).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Ishikawa et al. Preparation of monomeric Fab'—horseradish peroxidase conjugate using thiol groups in the hinge and its evaluation in enzyme immunoassay and immunohistochemical staining. Ann N Y Acad Sci. 420:74-89 (1983).
Iversen et al. Optimized siRNA-PEG conjugates for extended blood circulation and reduced urine excretion in mice. Theranostics 3(3):201-209 (2013).
Jancik et al. Clinical relevance of KRAS in human cancers. J Biomed Biotechnol 2010:150960 (13 pgs.) (2010).
Jearawiriyapaisarn et al. Sustained Dystrophin Expression Induced by Peptide-conjugated Morpholino Oligomers in the Muscles of mdx Mice. Mol Ther. 16(9): 1624-1629 (2008).
Jones et al. Poly(2-alkylacrylic acid) polymers deliver molecules to the cytosol by pH-sensitive disruption of endosomal vesicles. Biochem J 372:65-75 (2003).
Karpeisky et al. Highly efficient synthesis of 2'-O-amino nucleosides and their incorporation in hammerhead ribozymes. Tetrahedron Lett 39:1131-1134 (1998).
Kemaladewi et al. Dual exon skipping in myostatin and dystrophin for Duchenne muscular dystrophy. BMC Med Genomics. 4:36 (2011).
Khormaee et al. Endosomolytic anionic polymer for the cytoplasmic delivery of siRNAs in localized in vivo applications. Adv Funct Mater 23:565-574 (2013).
Kim et al. PEG conjugated VEGF siRNA for anti-angiogenic gene therapy. J Cont Rel 116:123-129 (2006).
Kohler et al. Continuous cultures of fused cells secreting antibody of predefined specificity. Nature 256:495-497 (1975).
Koizumi. ENA oligonucleotides as therapeutics. Curr Opin Mol Ther 8(2):144-149 (2006).
Kontermann et al. Bispecific antibodies. Drug Discov Today 20(7):838-847 (2015).
Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Lee et al. Antisense PMO cocktails effectively skip dystrophin exons 45-55 in myotubes transdifferentiated from DMD patient fibroblasts. PLoS One 13(5):e0197084 (2018).
Leigh et al. The Human Plasma Proteome: History, Character, and Diagnostic Prospects. Mol Cell Proteomics 1:845-867 (2002).
Levin. Targeting Therapeutic Oligonucleotides. N Engl J Med 376:86-88 (2017).
Loakes. Survey and summary: The applications of universal DNA base analogues. Nucleic Acids Research 29:2437-2447 (2001).
Loh et al. A Survey of siRNA Nanoscal Delivery Patents. 11 Nanotechnology Law & Bus. (pp. 29-37) (2014).
Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
Marshall et al. Arginine-rich cell-penetrating peptides facilitate delivery of antisense oligomers into murine leukocytes and alter pre-mRNA splicing. J Immunol Method 325(1-2):114-26 (2007).
Martinez et al. Single-stranded antisense siRNAs guide target RNA cleavage in RNAi. Cell 110(5):563-574 (2002).
McEnaney et al. Antibody-recruiting molecules: an emerging paradigm for engaging immune function in treating human disease. ACS Chem Biol. 7(7):1139-1151 (2012).
Mei et al. FBXO32 Targets c-Myc for Proteasomal Degradation and Inhibits c-Myc Activity. J Biol Chem 290:16202-16214 (2015).
Miyata et al. Polymer nanotechnology for nucleic acid delivery. Drug Delivery System 31(1):44-53 (2016) (English Abstract).
Monaco et al. An explanation for the phenotypic differences between patients bearing partial deletions of the DMD locus. Genomics 2(1):90-5 (1988).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).

(56) References Cited

OTHER PUBLICATIONS

Mulligan. The basic science of gene therapy. Science 260(5110):926-932 (1993).
Naisbitt et al. Disposition of amodiaquine and related antimalarial agents in human neutrophils: implications for drug design. J Pharmacol Exp Ther 280:884-893 (1997).
Neuberger et al. Recombinant antibodies possessing novel effector functions. Nature 312(5995):604-608 (1984).
Normand-Sdiqui et al. Oligonucleotide delivery: Uptake of rat transferrin receptor antibody (OX / 26) conjugates into an in vitro immortalised cell line model of the blood, brain barrier. Int J Pharmaceuticals 163:63-71 (1998).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
O'Hare et al. Transformation of mouse fibroblasts to methotrexate resistance by a recombinant plasmid expressing a prokaryotic dihydrofolate reductase. PNAS USA 78:1527-1531 (1981).
PCT/CA2018/050881 International Search Report and Written Opinion dated Oct. 4, 2018.
PCT/US2018/012672 International Search Report and Written Opinion dated May 24, 2018.
PCT/US2018/012672 Invitation to Pay Additional Fees dated Mar. 20, 2018.
PCT/US2018/052289 International Search Report and Written Opinion dated Jan. 11, 2019.
Perrault et al. Mixed deoxyribo- and ribo-oligonucleotides with catalytic activity. Nature 344:565-568 (1990).
Pieken et al. Kinetic characterization of ribonuclease-resistant 2'-modified hammerhead ribozymes. Science 253:314-317 (1991).
Rozema et al. Dynamic PolyConjugates for targeted in vivo delivery of siRNA to hepatocytes. PNAS USA 104(32):12982-12987 (2007).
Santerre et al. Expression of prokaryotic genes for hygromycin B and G418 resistance as dominant-selection markers in mouse L cells. Gene 30(1-3):147-156 (1984).
Schnyder et al. Targeting of skeletal muscle in vitro using biotinylated immunoliposomes. Biochem J 377(Pt.1):61-67 (2004).
Schwarz et al. Evidence that siRNAs function as guides, not primers, in the *Drosophila* and human RNAi pathways. Molecular Cell 10:537-548 (2002).
Sekyere et al. Examination of the distribution of the transferrin homologue, melanotransferrin (tumour antigen p97), in mouse and human. Biochimica et Biophysica Acta 1722(2):131-142 (2005).
Singh et al. Recent developments in oligonucleotide conjugation. Chem Soc Rev 39(6):2054-2070 (2010).
Skerra et al. Assembly of a functional Immunoglobulin Fv fragment in *Escherichia coli*. Science 240(4855):1038-1041 (1988).
Strop et al. Location matters: site of conjugation modulates stability and pharmacokinetics of antibody drug conjugates. Chem Biol 20(2):161-167 (2013).
Sugo et al. Development of antibody-siRNA conjugate targeted to cardiac and skeletal muscles. J Control release 237:1-13 (2016).
Summerton, et al. Morpholino antisense oligomers: design, preparation, and properties. Antisense Nucleic Acid Drug Dev. Jun. 1997;7(3):187-95.
Suñé-Pou et al. Targeting Splicing in the Treatment of Human Disease. Genes 8:E87 (2017).
Suriano et al. Beta-catenin (CTNNB1) gene amplification: a new mechanism of protein overexpression in cancer. Genes Chromosomes Cancer 42(3):238-246 (2005).
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Talasila et al. EGFR Wild-type Amplification and Activation Promote Invasion and Development of Glioblastoma Independent of Angiogenesis. Acta Neuropathol. 125(5):683-698 (2013).

Tolstoshev. Gene Therapy, Concepts, Current Trials and Future Directions. Ann. Rev. Pharmacol. Toxicol. 32:573-596 (1993).
U.S. Appl. No. 16/128,450 Miscellaneous Communication re: Third Party Submission dated Jul. 1, 2019.
U.S. Appl. No. 16/128,450 Office Action dated Apr. 19, 2019.
U.S. Appl. No. 16/128,450 Office Action dated Apr. 30, 2020.
U.S. Appl. No. 16/128,450 Office Action dated Dec. 16, 2020.
U.S. Appl. No. 16/128,450 Office Action dated Sep. 19, 2019.
U.S. Appl. No. 16/129,696 Miscellaneous Communication re: Third Party Submission dated Jul. 3, 2019.
U.S. Appl. No. 16/129,696 Office Action dated Apr. 13, 2020.
U.S. Appl. No. 16/129,696 Office Action dated Apr. 17, 2019.
U.S. Appl. No. 16/129,696 Office Action dated Sep. 19, 2019.
U.S. Appl. No. 16/632,827 Office Action dated Feb. 26, 2021.
Usman et al. Exploiting the chemical synthesis of RNA. Trends Biochem Sci 17:334-339 (1992).
Valtorta et al. KRAS gene amplification in colorectal cancer and impact on response to EGFR-targeted therapy. Int J Cancer 133:1259-1266 (2013).
Van Deutekom et al. Antisense-induced exon skipping restores dystrophin expression in DMD patient derived muscle cells. Hum Mol Genet. 10(15):1547-54 (2001).
Van Deutekom et al. Local dystrophin restoration with antisense oligonucleotide PRO051. N Engl J Med 357(26):2677-2686 (2007).
Van Vliet et al. Assessment of the feasibility of exon 45-55 multiexon skipping for duchenne muscular dystrophy. BMC Medical Genetics 9:105 (2008).
Verma et al. Modified oligonucleotides: synthesis and strategy for users. Annu Rev Biochem 67:99-134 (1998).
Walker et al. Improved cellular delivery of antisense oligonucleotides using transferrin receptor antibody-oligonucleotide conjugates. Pharmaceutical research 12(10):1548-1553 (1995).
Ward et al. Binding activities of a repertoire of single immunoglobulin variable domains secreted from *Escherichia coli*. Nature 341(6242):544-546 (1989).
Watts et al. Chemically modified siRNA: tools and applications. Drug Discov Today 13(19-20):842-855 (2008).
Weiner. Liposomes as a Drug Delivery System. Drug Develop Ind Pharm 15:1523 (1989).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Winkler. Oligonucleotide conjugates for therapeutic applications. Ther Del 4(7):791-809 (2013).
Wong et al. Co-injection of a targeted, reversibly masked endosomolytic polymer dramatically improves the efficacy of cholesterol-conjugated small interfering RNAs in vivo. Nucleic Acid Ther 22(6):380-390 (2012).
Wu et al. Building complex glycopeptides: Development of a cysteine-free native chemical ligation protocol. Angew. Chem. Int. Ed. 45:4116-4125 (2006).
Wu et al. Cell-penetrating peptides as transporters for morpholino oligomers: effects of amino acid composition on intracellular delivery and cytotoxicity. Nucleic Acids Res 35(15):5182-5191 (2007).
Wu et al. Delivery systems for gene therapy. Biotherapy 3:87-95 (1991).
Wu et al. Effective rescue of dystrophin improves cardiac function in dystrophin-deficient mice by a modified morpholino oligomer. PNAS USA 105(39):14814-14819 (2008).
Wu et al. Site-specific chemical modification of recombinant proteins produced in mammalian cells by using the genetically encoded aldehyde tag. PNAS USA 106(9):3000-3005 (2009).
Xu et al. Delivery systems for siRNA drug development in cancer therapy. Asian Journal of Pharmaceutical Sciences 10(1):1-12 (2015).
Yessine et al. Characterization of the membrane-destabilizing properties of different pH-sensitive methacrylic acid copolymers. Biochimica et Biophysica Acta 1613:28-38 (2003).
Yuan et al. Development of siRNA payloads to target KRAS-mutant cancer. Cancer Discov 4(10):1182-1197 (2014).
Zhang et al. A remote arene-binding site on prostate specific membrane antigen revealed by antibody-recruiting small molecules. J Am Chem Soc. 132(36):12711-12716 (2010).

(56) References Cited

OTHER PUBLICATIONS

Gooding et al. Oligonucleotide conjugates—Candidates for gene silencing therapeutics. Eur J Pharm Biopharm. 107:321-40 (2016).
U.S. Appl. No. 17/463,473 Office Action dated Dec. 13, 2021.
U.S. Appl. No. 17/463,484 Office Action dated Jan. 4, 2022.
Aartsma-Rus et al., Antisense-induced multiexon skipping for Duchenne muscular dystrophy makes more sense. American Journal of Human Genetics 74(1):83-92 (2004).
Alegre et al. Effect of a Single Amino Acid Mutation on the Activating and Immunosuppressive Properties of a "Humanized" OKT3 Monoclonal Antibody. J Immunol 148:3461-3468 (1992).
Brain and Development 42:117-123 (2010).
Darimont et al. Aug. 2005 Abstract: A novel Antibody-Oligonucleotide Conjugate (AOC) platform enables efficient regulation of muscle targets in mice. Journal Of Cachexia, Sarcopenia And Muscle 8:999-1080 (2017).
Echigoya et al. Quantitative Antisense Screening and Optimization for Exon 51 Skipping in Duchenne Muscular Dystrophy. Mol Ther 25(11):2561-2572 (2017).
Ferreiro et al. Asymptomatic Becker muscular dystrophy in a family with a multiexon deletion. Muscle Nerve 39:239-243 (2009).
Idusogie, et al. Mapping of the C1q binding site on rituxan, a chimeric antibody with a human IgG1 Fc. J Immunol. Apr. 15, 2000;164(8):4178-84.
Kaneko et al. Optimizing Therapeutic Antibody Function: Progress With Fc Domain Engineering. Biodrugs 25(1):1-11 (2011).
Lazar et al. Engineered antibody Fc variants with enhanced effector function. PNAS USA 103(11):4005-10 (2006).
Lee et al. Direct Reprogramming of Human DMD Fibroblasts into Myotubes for In Vitro Evaluation of Antisense-Mediated Exon Skipping and Exons 45-55 Skipping Accompanied by Rescue of Dystrophin Expression. Methods Mol Biol. 1828:141-150 (2018).
Moore et al. Engineered Fc variant antibodies with enhanced ability to recruit complement and mediate effector functions. mAbs 2(2):181-189 (2010).
Nakamura et al. Follow-up of three patients with a large in-frame deletion of exons 45-55 in the Duchenne muscular dystrophy (DMD) gene. J. Clin. Neurosci. 15:757-763 (2008).
Natsume et al. Engineered Antibodies of IgG1/IgG3 Mixed Isotype With Enhanced Cytotoxic Activities. Cancer Res 68(10):3863-72 (2008).
PCT/US2020/029731 International Invitation to Pay Additional Fees dated Aug. 3, 2020.
PCT/US2020/029731 International Search Report and Written Opinion dated Oct. 6, 2020.
Shields et al. High Resolution Mapping of the Binding Site on Human IgG1 for $F_{c\gamma}RI$, $F_{c\gamma}RII$, $F_{c\gamma}RIII$, and FcRn and Design of IgG1 Variants with Improved Binding to the $F_{c\gamma}R$. J Biol Chem 276(9):6591-6604 (2001).
Stavenhagen et al. Enhancing the potency of therapeutic monoclonal antibodies via Fc optimization. Adv Enzyme Regul. 48:152-64 (2008).
Stavenhagen et al. Fc Optimization of Therapeutic Antibodies Enhances Their Ability to Kill Tumor Cells In vitro and Controls Tumor Expansion In vivo via Low-Affinity Activating Fcγ Receptors. Cancer Res 67(18):8882-91 (2007).
Suzuki et al. Endogenous Multiple Exon Skipping and Back-Splicing at the DMD Mutation Hotspot. Int J Mol Sci. 17(10):1722 (2016).
U.S. Appl. No. 16/129,696 Office Action dated Dec. 14, 2020.
U.S. Appl. No. 16/129,696 Office Action dated May 26, 2021.
U.S. Appl. No. 16/649,572 Miscellaneous Communication re: Third Party Submission dated Mar. 19, 2021.
U.S. Appl. No. 16/649,572 Office Action dated Feb. 22, 2023.
Xia et al. Intravenous siRNA of brain cancer with receptor targeting and avidin-biotin technology. Pharm Res 24(12):2309-16 (2007).

* cited by examiner

A

Day 2 after transfection at 5 μM

Day 11 after transfection at 5 μM

B

Day 2 after transfection at 5 μM

Day 11 after transfection at 5 μM

SEQUENCE LISTING

<160> NUMBER OF SEQ ID NOS: 440

<210> SEQ ID NO 1
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 1
gtgtcaccag agtaacagtc tgagtaggag         30

<210> SEQ ID NO 2

```
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 2
aggttgtgtc accagagtaa cagtctgagt                                              30

<210> SEQ ID NO 3
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 3
ggcagtttcc ttagtaacca caggttgtgt                                              30

<210> SEQ ID NO 4
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 4
agatggcagt ttccttagta accacaggtt                                              30

<210> SEQ ID NO 5
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 5
atggcatttc tagtttggag atggcagttt                                              30

<210> SEQ ID NO 6
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 6
ctccaacatc aaggaagatg gcatttctag                                              30

<210> SEQ ID NO 7
<211> LENGTH: 20
<212> TYPE: DNA
<213> ORGANISM: Artificial Sequence
<220> FEATURE:
<223> OTHER INFORMATION: morpholino antisense oligonucleotide

<400> SEQUENCE: 7
tcaaggaaga tggcatttct                                                         20

<210> SEQ ID NO 8
<211> LENGTH: 29
<212> TYPE: DNA
<213> ORGANISM: Artificial Sequence
<220> FEATURE:
<223> OTHER INFORMATION: morpholino antisense oligonucleotide

<400> SEQUENCE: 8
```
tgtcaccaga gtaacagtct gagtaggag                                    29

<210> SEQ ID NO 9
<211> LENGTH: 28
<212> TYPE: DNA
<213> ORGANISM: Artificial Sequence
<220> FEATURE:
<223> OTHER INFORMATION: morpholino antisense oligonucleotide

<400> SEQUENCE: 9
gtcaccagag taacagtctg agtaggag                                     28

<210> SEQ ID NO 10
<211> LENGTH: 27
<212> TYPE: DNA
<213> ORGANISM: Artificial Sequence
<220> FEATURE:
<223> OTHER INFORMATION: morpholino antisense oligonucleotide

<400> SEQUENCE: 10
tcaccagagt aacagtctga gtaggag                                      27

<210> SEQ ID NO 11
<211> LENGTH: 26
<212> TYPE: DNA
<213> ORGANISM: Artificial Sequence
<220> FEATURE:
<223> OTHER INFORMATION: morpholino antisense oligonucleotide

<400> SEQUENCE: 11
caccagagta acagtctgag taggag                                       26

<210> SEQ ID NO 12
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 12
accagagtaa cagtctgagt aggag                                        25

<210> SEQ ID NO 13
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 13
ccacaggttg tgtcaccaga gtaacagtct                                   30

<210> SEQ ID NO 14
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 14
ttataacttg atcaagcaga gaaagccagt                                   30

<210> SEQ ID NO 15
<211> LENGTH: 30
<212> TYPE: DNA

```
<213> ORGANISM: Artificial Sequence
<220> FEATURE:
<223> OTHER INFORMATION: morpholino antisense oligonucleotide

<400> SEQUENCE: 15
ataccttctg cttgatgatc atctcgttga                                    30

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
cagccagtga agaggaagtt ag                                            22

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ccagccattg tgttgaatcc                                               20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
aggacccgtg cttgtaagtg                                               20

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
gattgttcta gcctcttgat tgc                                           23

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
gacaagggcg atttgacag                                                19

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
caagcactca gccagtgaag                                               20
```

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tccagccatt gtgttgaatc                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tccctgagct gaacgggaag                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tccagccatt gtgttgaatc                                              20

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
tcgatgctct tagctgagtg tcc                                          23

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tgatcgtctt cgaacctccg                                              20

<210> SEQ ID NO 27
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 27
ccacaggttg tgtcaccaga gtaacagtct                                   30

<210> SEQ ID NO 28
<211> LENGTH: 30
<212> TYPE: DNA
<213> ORGANISM: Artificial Sequence
<220> FEATURE:

<223> OTHER INFORMATION: morpholino antisense oligonucleotide

<400> SEQUENCE: 28
gtgtcaccag agtaacagtc tgagtaggag                               30

<210> SEQ ID NO 29
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 29
accacaggtt gtgtcaccag agtaacagtc                               30

<210> SEQ ID NO 30
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 30
aggttgtgtc accagagtaa cagtctgagt                               30

<210> SEQ ID NO 31
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 31
cacaggttgt gtcaccagag taacagtctg                               30

<210> SEQ ID NO 32
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 32
tgtgtcacca gagtaacagt ctgagtagga                               30

<210> SEQ ID NO 33
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 33
ttgtgtcacc agagtaacag tctgagtagg                               30

<210> SEQ ID NO 34
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 34
aaccacaggt tgtgtcacca gagtaacagt                               30

```
<210> SEQ ID NO 35
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 35
caggttgtgt caccagagta acagtctgag                                    30

<210> SEQ ID NO 36
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 36
acaggttgtg tcaccagagt aacagtctga                                    30

<210> SEQ ID NO 37
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 37
ggttgtgtca ccagagtaac agtctgagta                                    30

<210> SEQ ID NO 38
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 38
ggcagtttcc ttagtaacca caggttgtgt                                    30

<210> SEQ ID NO 39
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 39
ccttagtaac acaggttgt gtcaccagag                                     30

<210> SEQ ID NO 40
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 40
tccttagtaa ccacaggttg tgtcaccaga                                    30

<210> SEQ ID NO 41
<211> LENGTH: 30
<212> TYPE: DNA
<213> ORGANISM: Artificial Sequence
<220> FEATURE:
<223> OTHER INFORMATION: morpholino antisense oligonucleotide
```

<400> SEQUENCE: 41
tggcagtttc cttagtaacc acaggttgtg                                           30

<210> SEQ ID NO 42
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 42
taaccacagg ttgtgtcacc agagtaacag                                           30

<210> SEQ ID NO 43
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 43
gtaaccacag gttgtgtcac cagagtaaca                                           30

<210> SEQ ID NO 44
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 44
gcagtttcct tagtaaccac aggttgtgtc                                           30

<210> SEQ ID NO 45
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 45
gatggcagtt tccttagtaa ccacaggttg                                           30

<210> SEQ ID NO 46
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 46
agtaaccaca ggttgtgtca ccagagtaac                                           30

<210> SEQ ID NO 47
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 47
agtttcctta gtaaccacag gttgtgtcac                                           30

<210> SEQ ID NO 48
<211> LENGTH: 30

```
<212> TYPE: DNA
<213> ORGANISM: Artificial Sequence
<220> FEATURE:
<223> OTHER INFORMATION: morpholino antisense oligonucleotide

<400> SEQUENCE: 48
gttgtgtcac cagagtaaca gtctgagtag                                    30

<210> SEQ ID NO 49
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 49
cttagtaacc acaggttgtg tcaccagagt                                    30

<210> SEQ ID NO 50
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 50
cagtttcctt agtaaccaca ggttgtgtca                                    30

<210> SEQ ID NO 51
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 51
agatggcagt ttccttagta accacaggtt                                    30

<210> SEQ ID NO 52
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 52
ttccttagta accacaggtt gtgtcaccag                                    30

<210> SEQ ID NO 53
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 53
ttagtaacca caggttgtgt caccagagta                                    30

<210> SEQ ID NO 54
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 54
```
tagtaaccac aggttgtgtc accagagtaa                                    30

<210> SEQ ID NO 55
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 55
gtttccttag taaccacagg ttgtgtcacc                                    30

<210> SEQ ID NO 56
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 56
atggcagttt ccttagtaac cacaggttgt                                    30

<210> SEQ ID NO 57
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 57
tttccttagt aaccacaggt tgtgtcacca                                    30

<210> SEQ ID NO 58
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 58
gagatggcag tttccttagt aaccacaggt                                    30

<210> SEQ ID NO 59
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 59
ggagatggca gtttccttag taaccacagg                                    30

<210> SEQ ID NO 60
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 60
ccaagcccgg ttgaaatctg ccagagcagg                                    30

<210> SEQ ID NO 61
<211> LENGTH: 30
<212> TYPE: DNA
<213> ORGANISM: Artificial Sequence

```
<220> FEATURE:
<223> OTHER INFORMATION: morpholino antisense oligonucleotide

<400> SEQUENCE: 61
cagagcaggt acctccaaca tcaaggaaga                              30

<210> SEQ ID NO 62
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 62
ggcatttcta gtttggagat ggcagtttcc                              30

<210> SEQ ID NO 63
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 63
ctgtccaagc ccggttgaaa tctgccagag                              30

<210> SEQ ID NO 64
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 64
tctgtccaag cccggttgaa atctgccaga                              30

<210> SEQ ID NO 65
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 65
ccagagcagg tacctccaac atcaaggaag                              30

<210> SEQ ID NO 66
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 66
gtccaagccc ggttgaaatc tgccagagca                              30

<210> SEQ ID NO 67
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 67
tgtccaagcc cggttgaaat ctgccagagc                              30
```

-continued

<210> SEQ ID NO 68
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 68
ggaagatggc atttctagtt tggagatggc                                30

<210> SEQ ID NO 69
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 69
tccaagcccg gttgaaatct gccagagcag                                30

<210> SEQ ID NO 70
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 70
agttctgtcc aagcccggtt gaaatctgcc                                30

<210> SEQ ID NO 71
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 71
tggagatggc agtttcctta gtaaccacag                                30

<210> SEQ ID NO 72
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 72
gttctgtcca agcccggttg aaatctgcca                                30

<210> SEQ ID NO 73
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 73
ttctgtccaa gcccggttga aatctgccag                                30

<210> SEQ ID NO 74
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 74
gccagtcggt aagttctgtc caagcccggt                                    30

<210> SEQ ID NO 75
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 75
tgaaatctgc cagagcaggt acctccaaca                                    30

<210> SEQ ID NO 76
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 76
agtttggaga tggcagtttc cttagtaacc                                    30

<210> SEQ ID NO 77
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 77
caagcccggt tgaaatctgc cagagcaggt                                    30

<210> SEQ ID NO 78
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 78
tctagtttgg agatggcagt ttccttagta                                    30

<210> SEQ ID NO 79
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 79
agagcaggta cctccaacat caaggaagat                                    30

<210> SEQ ID NO 80
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 80
ctgccagagc aggtacctcc aacatcaagg                                    30

<210> SEQ ID NO 81

```
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 81
agcccggttg aaatctgcca gagcaggtac                                      30

<210> SEQ ID NO 82
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 82
gaaatctgcc agagcaggta cctccaacat                                      30

<210> SEQ ID NO 83
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 83
tgccagagca ggtacctcca acatcaagga                                      30

<210> SEQ ID NO 84
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 84
aagcccggtt gaaatctgcc agagcaggta                                      30

<210> SEQ ID NO 85
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 85
gccagagcag gtacctccaa catcaaggaa                                      30

<210> SEQ ID NO 86
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 86
taagttctgt ccaagcccgg ttgaaatctg                                      30

<210> SEQ ID NO 87
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 87
```
ggttgaaatc tgccagagca ggtacctcca                                30

<210> SEQ ID NO 88
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 88
agatggcatt tctagtttgg agatggcagt                                30

<210> SEQ ID NO 89
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 89
gttgaaatct gccagagcag gtacctccaa                                30

<210> SEQ ID NO 90
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 90
gcccggttga aatctgccag agcaggtacc                                30

<210> SEQ ID NO 91
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 91
ttgaaatctg ccagagcagg tacctccaac                                30

<210> SEQ ID NO 92
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 92
ttggagatgg cagtttcctt agtaaccaca                                30

<210> SEQ ID NO 93
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 93
ctccaacatc aaggaagatg gcatttctag                                30

<210> SEQ ID NO 94
<211> LENGTH: 30
<212> TYPE: DNA

```
<213> ORGANISM: Artificial Sequence
<220> FEATURE:
<223> OTHER INFORMATION: morpholino antisense oligonucleotide

<400> SEQUENCE: 94
tttggagatg gcagtttcct tagtaaccac                                            30

<210> SEQ ID NO 95
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 95
cggttgaaat ctgccagagc aggtacctcc                                            30

<210> SEQ ID NO 96
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 96
gcatttctag tttggagatg gcagtttcct                                            30

<210> SEQ ID NO 97
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 97
tcaaggaaga tggcatttct agtttggaga                                            30

<210> SEQ ID NO 98
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 98
agccagtcgg taagttctgt ccaagcccgg                                            30

<210> SEQ ID NO 99
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 99
tctgccagag caggtacctc caacatcaag                                            30

<210> SEQ ID NO 100
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 100
cccggttgaa atctgccaga gcaggtacct                                            30
```

-continued

<210> SEQ ID NO 101
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 101
aagttctgtc caagcccggt tgaaatctgc                                    30

<210> SEQ ID NO 102
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 102
ccagtcggta agttctgtcc aagcccggtt                                    30

<210> SEQ ID NO 103
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 103
gtaagttctg tccaagcccg gttgaaatct                                    30

<210> SEQ ID NO 104
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 104
ggtaagttct gtccaagccc ggttgaaatc                                    30

<210> SEQ ID NO 105
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 105
ccggttgaaa tctgccagag caggtacctc                                    30

<210> SEQ ID NO 106
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 106
gtttggagat ggcagtttcc ttagtaacca                                    30

<210> SEQ ID NO 107
<211> LENGTH: 30
<212> TYPE: DNA
<213> ORGANISM: Artificial Sequence
<220> FEATURE:

<223> OTHER INFORMATION: morpholino antisense oligonucleotide

<400> SEQUENCE: 107
caaggaagat ggcatttcta gtttggagat                                              30

<210> SEQ ID NO 108
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 108
gagcaggtac ctccaacatc aaggaagatg                                              30

<210> SEQ ID NO 109
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 109
ctagtttgga gatggcagtt tccttagtaa                                              30

<210> SEQ ID NO 110
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 110
tccaacatca aggaagatgg catttctagt                                              30

<210> SEQ ID NO 111
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 111
cagtcggtaa gttctgtcca agcccggttg                                              30

<210> SEQ ID NO 112
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 112
gaagatggca tttctagttt ggagatggca                                              30

<210> SEQ ID NO 113
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 113
ccaacatcaa ggaagatggc atttctagtt                                              30

```
<210> SEQ ID NO 114
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 114
cggtaagttc tgtccaagcc cggttgaaat                                30

<210> SEQ ID NO 115
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 115
ttctagtttg gagatggcag tttccttagt                                30

<210> SEQ ID NO 116
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 116
aatctgccag agcaggtacc tccaacatca                                30

<210> SEQ ID NO 117
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 117
gtcggtaagt tctgtccaag cccggttgaa                                30

<210> SEQ ID NO 118
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 118
agtcggtaag ttctgtccaa gcccggttga                                30

<210> SEQ ID NO 119
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 119
gcaggtacct ccaacatcaa ggaagatggc                                30

<210> SEQ ID NO 120
<211> LENGTH: 30
<212> TYPE: DNA
<213> ORGANISM: Artificial Sequence
<220> FEATURE:
<223> OTHER INFORMATION: morpholino antisense oligonucleotide
```

```
<400> SEQUENCE: 120
tagtttggag atggcagttt ccttagtaac                              30

<210> SEQ ID NO 121
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 121
aagccagtcg gtaagttctg tccaagcccg                              30

<210> SEQ ID NO 122
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 122
acctccaaca tcaaggaaga tggcatttct                              30

<210> SEQ ID NO 123
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 123
atctgccaga gcaggtacct ccaacatcaa                              30

<210> SEQ ID NO 124
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 124
atcaaggaag atggcatttc tagtttggag                              30

<210> SEQ ID NO 125
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 125
tcggtaagtt ctgtccaagc ccggttgaaa                              30

<210> SEQ ID NO 126
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 126
aggaagatgg catttctagt ttggagatgg                              30

<210> SEQ ID NO 127
<211> LENGTH: 30
```

```
<212> TYPE: DNA
<213> ORGANISM: Artificial Sequence
<220> FEATURE:
<223> OTHER INFORMATION: morpholino antisense oligonucleotide

<400> SEQUENCE: 127
aaatctgcca gagcaggtac ctccaacatc                                    30

<210> SEQ ID NO 128
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 128
cctccaacat caaggaagat ggcatttcta                                    30

<210> SEQ ID NO 129
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 129
gatggcattt ctagtttgga gatggcagtt                                    30

<210> SEQ ID NO 130
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 130
tttctagttt ggagatggca gtttccttag                                    30

<210> SEQ ID NO 131
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 131
catttctagt ttggagatgg cagtttcctt                                    30

<210> SEQ ID NO 132
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 132
aagatggcat ttctagtttg gagatggcag                                    30

<210> SEQ ID NO 133
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 133
```
aaggaagatg gcatttctag tttggagatg            30

<210> SEQ ID NO 134
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 134
tacctccaac atcaaggaag atggcatttc            30

<210> SEQ ID NO 135
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 135
gaaagccagt cggtaagttc tgtccaagcc            30

<210> SEQ ID NO 136
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 136
aaagccagtc ggtaagttct gtccaagccc            30

<210> SEQ ID NO 137
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 137
agcaggtacc tccaacatca aggaagatgg            30

<210> SEQ ID NO 138
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 138
agaaagccag tcggtaagtt ctgtccaagc            30

<210> SEQ ID NO 139
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 139
catcaaggaa gatggcattt ctagtttgga            30

<210> SEQ ID NO 140
<211> LENGTH: 30
<212> TYPE: DNA
<213> ORGANISM: Artificial Sequence

```
<220> FEATURE:
<223> OTHER INFORMATION: morpholino antisense oligonucleotide

<400> SEQUENCE: 140
gagaaagcca gtcggtaagt tctgtccaag                                    30

<210> SEQ ID NO 141
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 141
gtacctccaa catcaaggaa gatggcattt                                    30

<210> SEQ ID NO 142
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 142
acatcaagga agatggcatt tctagtttgg                                    30

<210> SEQ ID NO 143
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 143
caggtacctc caacatcaag gaagatggca                                    30

<210> SEQ ID NO 144
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 144
agagaaagcc agtcggtaag ttctgtccaa                                    30

<210> SEQ ID NO 145
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 145
ggtacctcca acatcaagga agatggcatt                                    30

<210> SEQ ID NO 146
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 146
aggtacctcc aacatcaagg aagatggcat                                    30
```

```
<210> SEQ ID NO 147
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 147
caacatcaag gaagatggca tttctagttt                                            30

<210> SEQ ID NO 148
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 148
aacatcaagg aagatggcat ttctagtttg                                            30

<210> SEQ ID NO 149
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 149
gcagagaaag ccagtcggta agttctgtcc                                            30

<210> SEQ ID NO 150
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 150
cagagaaagc cagtcggtaa gttctgtcca                                            30

<210> SEQ ID NO 151
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 151
atttctagtt tggagatggc agtttcctta                                            30

<210> SEQ ID NO 152
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 152
tggcatttct agtttggaga tggcagtttc                                            30

<210> SEQ ID NO 153
<211> LENGTH: 30
<212> TYPE: DNA
<213> ORGANISM: Artificial Sequence
<220> FEATURE:
<223> OTHER INFORMATION: morpholino antisense oligonucleotide
```

<400> SEQUENCE: 153
caagcagaga aagccagtcg gtaagttctg                                    30

<210> SEQ ID NO 154
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 154
atggcatttc tagtttggag atggcagttt                                    30

<210> SEQ ID NO 155
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 155
tcaagcagag aaagccagtc ggtaagttct                                    30

<210> SEQ ID NO 156
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 156
aagcagagaa agccagtcgg taagttctgt                                    30

<210> SEQ ID NO 157
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 157
atcaagcaga gaaagccagt cggtaagttc                                    30

<210> SEQ ID NO 158
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 158
agcagagaaa gccagtcggt aagttctgtc                                    30

<210> SEQ ID NO 159
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 159
acttgatcaa gcagagaaag ccagtcggta                                    30

<210> SEQ ID NO 160

```
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 160
aacttgatca agcagagaaa gccagtcggt                                               30

<210> SEQ ID NO 161
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 161
taacttgatc aagcagagaa agccagtcgg                                               30

<210> SEQ ID NO 162
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 162
gatcaagcag agaaagccag tcggtaagtt                                               30

<210> SEQ ID NO 163
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 163
tataacttga tcaagcagag aaagccagtc                                               30

<210> SEQ ID NO 164
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 164
tgatcaagca gagaaagcca gtcggtaagt                                               30

<210> SEQ ID NO 165
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 165
ttgatcaagc agagaaagcc agtcggtaag                                               30

<210> SEQ ID NO 166
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 166
```
ataacttgat caagcagaga aagccagtcg                                              30

<210> SEQ ID NO 167
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 167
cttgatcaag cagagaaagc cagtcggtaa                                              30

<210> SEQ ID NO 168
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 168
ttataacttg atcaagcaga gaaagccagt                                              30

<210> SEQ ID NO 169
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 169
tttataactt gatcaagcag agaaagccag                                              30

<210> SEQ ID NO 170
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 170
tgattttata acttgatcaa gcagagaaag                                              30

<210> SEQ ID NO 171
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 171
gattttataa cttgatcaag cagagaaagc                                              30

<210> SEQ ID NO 172
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 172
tcaccctctg tgattttata acttgatcaa                                              30

<210> SEQ ID NO 173
<211> LENGTH: 30
<212> TYPE: DNA

```
<213> ORGANISM: Artificial Sequence
<220> FEATURE:
<223> OTHER INFORMATION: morpholino antisense oligonucleotide

<400> SEQUENCE: 173
gtcacccacc atcaccctct gtgattttat                                    30

<210> SEQ ID NO 174
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 174
ttttataact tgatcaagca gagaaagcca                                    30

<210> SEQ ID NO 175
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 175
cctcaaggtc acccaccatc accctctgtg                                    30

<210> SEQ ID NO 176
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 176
attttataac ttgatcaagc agagaaagcc                                    30

<210> SEQ ID NO 177
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 177
caccctctgt gattttataa cttgatcaag                                    30

<210> SEQ ID NO 178
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 178
ggtcacccac catcaccctc tgtgatttta                                    30

<210> SEQ ID NO 179
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 179
tcctcaaggt cacccaccat caccctctgt                                    30
```

```
<210> SEQ ID NO 180
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 180
atcaccctct gtgattttat aacttgatca                                30

<210> SEQ ID NO 181
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 181
ctcaaggtca cccaccatca ccctctgtga                                30

<210> SEQ ID NO 182
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 182
atcctcaagg tcacccacca tcaccctctg                                30

<210> SEQ ID NO 183
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 183
tcaaggtcac ccaccatcac cctctgtgat                                30

<210> SEQ ID NO 184
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 184
tcacccacca tcaccctctg tgattttata                                30

<210> SEQ ID NO 185
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 185
cccaccatca ccctctgtga ttttataact                                30

<210> SEQ ID NO 186
<211> LENGTH: 30
<212> TYPE: DNA
<213> ORGANISM: Artificial Sequence
<220> FEATURE:
```

<223> OTHER INFORMATION: morpholino antisense oligonucleotide

<400> SEQUENCE: 186
caccatcacc ctctgtgatt ttataacttg                              30

<210> SEQ ID NO 187
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 187
gtgattttat aacttgatca agcagagaaa                              30

<210> SEQ ID NO 188
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 188
acccaccatc accctctgtg attttataac                              30

<210> SEQ ID NO 189
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 189
caaggtcacc caccatcacc ctctgtgatt                              30

<210> SEQ ID NO 190
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 190
aggtcaccca ccatcaccct ctgtgatttt                              30

<210> SEQ ID NO 191
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 191
ccctctgtga ttttataact tgatcaagca                              30

<210> SEQ ID NO 192
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 192
cacccaccat caccctctgt gattttataa                              30

```
<210> SEQ ID NO 193
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 193
atatcctcaa ggtcacccac catcaccctc                                   30

<210> SEQ ID NO 194
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 194
accatcaccc tctgtgattt tataacttga                                   30

<210> SEQ ID NO 195
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 195
tatcctcaag gtcacccacc atcccctct                                    30

<210> SEQ ID NO 196
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 196
accctctgtg attttataac ttgatcaagc                                   30

<210> SEQ ID NO 197
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 197
aaggtcaccc accatcaccc tctgtgattt                                   30

<210> SEQ ID NO 198
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 198
ccaccatcac cctctgtgat tttataactt                                   30

<210> SEQ ID NO 199
<211> LENGTH: 30
<212> TYPE: DNA
<213> ORGANISM: Artificial Sequence
<220> FEATURE:
<223> OTHER INFORMATION: morpholino antisense oligonucleotide
```

<400> SEQUENCE: 199
ccatcaccct ctgtgatttt ataacttgat                              30

<210> SEQ ID NO 200
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 200
catcaccctc tgtgatttta taacttgatc                              30

<210> SEQ ID NO 201
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 201
gatatcctca aggtcaccca ccatcaccct                              30

<210> SEQ ID NO 202
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 202
cctctgtgat tttataactt gatcaagcag                              30

<210> SEQ ID NO 203
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 203
ctgtgatttt ataacttgat caagcagaga                              30

<210> SEQ ID NO 204
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 204
tgatatcctc aaggtcaccc accatcaccc                              30

<210> SEQ ID NO 205
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 205
ttgatatcct caaggtcacc caccatcacc                              30

<210> SEQ ID NO 206
<211> LENGTH: 30

```
<212> TYPE: DNA
<213> ORGANISM: Artificial Sequence
<220> FEATURE:
<223> OTHER INFORMATION: morpholino antisense oligonucleotide

<400> SEQUENCE: 206
tgtgatttta taacttgatc aagcagagaa                                    30

<210> SEQ ID NO 207
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 207
gttgatatcc tcaaggtcac ccaccatcac                                    30

<210> SEQ ID NO 208
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 208
cgttgatatc ctcaaggtca cccaccatca                                    30

<210> SEQ ID NO 209
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 209
tcgttgatat cctcaaggtc acccaccatc                                    30

<210> SEQ ID NO 210
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 210
ctcgttgata tcctcaaggt cacccaccat                                    30

<210> SEQ ID NO 211
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 211
tctcgttgat atcctcaagg tcacccacca                                    30

<210> SEQ ID NO 212
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 212
```

```
catctcgttg atatcctcaa ggtcacccac                                30

<210> SEQ ID NO 213
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 213
tcatctcgtt gatatcctca aggtcaccca                                30

<210> SEQ ID NO 214
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 214
atctcgttga tatcctcaag gtcacccacc                                30

<210> SEQ ID NO 215
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 215
atcatctcgt tgatatcctc aaggtcaccc                                30

<210> SEQ ID NO 216
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 216
gatcatctcg ttgatatcct caaggtcacc                                30

<210> SEQ ID NO 217
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 217
ctctgtgatt ttataacttg atcaagcaga                                30

<210> SEQ ID NO 218
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 218
tgatcatctc gttgatatcc tcaaggtcac                                30

<210> SEQ ID NO 219
<211> LENGTH: 30
<212> TYPE: DNA
<213> ORGANISM: Artificial Sequence
```

```
<220> FEATURE:
<223> OTHER INFORMATION: morpholino antisense oligonucleotide

<400> SEQUENCE: 219
tctgtgattt tataacttga tcaagcagag                                30

<210> SEQ ID NO 220
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 220
atgatcatct cgttgatatc ctcaaggtca                                30

<210> SEQ ID NO 221
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 221
gatgatcatc tcgttgatat cctcaaggtc                                30

<210> SEQ ID NO 222
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 222
tgatgatcat ctcgttgata tcctcaaggt                                30

<210> SEQ ID NO 223
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 223
ttgatgatca tctcgttgat atcctcaagg                                30

<210> SEQ ID NO 224
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 224
gcttgatgat catctcgttg atatcctcaa                                30

<210> SEQ ID NO 225
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 225
cttgatgatc atctcgttga tatcctcaag                                30
```

<210> SEQ ID NO 226
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 226
tgcttgatga tcatctcgtt gatatcctca                               30

<210> SEQ ID NO 227
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 227
ctgcttgatg atcatctcgt tgatatcctc                               30

<210> SEQ ID NO 228
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 228
tctgcttgat gatcatctcg ttgatatcct                               30

<210> SEQ ID NO 229
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 229
ttctgcttga tgatcatctc gttgatatcc                               30

<210> SEQ ID NO 230
<211> LENGTH: 30
<212> TYPE: DNA
<213> ORGANISM: Artificial Sequence
<220> FEATURE:
<223> OTHER INFORMATION: morpholino antisense oligonucleotide

<400> SEQUENCE: 230
cttctgcttg atgatcatct cgttgatatc                               30

<210> SEQ ID NO 231
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 231
gtaaccacag gttgtgtcac cagag                                    25

<210> SEQ ID NO 232
<211> LENGTH: 25
<212> TYPE: DNA
<213> ORGANISM: Artificial Sequence
<220> FEATURE:
<223> OTHER INFORMATION: morpholino antisense oligonucleotide

```
<400> SEQUENCE: 232
aaccacaggt tgtgtcacca gagta                                          25

<210> SEQ ID NO 233
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 233
acaggttgtg tcaccagagt aacag                                          25

<210> SEQ ID NO 234
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 234
ccacaggttg tgtcaccaga gtaac                                          25

<210> SEQ ID NO 235
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 235
accacaggtt gtgtcaccag agtaa                                          25

<210> SEQ ID NO 236
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 236
ggcagtttcc ttagtaacca caggt                                          25

<210> SEQ ID NO 237
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 237
cacaggttgt gtcaccagag taaca                                          25

<210> SEQ ID NO 238
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 238
aggttgtgtc accagagtaa cagtc                                          25

<210> SEQ ID NO 239
```

```
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 239
caggttgtgt caccagagta acagt                                         25

<210> SEQ ID NO 240
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 240
accagagtaa cagtctgagt aggag                                         25

<210> SEQ ID NO 241
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 241
ggttgtgtca ccagagtaac agtct                                         25

<210> SEQ ID NO 242
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 242
taaccacagg ttgtgtcacc agagt                                         25

<210> SEQ ID NO 243
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 243
tggcagtttc cttagtaacc acagg                                         25

<210> SEQ ID NO 244
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 244
gcagtttcct tagtaaccac aggtt                                         25

<210> SEQ ID NO 245
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 245
```
agtaaccaca ggttgtgtca ccaga                                            25

<210> SEQ ID NO 246
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 246
ccttagtaac cacaggttgt gtcac                                            25

<210> SEQ ID NO 247
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 247
gtgtcaccag agtaacagtc tgagt                                            25

<210> SEQ ID NO 248
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 248
caccagagta acagtctgag tagga                                            25

<210> SEQ ID NO 249
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 249
tgtgtcacca gagtaacagt ctgag                                            25

<210> SEQ ID NO 250
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 250
tccttagtaa ccacaggttg tgtca                                            25

<210> SEQ ID NO 251
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 251
tcaccagagt aacagtctga gtagg                                            25

<210> SEQ ID NO 252
<211> LENGTH: 25
<212> TYPE: DNA

```
<213> ORGANISM: Artificial Sequence
<220> FEATURE:
<223> OTHER INFORMATION: morpholino antisense oligonucleotide

<400> SEQUENCE: 252
gtcaccagag taacagtctg agtag                                        25

<210> SEQ ID NO 253
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 253
ttccttagta accacaggtt gtgtc                                        25

<210> SEQ ID NO 254
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 254
gtttccttag taaccacagg ttgtg                                        25

<210> SEQ ID NO 255
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 255
cagtttcctt agtaaccaca ggttg                                        25

<210> SEQ ID NO 256
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 256
gatggcagtt tccttagtaa ccaca                                        25

<210> SEQ ID NO 257
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 257
gttgtgtcac cagagtaaca gtctg                                        25

<210> SEQ ID NO 258
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 258
ttgtgtcacc agagtaacag tctga                                        25
```

```
<210> SEQ ID NO 259
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 259
tgtcaccaga gtaacagtct gagta                                    25

<210> SEQ ID NO 260
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 260
tttccttagt aaccacaggt tgtgt                                    25

<210> SEQ ID NO 261
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 261
cttagtaacc acaggttgtg tcacc                                    25

<210> SEQ ID NO 262
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 262
atggcagttt ccttagtaac cacag                                    25

<210> SEQ ID NO 263
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 263
tctgtccaag cccggttgaa atctg                                    25

<210> SEQ ID NO 264
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 264
tctgccagag caggtacctc caaca                                    25

<210> SEQ ID NO 265
<211> LENGTH: 25
<212> TYPE: DNA
<213> ORGANISM: Artificial Sequence
<220> FEATURE:
```

```
<223> OTHER INFORMATION: morpholino antisense oligonucleotide

<400> SEQUENCE: 265
cccggttgaa atctgccaga gcagg                                              25

<210> SEQ ID NO 266
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 266
agtttcctta gtaaccacag gttgt                                              25

<210> SEQ ID NO 267
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 267
agatggcagt ttccttagta accac                                              25

<210> SEQ ID NO 268
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 268
tagtaaccac aggttgtgtc accag                                              25

<210> SEQ ID NO 269
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 269
ccagagcagg tacctccaac atcaa                                              25

<210> SEQ ID NO 270
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 270
ctgccagagc aggtacctcc aacat                                              25

<210> SEQ ID NO 271
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 271
cagagcaggt acctccaaca tcaag                                              25
```

```
<210> SEQ ID NO 272
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 272
gccagagcag gtacctccaa catca                                         25

<210> SEQ ID NO 273
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 273
tgccagagca ggtacctcca acatc                                         25

<210> SEQ ID NO 274
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 274
gttctgtcca agcccggttg aaatc                                         25

<210> SEQ ID NO 275
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 275
ctgtccaagc ccggttgaaa tctgc                                         25

<210> SEQ ID NO 276
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 276
ttctgtccaa gcccggttga aatct                                         25

<210> SEQ ID NO 277
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 277
gcccggttga aatctgccag agcag                                         25

<210> SEQ ID NO 278
<211> LENGTH: 25
<212> TYPE: DNA
<213> ORGANISM: Artificial Sequence
<220> FEATURE:
<223> OTHER INFORMATION: morpholino antisense oligonucleotide
```

```
<400> SEQUENCE: 278
agagcaggta cctccaacat caagg                                           25

<210> SEQ ID NO 279
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 279
gagatggcag tttccttagt aacca                                           25

<210> SEQ ID NO 280
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 280
ggcatttcta gtttggagat ggcag                                           25

<210> SEQ ID NO 281
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 281
agttctgtcc aagcccggtt gaaat                                           25

<210> SEQ ID NO 282
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 282
ttagtaacca caggttgtgt cacca                                           25

<210> SEQ ID NO 283
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 283
tgtccaagcc cggttgaaat ctgcc                                           25

<210> SEQ ID NO 284
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 284
aagttctgtc caagcccggt tgaaa                                           25

<210> SEQ ID NO 285
<211> LENGTH: 25
```

```
<212> TYPE: DNA
<213> ORGANISM: Artificial Sequence
<220> FEATURE:
<223> OTHER INFORMATION: morpholino antisense oligonucleotide

<400> SEQUENCE: 285
ggtaagttct gtccaagccc ggttg                                     25

<210> SEQ ID NO 286
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 286
gcatttctag tttggagatg gcagt                                     25

<210> SEQ ID NO 287
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 287
aagcccggtt gaaatctgcc agagc                                     25

<210> SEQ ID NO 288
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 288
ccaagcccgg ttgaaatctg ccaga                                     25

<210> SEQ ID NO 289
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 289
taagttctgt ccaagcccgg ttgaa                                     25

<210> SEQ ID NO 290
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 290
gtccaagccc ggttgaaatc tgcca                                     25

<210> SEQ ID NO 291
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 291
```
atggcatttc tagtttggag atggc                                              25

<210> SEQ ID NO 292
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 292
agcccggttg aaatctgcca gagca                                              25

<210> SEQ ID NO 293
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 293
cggtaagttc tgtccaagcc cggtt                                              25

<210> SEQ ID NO 294
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 294
ccggttgaaa tctgccagag caggt                                              25

<210> SEQ ID NO 295
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 295
tcggtaagtt ctgtccaagc ccggt                                              25

<210> SEQ ID NO 296
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 296
caagcccggt tgaaatctgc cagag                                              25

<210> SEQ ID NO 297
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 297
gtaagttctg tccaagcccg gttga                                              25

<210> SEQ ID NO 298
<211> LENGTH: 25
<212> TYPE: DNA
<213> ORGANISM: Artificial Sequence

```
<220> FEATURE:
<223> OTHER INFORMATION: morpholino antisense oligonucleotide

<400> SEQUENCE: 298
tccaagcccg gttgaaatct gccag                                          25

<210> SEQ ID NO 299
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 299
gaaatctgcc agagcaggta cctcc                                          25

<210> SEQ ID NO 300
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 300
ggagatggca gtttccttag taacc                                          25

<210> SEQ ID NO 301
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 301
atctgccaga gcaggtacct ccaac                                          25

<210> SEQ ID NO 302
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 302
gtcggtaagt tctgtccaag cccgg                                          25

<210> SEQ ID NO 303
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 303
ggttgaaatc tgccagagca ggtac                                          25

<210> SEQ ID NO 304
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 304
gaagatggca tttctagttt ggaga                                          25
```

<210> SEQ ID NO 305
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 305
ttctagtttg gagatggcag tttcc                                           25

<210> SEQ ID NO 306
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 306
tttctagttt ggagatggca gtttc                                           25

<210> SEQ ID NO 307
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 307
aatctgccag agcaggtacc tccaa                                           25

<210> SEQ ID NO 308
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 308
ggaagatggc atttctagtt tggag                                           25

<210> SEQ ID NO 309
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 309
cggttgaaat ctgccagagc aggta                                           25

<210> SEQ ID NO 310
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 310
gcagagaaag ccagtcggta agttc                                           25

<210> SEQ ID NO 311
<211> LENGTH: 25
<212> TYPE: DNA
<213> ORGANISM: Artificial Sequence
<220> FEATURE:
<223> OTHER INFORMATION: morpholino antisense oligonucleotide

```
<400> SEQUENCE: 311
gagcaggtac ctccaacatc aagga                                        25

<210> SEQ ID NO 312
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 312
cagtcggtaa gttctgtcca agccc                                        25

<210> SEQ ID NO 313
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 313
gagaaagcca gtcggtaagt tctgt                                        25

<210> SEQ ID NO 314
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 314
agtcggtaag ttctgtccaa gcccg                                        25

<210> SEQ ID NO 315
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 315
tgaaatctgc cagagcaggt acctc                                        25

<210> SEQ ID NO 316
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 316
tttggagatg gcagtttcct tagta                                        25

<210> SEQ ID NO 317
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 317
aaatctgcca gagcaggtac ctcca                                        25

<210> SEQ ID NO 318
```

```
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 318
agagaaagcc agtcggtaag ttctg                                             25

<210> SEQ ID NO 319
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 319
ccagtcggta agttctgtcc aagcc                                             25

<210> SEQ ID NO 320
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 320
gccagtcggt aagttctgtc caagc                                             25

<210> SEQ ID NO 321
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 321
tggagatggc agtttcctta gtaac                                             25

<210> SEQ ID NO 322
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 322
tctagtttgg agatggcagt ttcct                                             25

<210> SEQ ID NO 323
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 323
gcaggtacct ccaacatcaa ggaag                                             25

<210> SEQ ID NO 324
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 324
```

```
atttctagtt tggagatggc agttt                                          25

<210> SEQ ID NO 325
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 325
aaagccagtc ggtaagttct gtcca                                          25

<210> SEQ ID NO 326
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 326
gaaagccagt cggtaagttc tgtcc                                          25

<210> SEQ ID NO 327
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 327
ttggagatgg cagtttcctt agtaa                                          25

<210> SEQ ID NO 328
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 328
caagcagaga aagccagtcg gtaag                                          25

<210> SEQ ID NO 329
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 329
agcagagaaa gccagtcggt aagtt                                          25

<210> SEQ ID NO 330
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 330
gatcaagcag agaaagccag tcggt                                          25

<210> SEQ ID NO 331
<211> LENGTH: 25
<212> TYPE: DNA
```

```
<213> ORGANISM: Artificial Sequence
<220> FEATURE:
<223> OTHER INFORMATION: morpholino antisense oligonucleotide

<400> SEQUENCE: 331
aagcagagaa agccagtcgg taagt                                    25

<210> SEQ ID NO 332
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 332
tgatcaagca gagaaagcca gtcgg                                    25

<210> SEQ ID NO 333
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 333
agaaagccag tcggtaagtt ctgtc                                    25

<210> SEQ ID NO 334
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 334
atcaagcaga gaaagccagt cggta                                    25

<210> SEQ ID NO 335
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 335
acctccaaca tcaaggaaga tggca                                    25

<210> SEQ ID NO 336
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 336
agcaggtacc tccaacatca aggaa                                    25

<210> SEQ ID NO 337
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 337
cagagaaagc cagtcggtaa gttct                                    25
```

<210> SEQ ID NO 338
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 338
gttgaaatct gccagagcag gtacc                                         25

<210> SEQ ID NO 339
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 339
aggaagatgg catttctagt ttgga                                         25

<210> SEQ ID NO 340
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 340
aagatggcat ttctagtttg gagat                                         25

<210> SEQ ID NO 341
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 341
ttgaaatctg ccagagcagg tacct                                         25

<210> SEQ ID NO 342
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 342
cttgatcaag cagagaaagc cagtc                                         25

<210> SEQ ID NO 343
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 343
ctccaacatc aaggaagatg gcatt                                         25

<210> SEQ ID NO 344
<211> LENGTH: 25
<212> TYPE: DNA
<213> ORGANISM: Artificial Sequence
<220> FEATURE:

```
<223> OTHER INFORMATION: morpholino antisense oligonucleotide

<400> SEQUENCE: 344
cctccaacat caaggaagat ggcat                                          25

<210> SEQ ID NO 345
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 345
tggcatttct agtttggaga tggca                                          25

<210> SEQ ID NO 346
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 346
atcaaggaag atggcatttc tagtt                                          25

<210> SEQ ID NO 347
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 347
agtttggaga tggcagtttc cttag                                          25

<210> SEQ ID NO 348
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 348
gatggcattt ctagtttgga gatgg                                          25

<210> SEQ ID NO 349
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 349
catttctagt ttggagatgg cagtt                                          25

<210> SEQ ID NO 350
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 350
tcaagcagag aaagccagtc ggtaa                                          25
```

<210> SEQ ID NO 351
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 351
agccagtcgg taagttctgt ccaag                                  25

<210> SEQ ID NO 352
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 352
acttgatcaa gcagagaaag ccagt                                  25

<210> SEQ ID NO 353
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 353
ccaacatcaa ggaagatggc atttc                                  25

<210> SEQ ID NO 354
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 354
aagccagtcg gtaagttctg tccaa                                  25

<210> SEQ ID NO 355
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 355
aaggaagatg gcatttctag tttgg                                  25

<210> SEQ ID NO 356
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 356
agatggcatt tctagtttgg agatg                                  25

<210> SEQ ID NO 357
<211> LENGTH: 25
<212> TYPE: DNA
<213> ORGANISM: Artificial Sequence
<220> FEATURE:
<223> OTHER INFORMATION: morpholino antisense oligonucleotide

```
<400> SEQUENCE: 357
aacttgatca agcagagaaa gccag                                         25

<210> SEQ ID NO 358
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 358
tacctccaac atcaaggaag atggc                                         25

<210> SEQ ID NO 359
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 359
ttgatcaagc agagaaagcc agtcg                                         25

<210> SEQ ID NO 360
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 360
gtttggagat ggcagtttcc ttagt                                         25

<210> SEQ ID NO 361
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 361
gtacctccaa catcaaggaa gatgg                                         25

<210> SEQ ID NO 362
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 362
catcaaggaa gatggcattt ctagt                                         25

<210> SEQ ID NO 363
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 363
acatcaagga agatggcatt tctag                                         25

<210> SEQ ID NO 364
<211> LENGTH: 25
```

```
<212> TYPE: DNA
<213> ORGANISM: Artificial Sequence
<220> FEATURE:
<223> OTHER INFORMATION: morpholino antisense oligonucleotide

<400> SEQUENCE: 364
ctagtttgga gatggcagtt tcctt                                            25

<210> SEQ ID NO 365
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 365
caaggaagat ggcatttcta gtttg                                            25

<210> SEQ ID NO 366
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 366
gtcacccacc atcaccctct gtgat                                            25

<210> SEQ ID NO 367
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 367
tccaacatca aggaagatgg cattt                                            25

<210> SEQ ID NO 368
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 368
taacttgatc aagcagagaa agcca                                            25

<210> SEQ ID NO 369
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 369
tcaaggaaga tggcatttct agttt                                            25

<210> SEQ ID NO 370
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 370
```
caggtacctc aacatcaag gaaga                                          25

<210> SEQ ID NO 371
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 371
caacatcaag gaagatggca tttct                                         25

<210> SEQ ID NO 372
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 372
ggtcacccac catcaccctc tgtga                                         25

<210> SEQ ID NO 373
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 373
ataacttgat caagcagaga aagcc                                         25

<210> SEQ ID NO 374
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 374
ggtacctcca acatcaagga agatg                                         25

<210> SEQ ID NO 375
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 375
aggtcaccca ccatcaccct ctgtg                                         25

<210> SEQ ID NO 376
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 376
aacatcaagg aagatggcat ttcta                                         25

<210> SEQ ID NO 377
<211> LENGTH: 25
<212> TYPE: DNA
<213> ORGANISM: Artificial Sequence

```
<220> FEATURE:
<223> OTHER INFORMATION: morpholino antisense oligonucleotide

<400> SEQUENCE: 377
tagtttggag atggcagttt cctta                                              25

<210> SEQ ID NO 378
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 378
ttataacttg atcaagcaga gaaag                                              25

<210> SEQ ID NO 379
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 379
tcacccacca tcaccctctg tgatt                                              25

<210> SEQ ID NO 380
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 380
cacccaccat caccctctgt gattt                                              25

<210> SEQ ID NO 381
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 381
tttataactt gatcaagcag agaaa                                              25

<210> SEQ ID NO 382
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 382
caaggtcacc caccatcacc ctctg                                              25

<210> SEQ ID NO 383
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 383
tataacttga tcaagcagag aaagc                                              25
```

```
<210> SEQ ID NO 384
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 384
cccaccatca ccctctgtga tttta                                             25

<210> SEQ ID NO 385
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 385
acccaccatc accctctgtg atttt                                             25

<210> SEQ ID NO 386
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 386
tcaaggtcac ccaccatcac cctct                                             25

<210> SEQ ID NO 387
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 387
atcctcaagg tcacccacca tcacc                                             25

<210> SEQ ID NO 388
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 388
aaggtcaccc accatcaccc tctgt                                             25

<210> SEQ ID NO 389
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 389
tcctcaaggt cacccaccat caccc                                             25

<210> SEQ ID NO 390
<211> LENGTH: 25
<212> TYPE: DNA
<213> ORGANISM: Artificial Sequence
<220> FEATURE:
<223> OTHER INFORMATION: morpholino antisense oligonucleotide
```

```
<400> SEQUENCE: 390
cctcaaggtc acccaccatc accct                                          25

<210> SEQ ID NO 391
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 391
atatcctcaa ggtcacccac catca                                          25

<210> SEQ ID NO 392
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 392
ctcaaggtca cccaccatca ccctc                                          25

<210> SEQ ID NO 393
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 393
aggtacctcc aacatcaagg aagat                                          25

<210> SEQ ID NO 394
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 394
tatcctcaag gtcacccacc atcac                                          25

<210> SEQ ID NO 395
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 395
ctctgtgatt ttataacttg atcaa                                          25

<210> SEQ ID NO 396
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 396
ccaccatcac cctctgtgat tttat                                          25

<210> SEQ ID NO 397
```

```
<210> SEQ ID NO 397
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 397
cctctgtgat tttataactt gatca                                         25

<210> SEQ ID NO 398
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 398
gatatcctca aggtcaccca ccatc                                         25

<210> SEQ ID NO 399
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 399
ttttataact tgatcaagca gagaa                                         25

<210> SEQ ID NO 400
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 400
ctcgttgata tcctcaaggt caccc                                         25

<210> SEQ ID NO 401
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 401
tcgttgatat cctcaaggtc accca                                         25

<210> SEQ ID NO 402
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 402
tgatatcctc aaggtcaccc accat                                         25

<210> SEQ ID NO 403
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 403
```

```
cgttgatatc tcaaggtca cccac                                          25
```

<210> SEQ ID NO 404
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 404

```
attttataac ttgatcaagc agaga                                         25
```

<210> SEQ ID NO 405
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 405

```
tctcgttgat atcctcaagg tcacc                                         25
```

<210> SEQ ID NO 406
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 406

```
caccctctgt gattttataa cttga                                         25
```

<210> SEQ ID NO 407
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 407

```
gttgatatcc tcaaggtcac ccacc                                         25
```

<210> SEQ ID NO 408
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 408

```
tctgtgattt tataacttga tcaag                                         25
```

<210> SEQ ID NO 409
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 409

```
ccctctgtga ttttataact tgatc                                         25
```

<210> SEQ ID NO 410
<211> LENGTH: 25
<212> TYPE: DNA

```
<213> ORGANISM: Artificial Sequence
<220> FEATURE:
<223> OTHER INFORMATION: morpholino antisense oligonucleotide

<400> SEQUENCE: 410
atctcgttga tatcctcaag gtcac                                         25

<210> SEQ ID NO 411
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 411
ttgatatcct caaggtcacc cacca                                         25

<210> SEQ ID NO 412
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 412
catctcgttg atatcctcaa ggtca                                         25

<210> SEQ ID NO 413
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 413
tcaccctctg tgattttata acttg                                         25

<210> SEQ ID NO 414
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 414
caccatcacc ctctgtgatt ttata                                         25

<210> SEQ ID NO 415
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 415
tcatctcgtt gatatcctca aggtc                                         25

<210> SEQ ID NO 416
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 416
gatcatctcg ttgatatcct caagg                                         25
```

```
<210> SEQ ID NO 417
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 417
gattttataa cttgatcaag cagag                                              25

<210> SEQ ID NO 418
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 418
tgatcatctc gttgatatcc tcaag                                              25

<210> SEQ ID NO 419
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 419
gatgatcatc tcgttgatat cctca                                              25

<210> SEQ ID NO 420
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 420
atgatcatct cgttgatatc ctcaa                                              25

<210> SEQ ID NO 421
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 421
tgatgatcat ctcgttgata cctc                                               25

<210> SEQ ID NO 422
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 422
ttgatgatca tctcgttgat atcct                                              25

<210> SEQ ID NO 423
<211> LENGTH: 25
<212> TYPE: DNA
<213> ORGANISM: Artificial Sequence
<220> FEATURE:
```

-continued

<223> OTHER INFORMATION: morpholino antisense oligonucleotide

<400> SEQUENCE: 423
atcatctcgt tgatatcctc aaggt                                              25

<210> SEQ ID NO 424
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 424
cttgatgatc atctcgttga tatcc                                              25

<210> SEQ ID NO 425
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 425
accctctgtg attttataac ttgat                                              25

<210> SEQ ID NO 426
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 426
tgcttgatga tcatctcgtt gatat                                              25

<210> SEQ ID NO 427
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 427
gcttgatgat catctcgttg atatc                                              25

<210> SEQ ID NO 428
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 428
ccatcaccct ctgtgatttt ataac                                              25

<210> SEQ ID NO 429
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 429
ctgcttgatg atcatctcgt tgata                                              25

```
<210> SEQ ID NO 430
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 430
accatcaccc tctgtgattt tataa                                       25

<210> SEQ ID NO 431
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 431
catcaccctc tgtgatttta taact                                       25

<210> SEQ ID NO 432
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 432
tctgcttgat gatcatctcg ttgat                                       25

<210> SEQ ID NO 433
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 433
ttctgcttga tgatcatctc gttga                                       25

<210> SEQ ID NO 434
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 434
cttctgcttg atgatcatct cgttg                                       25

<210> SEQ ID NO 435
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 435
ctgtgatttt ataacttgat caagc                                       25

<210> SEQ ID NO 436
<211> LENGTH: 25
<212> TYPE: DNA
<213> ORGANISM: Artificial Sequence
<220> FEATURE:
<223> OTHER INFORMATION: morpholino antisense oligonucleotide
```

```
<400> SEQUENCE: 436
atcaccctct gtgattttat aactt                                            25

<210> SEQ ID NO 437
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 437
gtgattttat aacttgatca agcag                                            25

<210> SEQ ID NO 438
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 438
tgattttata acttgatcaa gcaga                                            25

<210> SEQ ID NO 439
<211> LENGTH: 25
<212> TYPE: DNA
<213> ORGANISM: Artificial Sequence
<220> FEATURE:
<223> OTHER INFORMATION: morpholino antisense oligonucleotide

<400> SEQUENCE: 439
tgtgatttta taacttgatc aagca                                            25

<210> SEQ ID NO 440
<211> LENGTH: 20
<212> TYPE: DNA
<213> ORGANISM: Artificial Sequence
<220> FEATURE:
<223> OTHER INFORMATION: Table 1. control hGAPDH_860 79_Rv

<400> SEQUENCE: 440
ggaggagtgg gtgtcgctgt                                                  20
```

ANTISENSE OLIGONUCLEOTIDES THAT BIND TO EXON 51 OF HUMAN DYSTROPHIN PRE-MRNA

CROSS-REFERENCE TO RELATED APPLICATIONS

This application is a continuation of U.S. patent application Ser. No. 16/632,827, filed on Jan. 21, 2020, which is a U.S. National Phase Entry of International Application No. PCT/CA2018/050881, filed on Jul. 20, 2018, which claims the benefit of foreign priority to Application No. GB 1711809.2, filed Jul. 21, 2017, each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Feb. 15, 2020, is named 45532-746-301_SL.txt and is 92,718 bytes in size.

BACKGROUND OF THE INVENTION

Disruption of alternative splicing underlies many diseases, and modulation of splicing using antisense oligonucleotides can have therapeutic implications. Splice-switching antisense oligonucleotides (SSOs) are emerging treatments for neuromuscular diseases, with several SSOs currently undergoing clinical trials for conditions such as spinal muscular atrophy (SMA) and Duchenne muscular dystrophy (DMD), where antisense-mediated exon skipping can restore the open reading frame and allow the synthesis of partly or wholly functional proteins instead of non-functional ones.

Duchenne muscular dystrophy (DMD) is one of the most prevalent lethal genetic disorders in boys worldwide, with an incidence of approx. 1 in 3,600-9,337 live male births. DMD is caused by the absence of dystrophin protein due to mutations in the dystrophin (DMD) gene. The gene encoding the protein contains 79 exons spread out over more than 2 million nucleotides of DNA. Any exonic mutation that changes the reading frame of the exon, or introduces a stop codon, or is characterized by removal of an entire out of frame exon or exons or duplications of one or more exons has the potential to disrupt production of functional dystrophin, resulting in DMD. A less severe form of muscular dystrophy, Becker muscular dystrophy (BMD) has been found to arise where a mutation, typically a deletion of one or more exons, results in a correct reading frame along the entire dystrophin transcript, such that translation of mRNA into protein is not prematurely terminated. If the joining of the upstream and downstream exons in the processing of a mutated dystrophin pre-mRNA maintains the correct reading frame of the gene, the result is an mRNA coding for a protein with a short internal deletion that retains some activity resulting in a Becker Page 1 Header phenotype. Deletions of an exon or exons which do not alter the reading frame of a dystrophin protein give rise to a BMD phenotype, whereas an exon deletion that causes a frame-shift will give rise to DMD (MonAc0, Bertelson et al. 1988). In general, dystrophin mutations including point mutations and exon deletions that change the reading frame and thus interrupt proper protein translation result in DMD.

Currently one of the most promising therapeutic avenues is exon skipping using antisense oligonucleotides (AOs). Exon skipping can restore the reading frame by removing the mutant exon and/or its flanking exon(s) from the DMD pre-mRNA, enabling the production of truncated but partly-functional dystrophin protein. A majority of DMD patients harbour deletion mutations and 20% of these are amenable to exon 51 skipping.

In September 2016, the US Food and Drug Administration (FDA) conditionally approved the first DMD antisense drug, eteplirsen (Exondys 51), which was developed to exclude exon 51 from mutant DMD. Eteplirsen is an AO modified with a phosphorodiamidate morpholino oligomer (morpholino or PMO), an antisense chemistry that has been well-established in terms of its safety and effectiveness. However, eteplirsen remains controversial as there is only weak evidence supporting the effectiveness of the drug, both in terms of restoring dystrophin protein to therapeutically beneficial levels, and improving clinical outcomes. The FDA has previously rejected another drug candidate for DMD exon 51 skipping: the 2'-O-methyl-phosphorothioate-based AO 'drisapersen'. Although therapeutics must ensure the highest possible benefit for the lowest amount of risk, no significant improvements in muscle function were demonstrated upon treatment with drisapersen, and its use led to concerns over safety.

Therefore, exon skipping therapies currently face a major challenge in that their observed efficacy in patients has been very low despite the fact that significant therapeutic effects have been demonstrated in many animal studies.

Exon skipping efficiency is largely dependent on the AO target sequence: however, there has been little debate or discussion that the sequences targeted by eteplirsen and drisapersen might not be the optimal choices for exon skipping therapy. Several groups have undertaken large-scale AO screening efforts to determine effective AO sequences computationally and empirically. However, the exon skipping effectiveness of designed AOs has not been evaluated both quantitatively and statistically. Although restoring dystrophin protein expression is necessary to improve dystrophic muscle function, the ability of AOs to rescue dystrophin protein expression has not been reported with sufficient Page 2 Header methods of quantification in previous AO screening studies. Other studies have highly relied on RT-PCR from primary DMD muscle cells. It is remarkable that the AO sequences of eteplirsen and drisapersen were determined only within this context.

Thus, the effectiveness of exon 51 skipping therapy could be improved by selecting more optimal AO sequences, and by performing more rigorous AO screening using a more reliable and direct biological measure—such as rescued dystrophin protein in DMD—for validating the best antisense oligonucleotides to be taken forward in a clinical trial.

It is an aim of one or more aspects of the present invention to address one or more such problems in the art.

SUMMARY OF THE INVENTION

According to a first aspect of the present invention, there is provided an antisense oligonucleotide capable of binding to exon 51 of human dystrophin pre-mRNA, wherein binding of the antisense oligonucleotide takes place entirely within the region between 0 and +89 of the pre-mRNA sequence, and wherein the antisense oligonucleotide comprises at least 27 bases.

According to a second aspect of the present invention, there is provided a conjugate comprising an antisense oligonucleotide according to the first aspect and a carrier, wherein the carrier is conjugated to the antisense oligonucleotide.

According to a third aspect of the present invention, there is provided a cell loaded with a conjugate of the second aspect.

According to a fourth aspect of the present invention, there is provided a pharmaceutical composition comprising an antisense oligonucleotide according to the first aspect, and/or a conjugate according to the second aspect, and a pharmaceutically acceptable excipient. According to a fifth aspect of the present invention, there is provided a method of treating a muscular disorder in a subject, comprising administering an effective amount of an antisense oligonucleotide capable of binding to exon 51 of human dystrophin pre-mRNA to a subject, wherein binding of the antisense oligonucleotide takes place entirely within the region between 0 and +89 of the pre-mRNA sequence, and wherein the antisense oligonucleotide comprises at least 27 bases.

According to a sixth aspect of the present invention, there is provided an antisense oligonucleotide capable of binding to exon 51 of human dystrophin pre-mRNA for use in the treatment of a muscular disorder in a subject, wherein binding of the antisense oligonucleotide takes place entirely within the region between 0 and +89 of the pre-mRNA sequence, and wherein the antisense oligonucleotide comprises at least 27 bases.

According to a seventh aspect of the present invention, there is provided a method of increasing human dystrophin protein expression in a cell comprising contacting the cell with an effective amount of an antisense oligonucleotide capable of binding to exon 51 of human dystrophin pre-mRNA, wherein binding of the antisense oligonucleotide takes place entirely within the region between 0 and +89 of the pre-mRNA sequence, and wherein the antisense oligonucleotide comprises at least 27 bases.

DETAILED DESCRIPTION OF THE INVENTION

The inventors have developed a series of antisense oligonucleotides binding within the early region at 0 to +89 of exon 51 of the dystrophin pre-mRNA sequence and which have a longer than usual length of at least 27 bases, each having remarkable efficiency and effectiveness.

In order to produce the antisense oligonucleotides, the inventors performed a study which quantitatively evaluated the effectiveness of morpholino-based antisense oligonucleotides for exon 51 skipping using a systematic screening method involving in silico, in vitro, and in vivo tests.

The inventors carried out a combination screening using a computational analysis to predict exon skipping efficiency of designed antisense oligonucleotide sequences followed by in vitro tests of morpholino antisense oligonucleotides in immortalized DMD patient-derived muscle cell lines. This research revealed that the beginning of the human dystrophin exon 51 sequence is a very promising target region for inducing exon skipping, specifically the region of 0 to +89 of the sequence. This is notably different from the internal region targeted by the known eteplirsen and drisapersen antisense therapies.

The antisense oligonucleotides identified from this region were then optimised for the most effective restoration of dystrophin production in muscle cells. Various factors were investigated, including the length of the antisense oligonucleotides. Surprisingly, the inventors found that antisense oligonucleotides binding in this early region are more effective when they are longer than many of the known antisense oligonucleotide sequences against exon 51. Specifically, the inventors identified an upward trend correlating effectiveness with the length of the antisense oligonucleotide from 27 bases and longer. The inventors have shown that just a few bases difference means the antisense oligonucleotide has a significantly different efficiency. As demonstrated herein, 30-mer antisense oligonucleotides work up to 1.5-fold better than a 25-mer of the same sequence (42% vs. 65% skipping efficiency). Without wishing to be bound by theory, this may be because longer sequences can be more specific to the target sequence and less likely to cause off-target effects.

It is demonstrated herein that the inventors' optimisation of these identified antisense oligonucleotide sequences has enabled efficiency in exon 51 skipping and in rescuing dystrophin protein to increase by up to more than 12-fold and 7-fold respectively compared to the industry standard 'eteplirsen' sequence. Furthermore, statistically significant in vivo exon 51 skipping by the most effective antisense oligonucleotide identified through these in vitro screenings was confirmed using transgenic mice harbouring the human DMD gene, which has never been shown for the eteplirsen or drisapersen antisense oligonucleotides. Accordingly, the antisense oligonucleotides described herein are shown to provide an effective therapy and treatment for muscular disorders, especially for the treatment of DMD. These antisense oligonucleotides are not only providing an alternative therapy into a field of medicine in which only one such drug has been approved for market. They also provide an improved option for treatment which is several times more effective at increasing dystrophin protein expression. This is expected to provide a viable option for treatment for those suffering from DMD and other muscular disorders with strong evidence to support the effectiveness of the therapy.

For the avoidance of doubt, and in order to clarify the way in which the present disclosure is to be interpreted, certain terms used in accordance with the present invention will now be defined further.

The invention includes any combination of the aspects and features described except where such a combination is clearly impermissible or expressly avoided.

It is noted that where aspects of the invention may refer methods or uses including an antisense oligonucleotide, this may also include a conjugate or pharmaceutical composition comprising an antisense oligonucleotide as defined herein.

The section headings used herein are for organisational purposes only and are not to be construed as limiting the subject matter described.

Antisense Oligonucleotide

The present invention relates to antisense oligonucleotides having a length of at least 27 bases that bind to exon 51 of human dystrophin pre-mRNA within the region of 0 to +89 which can be used to treat muscular disorders.

Suitably, 'antisense oligonucleotides' may be referred to herein as 'AOs' or 'oligos' or 'oligomers'.

Suitably the antisense oligonucleotide induces skipping of exon 51 of the human dystrophin gene.

Suitably the antisense oligonucleotide increases skipping of exon 51 of the human dystrophin gene.

Suitably the antisense oligonucleotide allows expression of functional human dystrophin protein.

Suitably the antisense oligonucleotide increases expression of functional human dystrophin protein.

Suitably, the antisense oligonucleotide comprises at least 28 bases, suitably at least 29 bases, suitably at least 30 bases.

Suitably, the antisense oligonucleotide comprises between 27 and 30 bases. In one embodiment, the antisense oligonucleotide comprises 30 bases.

In one embodiment, the antisense oligonucleotide consists of 30 bases.

Suitably, the binding of the antisense oligonucleotide takes place entirely within the region between 0 and +88, 0 and +87, 0 and +86, 0 and +85, 0 and +84, 0 and +83, 0 and +82, 0 and +81, 0 and +80, 0 and +79, 0 and +78 of the pre-mRNA sequence.

In one embodiment, the binding of the antisense oligonucleotide takes place entirely within the region between 0 and +78 of the pre-mRNA sequence.

Suitably, the antisense oligonucleotide comprises at least 27 bases of one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide comprises at least 28 bases of one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide comprises at least 29 bases of one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide comprises at least 27 contiguous bases of one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide comprises at least 28 contiguous bases of one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide comprises at least 29 contiguous bases of one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide shares at least 70%, at least 80%, at least 90%, at least 95%, at least 96%, at least 97%, at least 98%, or at least 99% identity with one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide shares between 90% and 100% identity with one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide shares at least 70%, at least 80%, at least 90%, at least 95%, at least 96%, at least 97%, at least 98%, or at least 99% homology with one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide shares between 90% and 100% homology with one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide may comprise a variant antisense oligonucleotide which differs from one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48) by 1, 2, 3, 4, 5, 6, 7, 8, 9, or 10 bases.

Suitably, the antisense oligonucleotide may comprise a variant antisense oligonucleotide which differs from one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48) by up to 3 bases. Suitably, the antisense oligonucleotide may comprise a variant antisense oligonucleotide which differs from one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48) by up to 2 bases. Suitably, the antisense oligonucleotide may comprise a variant antisense oligonucleotide which differs from one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48) by a single base. Suitably, the antisense oligonucleotide comprises one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide consists of one of the following sequences: SEQ ID NO.1 (Ac0), SEQ ID NO.2 (Ac5), SEQ ID NO.3 (Ac26), SEQ ID NO.4 (Ac30), or SEQ ID NO.5 (Ac48).

Suitably, the antisense oligonucleotide comprises SEQ ID NO.1 (Ac0) or SEQ ID NO.5 (Ac48).

In one embodiment, the antisense oligonucleotide comprises SEQ ID NO.1 (Ac0).

Suitably, the antisense oligonucleotide consists of SEQ ID NO.1 (Ac0) or SEQ ID NO.5 (Ac48).

In one embodiment, the antisense oligonucleotide consists of SEQ ID NO.1 (Ac0).

It will be appreciated that the invention may further include aspects directed towards each of the individual antisense oligonucleotide sequences listed in Table 3 i.e. an antisense oligonucleotide comprising or consisting of any of the sequences listed in Table 3. Furthermore, in accordance with the second aspect of the invention, a conjugate comprising an antisense oligonucleotide as listed in Table 3 is envisaged. Furthermore a pharmaceutical composition in accordance with the fourth aspect of the invention, comprising an antisense oligonucleotide as listed in Table 3 or a conjugate thereof is envisaged. Furthermore a medical use in accordance with the fifth aspect of the invention, comprising an antisense oligonucleotide as listed in Table 3 for the treatment of a muscular disorder is envisaged. Furthermore a method of treatment in accordance with the sixth aspect comprising an antisense oligonucleotide as listed in Table 3 is envisaged. Furthermore a method of increasing human dystrophin protein expression in a cell in accordance with the seventh aspect comprising an antisense oligonucleotide as listed in Table 3 is envisaged.

Suitably, the antisense oligonucleotide is synthetic, and non-natural.

Suitably, the antisense oligonucleotide may be routinely made through the well-known technique of solid phase synthesis. Equipment for such synthesis is sold by several manufacturers including, for example, Applied Biosystems (Foster City, Calif.). One method for synthesising oligonucleotides on a modified solid support is described in U.S. Pat. No. 4,458,066. Any other means for such synthesis known in the art may additionally or alternatively be employed.

Suitably, the antisense oligonucleotide is an antisense oligonucleotide analogue.

Suitably, the term 'oligonucleotide analogue' and 'nucleotide analogue' refer to any modified synthetic analogues of oligonucleotides or nucleotides respectively that are known in the art.

Suitable examples of oligonucleotide analogues include peptide nucleic acids (PNAs), morpholino oligonucleotides, phosphorothioate oligonucleotides, phosphorodithioate oligonucleotides, alkylphosphonate oligonucleotides, acylphosphonate oligonucleotides and phosphoramidite oligonucleotides.

Suitably, the antisense oligonucleotide comprises morpholino subunits. Suitably therefore, the antisense oligonucleotide is a morpholino antisense oligonucleotide.

Suitably, the antisense oligonucleotide comprises morpholino subunits linked together by phosphorus-containing linkages. Suitably therefore, the antisense oligonucleotide is a phosphoramidate or phosphorodiamidate morpholino antisense oligonucleotide.

The terms 'morpholino antisense oligonucleotide' or ?MO' (phosphoramidate or phosphorodiamidate morpholino oligonucleotide) refer to an antisense oligonucleotide Page 9 Header analog composed of morpholino subunit structures, where (i) the structures are linked together by phosphorus-containing linkages, suitably one to three atoms long, suitably two atoms long, and suitably uncharged or cationic, joining the morpholino nitrogen of one subunit to a 5' exocyclic carbon of an adjacent subunit, and (ii) each morpholino ring bears a purine or pyrimidine base-pairing moiety effective to bind, by base specific hydrogen bonding, to a base in a polynucleotide.

Suitably, the antisense oligonucleotide comprises phosphorus-containing intersubunit linkages joining a morpholino nitrogen of one subunit to a 5' exocyclic carbon of an adjacent subunit.

Suitably, the antisense oligonucleotide comprises phosphorus-containing intersubunit linkages in accordance with the following structure (I):

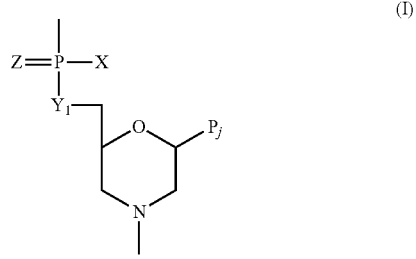

(I)

wherein:
Y1 is 0, S, NH—, or —CH2-;
Z is 0 or S;
Pj is a purine or pyrimidine base-pairing moiety effective to bind, by base-specific hydrogen bonding, to a base in a polynucleotide; and X is fluoro, optionally substituted alkyl, optionally substituted alkoxy, optionally substituted thioalkoxy, amino, optionally substituted alkylamino, or optionally substituted heterocyclyl.

Optionally, variations can be made to the intersubunit linkage as long as the variations do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to the phosphorus may be unsubstituted, monosubstituted, or disubstituted with (optionally substituted) lower alkyl.

Suitably, the synthesis, structures, and binding characteristics of morpholino oligonucleotides are detailed in U.S. Pat. Nos. 5,698,685, 5,217,866, 5,142,047, 5,034,506, 5,166,315, 5,521,063, and 5,506,337, and PCT Appn. No. PCT/US07/11435.

Binding of the Antisense Oligonucleotide

The present invention relates to an antisense oligonucleotide capable of binding within the region 0 to +89 of exon 51 of human dystrophin pre-mRNA.

By 'capable of binding' it is meant that the antisense oligonucleotide comprises a sequence with is able to bind to human dystrophin pre-mRNA in the region stated.

Suitably, the antisense oligonucleotide is complementary to a sequence of human dystrophin pre-mRNA in the region stated.

Suitably, the antisense oligonucleotide comprises a sequence which is complementary to a sequence of human dystrophin pre-mRNA in the region stated.

The antisense oligonucleotide and a sequence within the region 0 to +89 of exon 51 of human dystrophin pre-mRNA are complementary to each other when a sufficient number of corresponding positions in each molecule are occupied by nucleotides which can hydrogen bond with each other and thereby cause exon skipping, suitably exon skipping of exon 51. Thus, 'hybridisable' and 'complementary' are terms which are used to indicate a sufficient degree of complementarity or pairing such that stable and specific binding occurs between the antisense oligonucleotide and a sequence within region 0 to +89 of exon 51 of human dystrophin pre-mRNA. Suitably, the antisense oligonucleotide is sufficiently hybridisable and/or complementary to a sequence within region 0 to +89 of exon 51 of human dystrophin pre-mRNA to induce exon skipping, suitably exon skipping of exon 51. Suitably, the antisense oligonucleotide may not be 100% complementary to a sequence within region of 0 to +89 of exon 51 of human dystrophin pre-mRNA. However, suitably the antisense oligonucleotide is sufficiently complementary to avoid non-specific binding.

Suitably, the antisense oligonucleotide is at least 70%, at least 80%, at least 90%, at least 95%, at least 96%, at least 97%, at least 98% at least 99% complementary to a sequence within the region 0 to +89 of exon 51 of human dystrophin pre-mRNA.

It is understood that in order for the antisense oligonucleotide to be capable of binding, it does not require that the entire length of the antisense oligonucleotide binds to the human dystrophin pre-mRNA. It will be appreciated that a portion of the antisense oligonucleotide Page 11 Header may not bind to the human dystrophin pre-mRNA, for example the 5' or the 3' ends of the antisense oligonucleotide. However, in accordance with the first aspect, the parts of the antisense oligonucleotide which are bound to the human dystrophin pre-mRNA must fall within the region of 0 to +89 of exon 51.

Suitably, therefore, the antisense oligonucleotide is hybridisable to a sequence within the region of 0 to +89 of exon 51 of human dystrophin pre-mRNA. Suitably, the antisense oligonucleotide is sufficiently hybridisable to a sequence within the region of 0 to +89 of exon 51 of human dystrophin pre-mRNA to cause exon skipping of exon 51.

Human Dystrophin

The present invention relates to a therapeutic antisense oligonucleotide for use in the treatment of muscular disorders, particularly dystrophin disorders such as DMD.

Dystrophin is a rod-shaped cytoplasmic protein, and a vital part of the protein complex that connects the cytoskeleton of a muscle fibre to the surrounding extracellular matrix through the cell membrane.

Dystrophin protein contains multiple functional domains. The DMD gene, encoding the dystrophin protein, is one of the longest known human genes covering 2.3 megabases (0.08% of the human genome) at locus Xp21. The primary transcript in muscle measures about 2,100 kilobases and takes 16 hours to transcribe; the mature mRNA measures 14.0 kilobases. The 79-exon muscle transcript codes for a protein of 3685 amino acid residues. Dystrophin protein contains an actin binding domain and a central rod domain. This large central domain is formed by 24 spectrin-like triple-helical elements of about 109 amino acids, which have homology to alpha-actinin and spectrin. The repeats are typically interrupted by four proline-rich non-repeat segments, also referred to as hinge regions. Each repeat is encoded by two exons, typically interrupted by an intron between amino acids 47 and 48 in the first part of alpha-helix 2. The other intron is found at different positions in the repeat, usually scattered over helix 3. Dystrophin also contains a cysteine-rich domain including a cysteine-rich segment (i.e., 15 Cysteines in 280 amino acids).

In normal cases, the amino-terminus of dystrophin binds to F-actin and the carboxy-terminus binds to the dystrophin-associated protein complex (DAPC) at the sarcolemma. The DAPC includes the dystroglycans, sarcoglycans, integrins and caveolin, and mutations in any of these components cause autosomally inherited muscular dystrophies. Normal skeletal muscle tissue contains only small amounts of dystrophin (about 0.002% of total muscle protein), but its absence (or abnormal expression) leads to the development of a Page 12 Header severe and currently incurable symptoms most readily characterized by several aberrant intracellular signaling pathways that ultimately yield pronounced myofiber necrosis as well as progressive muscle weakness and fatigability. The DAPC is destabilized when dystrophin is absent, which results in diminished levels of the member proteins, and in turn leads to progressive fibre damage and membrane leakage. In various forms of muscular dystrophy, such as Duchenne's muscular dystrophy (DMD) and Becker's muscular dystrophy (BMD), muscle cells produce an altered and functionally defective form of dystrophin, or no dystrophin at all, mainly due to mutations in the gene sequence that lead to incorrect splicing. The predominant expression of the defective dystrophin protein, or the complete lack of dystrophin or a dystrophin-like protein, leads to rapid progression of muscle degeneration.

The mRNA encoding dystrophin in muscular dystrophy patients typically contains out-of-frame mutations (e.g. deletions, insertions or splice site mutations), resulting in frameshift or early termination of the translation process, so that in most muscle fibres no functional dystrophin is produced.

Suitably, the antisense oligonucleotide triggers exon skipping to restore the reading frame of the dystrophin mRNA. Suitably, the antisense oligonucleotide triggers exon skipping of exon 51 to restore the reading frame of the dystrophin mRNA. Suitably, restoration of the reading frame restores production of a partially functional dystrophin protein.

Suitably, the partially functional dystrophin is a truncated dystrophin protein.

Suitably, the truncated dystrophin protein is the same dystrophin protein produced in patients suffering from the less severe muscular disorder; BMD.

Muscular Disorder

The present invention relates to the use of therapeutic antisense oligonucleotides in the treatment of muscular disorders.

Suitably the muscular disorder is selected from any muscular disorder resulting from a genetic mutation.

Suitably the muscular disorder is selected from any muscular disorder resulting from a genetic mutation in a gene associated with muscle function.

Suitably the muscular disorder is selected from any muscular disorder resulting from a genetic mutation in the human dystrophin gene.

Suitably, the muscular disorder is selected from any muscular dystrophy disorder.

Suitably, the muscular disorder is selected from Duchenne muscular dystrophy, Becker muscular dystrophy, congenital muscular dystrophy, Distal muscular dystrophy, Emery-Dreifuss muscular dystrophy, Facioscapulohumeral muscular dystrophy, Limb-girdle muscular dystrophy, Myotonic muscular dystrophy, Oculopharyngeal Muscular dystrophy. Suitably, the muscular disorder is Duchenne Muscular Dystrophy (DMD) or Becker Muscular Dystrophy (BMD).

In one embodiment, the muscular disorder is DMD.

Carrier and Conjugate

The present invention also relates to a conjugate of the antisense oligonucleotide with a carrier.

Suitably, the carrier may comprise any molecule operable to transport the antisense oligonucleotide into a target cell, suitably into a muscle cell.

Suitable carriers may include; peptides, small molecule chemicals, polymers, nanoparticles, lipids, liposomes, exosomes or the like.

Suitably, the carrier is a peptide. The peptide may be selected from viral proteins such as VP22 (derived from herpes virus tegument protein), snake venom protein such as CyLOP-1 (derived from crotamin), cell adhesion glycoproteins such as pVEC (derived from murine vascular endothelial-cadherin protein), Penetratin (Antennapedia homeodomain), Tat (human immunodeficiency virus transactivating regulatory protein) or reverse Tat, for example.

Suitably, the peptide is a cell penetrating peptide.

Suitably, the peptide is an arginine-rich cell penetrating peptide.

The use of arginine-rich peptide carriers is particularly useful. Certain arginine based peptide carriers have been shown to be highly effective at delivery of antisense compounds into primary cells including muscle cells (Marshall, Oda et al. 2007; Jearawiriyapaisarn, Moulton et al. 2008; Wu, Moulton et al. 2008). Furthermore, compared to other peptides, the arginine peptide carriers when conjugated to an antisense oligonucleotide, demonstrate an enhanced ability to alter splicing of several gene transcripts (Marshall, Oda et al. 2007). Suitably, the arginine-rich cell penetrating peptide may be selected from those carrier peptides described in WO2015075747, WO2013030569, WO2009147368, US20120289457, or US20160237426, for example.

In one embodiment, the arginine rich cell penetrating peptide is selected from those described in WO2013030569 or WO2009147368.

Suitably, the carrier has the capability of inducing cell penetration of the antisense oligonucleotide within at least 30%, 40%, 50%, 60%, 70%, 80%, 90%, or 100% of cells of a given cell culture population. Suitably, the carrier has the capability of inducing cell penetration of the antisense oligonucleotide within at least 30%, 40%, 50%, 60%, 70%, 80%, 90%, or 100% of muscle cells in a muscle cell culture.

Suitably, conjugation of the carrier to the antisense oligonucleotide may be at any position suitable for forming a covalent bond between the carrier and the antisense oligonucleotide or between the linker moiety and the antisense oligonucleotide. For example, conjugation of a carrier may be at the 3' end of the antisense oligonucleotide. Alternatively, conjugation of a carrier to the antisense oligonucleotide may be at the 5' end of the oligonucleotide. Alternatively, a carrier may be conjugated to the antisense oligonucleotide through any of the intersubunit linkages.

Suitably, the carrier is covalently coupled at its N-terminal or C-terminal residue to the 3' or 5' end of the antisense oligonucleotide.

Suitably, the carrier is coupled at its C-terminal residue to the 5' end of the antisense oligonucleotide.

Optionally, where the antisense oligonucleotide comprises phosphorus-containing intersubunit linkages, and the carrier is a peptide, the peptide may be conjugated to the antisense oligonucleotide via a covalent bond to the phosphorous of the terminal linkage group.

Alternatively, when the carrier is a peptide, and the antisense oligonucleotide is a morpholino, the peptide may be conjugated to the nitrogen atom of the 3' terminal morpholino group of the oligomer.

Optionally, the carrier may be conjugated to the antisense oligonucleotide via a linker moiety. Optionally, the linker moiety may comprise one or more of: an optionally substituted piperazinyl moiety, a beta alanine, glycine, proline, and/or a 6-aminohexanoic acid residue in any combination.

Alternatively, the carrier may be conjugated directly to the antisense oligonucleotide without a linker moiety.

Suitably the conjugate may further comprise a homing moiety.

Suitably, the homing moiety is selective for a selected mammalian tissue, i.e., the same tissue being targeted by the antisense oligonucleotide. Suitably, the homing moiety is selective for muscle tissue.

Suitably, the homing moiety is a homing peptide.

Suitable homing peptides are disclosed in 'Effective Dystrophin Restoration by a Novel Muscle-Homing Peptide—Morpholino Conjugate in Dystrophin-Deficient mdx Mice' Gao et Mol Ther. 2014 July; 22(7): 1333-1341, for example.

Suitably, the carrier peptide and the homing peptide may be formed as a chimeric fusion protein.

Suitably, the conjugate may comprise a chimeric peptide formed from a cell penetrating peptide and a muscle-specific homing peptide.

Optionally, the conjugate may be of the form: carrier peptide-homing peptide-antisense oligonucleotide or of the form: homing peptide-carrier peptide-antisense oligonucleotide. Suitably, the antisense oligonucleotide may be conjugated to a carrier that enhances the solubility of the antisense oligonucleotide. Suitably the solubility in an aqueous medium. Suitably, a carrier that enhances solubility may be conjugated to the antisense oligonucleotide in addition to a carrier operable to transport the antisense oligonucleotide. Suitably, the carrier that enhances solubility and the carrier that transports the antisense oligonucleotide may be formed as a chimeric fusion protein.

Suitable carriers that enhance the solubility of an antisense oligonucleotide are polymers, such as polyethylene glycol, or triethylene glycol.

Pharmaceutically Acceptable Excipient

The present invention further relates to a pharmaceutical composition comprising the antisense oligonucleotide of the invention or a conjugate thereof, further comprising one or more pharmaceutically acceptable excipients.

Suitably, the pharmaceutical composition is prepared in a manner known in the art (as described in Remingtons Pharmaceutical Sciences, Mack Publ. Co., Easton, Pa. (1985)), with pharmaceutically inert inorganic and/or organic excipients being used. The term 'pharmaceutically acceptable' refers to molecules and compositions that are physiologically tolerable and do not typically produce an allergic or similarly untoward reaction when administered to a patient.

Suitably, the pharmaceutical composition may be formulated as a pill, tablet, coated tablet, hard gelatin capsule, soft gelatin capsule and/or suppository, solution and/or syrup, injection solution, microcapsule, implant and/or rod, and the like.

In one embodiment, the pharmaceutical composition may be formulated as an injection solution.

Suitably, pharmaceutically acceptable excipients for preparing pills, tablets, coated tablets and hard gelatin capsules may be selected from any of: Lactose, corn starch and/or derivatives thereof, talc, stearic acid and/or its salts, etc.

Suitably, pharmaceutically acceptable excipients for preparing soft gelatin capsules and/or suppositories may be selected from fats, waxes, semisolid and liquid polyols, natural and/or hardened oils, etc.

Suitably, pharmaceutically acceptable excipients for preparing solutions and/or syrups may be selected from water, sucrose, invert sugar, glucose, polyols, etc.

Suitably, pharmaceutically acceptable excipients for preparing injection solutions may be selected from water, saline, alcohols, glycerol, polyols, vegetable oils, etc.

Suitably, pharmaceutically acceptable excipients for preparing microcapsules, implants and/or rods may be selected from mixed polymers such as glycolic acid and lactic acid or the like.

In addition, the pharmaceutical composition may comprise a liposome formulation which are described in N. Weiner, (Drug Develop Ind Pharm 15 (1989) 1523), "Liposome Dermatics" (Springer Verlag 1992) and Hayashi (Gene Therapy 3 (1996) 878).

Optionally, the pharmaceutical composition may comprise two or more different antisense oligonucleotides or conjugates thereof. Optionally, the pharmaceutical composition may further comprise one or more antisense oligonucleotides or conjugates thereof targeting different exons, suitably different exons of the human dystrophin pre-mRNA. Optionally, the one or more further antisense oligonucleotides or conjugates thereof may target exons adjacent to exon 51, for example, exon 50 or exon 52 of the human dystrophin pre-mRNA. Suitably, the one or more antisense oligonucleotides or conjugates thereof targeting different exons of the human dystrophin pre-mRNA are operable, together with the antisense oligonucleotide of the invention, to restore the reading frame of dystrophin mRNA.

Optionally, the pharmaceutical composition may further comprise one or more antisense oligonucleotides or conjugates thereof targeting different genes. For example, the one or more further antisense oligonucleotides or conjugates thereof may target myostatin. Such dual targeting is described in 'Dual exon skipping in myostatin and dystrophin for Duchenne muscular dystrophy' Kemaladewi et al. BMC Med Genomics. 2011 Apr. 20; 4:36.

Optionally, the one or more further antisense oligonucleotides may be joined together and/or joined to the antisense oligonucleotide of the first aspect.

Optionally, the antisense oligonucleotide and/or conjugate may be present in the pharmaceutical composition as a physiologically tolerated salt. Suitably, physiologically tolerated salts retain the desired biological activity of the antisense oligonucleotide and/or conjugate thereof and do not impart undesired toxicological effects. For antisense oligonucleotides, suitable examples of pharmaceutically acceptable salts include (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Optionally, the pharmaceutical composition may comprise, in addition to at least one antisense oligonucleotide and/or conjugate, one or more different therapeutically active ingredients. The one or more therapeutically active ingredients may be selected from, for example: corticosteroids, utrophin-upregulators, TGF-beta inhibitors, and myostatin inhibitors.

Suitably, in addition to the active ingredients and excipients, a pharmaceutical composition may also comprise additives, such as fillers, extenders, disintegrants, binders, lubricants, wetting agents, stabilizing agents, emulsifiers, preservatives, sweeteners, dyes, flavorings or aromatizing agents, thickeners, diluents or buffering substances, and, in addition, solvents and/or solubilizing agents and/or agents for achieving a slow release effect, and also salts for altering the osmotic pressure, coating agents and/or antioxidants. Suitable additives may include Tris-HCl, acetate, phosphate, Tween 80, Polysorbate 80, ascorbic acid, sodium metabisulfite, Thimersol, benzyl alcohol, lactose, mannitol, or the like.

Administration

The present invention relates to a therapeutic antisense oligonucleotide and to a pharmaceutical composition comprising the therapeutic antisense oligonucleotide which are for administration to a subject.

Suitably, the antisense oligonucleotide and/or pharmaceutical composition may be for topical, enteral or parenteral administration.

Suitably, the antisense oligonucleotide and/or pharmaceutical composition may be for administration orally, transdermally, intravenously, intrathecally, intramuscularly, subcutaneously, nasally, transmucosally or the like.

In one embodiment, the antisense oligonucleotide and/or pharmaceutical composition is for intramuscular administration.

In one embodiment, the antisense oligonucleotide and/or pharmaceutical composition is for intramuscular administration by injection.

An 'effective amount' or 'therapeutically effective amount' refers to an amount of the antisense oligonucleotide, administered to a subject, either as a single dose or as part of a Page 19 Header series of doses, which is effective to produce a desired physiological response or therapeutic effect in the subject.

Suitably, the desired physiological response includes increased expression of a relatively functional or biologically active form of the dystrophin protein, suitably in muscle tissues or cells that contain a defective dystrophin protein or no dystrophin.

Suitably, the desired therapeutic effects include improvements in the symptoms or pathology of a muscular disorder, reducing the progression of symptoms or pathology of a muscular disorder, and slowing the onset of symptoms or pathology of a muscular disorder. Examples of such symptoms include fatigue, mental retardation, muscle weakness, difficulty with motor skills (e.g., running, hopping, jumping), frequent falls, and difficulty walking.

Suitably, the antisense oligonucleotide or conjugate thereof are administered at a dose in the range from about 0.0001 to about 100 mg per kilogram of body weight per day.

Suitably, the antisense oligonucleotide or conjugate thereof are administered daily, once every 2, 3, 4, 5, 6, 7, 8, 9, 10, 11, 12, 13, 14 days, once every 1, 2, 3, 4, 5, 6, 7, 8, 9, 10, 11, 12 weeks, or once every 1, 2, 3, 4, 5, 6, 7, 8, 9, 10, 11, 12 months.

Suitably, the dose and frequency of administration may be decided by a physician, as needed, to maintain the desired expression of a functional dystrophin protein.

Suitably, the antisense oligonucleotide or conjugate thereof may be administered as two, three, four, five, six or more sub-doses separately at appropriate intervals throughout the day, optionally, in unit dosage forms.

Subject

The present invention also relates to treatment of a muscular disorder by administering a therapeutically effective amount of the antisense oligonucleotide or conjugate thereof to a subject in need thereof.

Suitably the subject has a muscular disorder, as defined above.

Suitably, the subject is mammalian. Suitably the subject is human.

Suitably the subject may be male or female. However, suitably the subject is male.

Suitably, the subject is any age. However, suitably the subject is between the ages of 1 month old to 50 years old, suitably between the ages of 1 years old and 30 years old, suitably between the ages of 2 years old to 27 years old, suitably between the ages of 4 years old to 25 years old Increased Exon Skipping and Dystrophin Expression The present invention relates to a therapeutic antisense oligonucleotide for use in the treatment of muscular disorder by inducing exon skipping in the human dystrophin pre-mRNA to restore functional dystrophin protein expression.

Suitably, a 'functional' dystrophin protein refers to a dystrophin protein having sufficient biological activity to reduce the progressive degradation of muscle tissue that is otherwise characteristic of muscular dystrophy when compared to the defective form of dystrophin protein that is present in subjects with a muscular disorder such as DMD.

Suitably, a functional dystrophin protein may have about 10%, 20%, 30%, 40%, 50%, 60%, 70%, 80%, 90%, or 100% of the in vitro or in vivo biological activity of wild-type dystrophin. Suitably, a functional dystrophin protein has at least 10% to 20% of the in vitro or in vivo biological activity of wild-type dystrophin.

Suitably, the activity of dystrophin in muscle cultures in vitro can be measured according to myotube size, myofibril organization, contractile activity, and spontaneous clustering of acetylcholine receptors (see, e.g., Brown et al., Journal of Cell Science. 112:209-216, 1999).

Animal models are also valuable resources for studying the pathogenesis of disease, and provide a means to test dystrophin-related activity. Two of the most widely used animal models for DMD research are the mdx mouse and the golden retriever muscular dystrophy (GRMD) dog, both of which are dystrophin negative (see, e.g., Collins & Morgan, Int J Exp Pathol 84: 165-172, 2003). These and other animal models can be used to measure the functional activity of various dystrophin proteins.

Suitably, 'exon skipping' refers to the process by which an entire exon, or a portion thereof, is removed from a given pre-processed RNA (pre-mRNA), and is thereby excluded from being present in the mature RNA that is translated into a protein.

Suitably, the portion of the protein that is otherwise encoded by the skipped exon is not present in the expressed form of the protein.

Suitably therefore, exon skipping creates a truncated, though still functional, form of the protein as defined above.

Suitably, the exon being skipped is an exon from the human dystrophin gene, which may contain a mutation or other alteration in its sequence that otherwise causes aberrant splicing.

Suitably, the exon being skipped is exon 51 of the dystrophin gene.

Suitably, the antisense oligonucleotide is operable to induce exon skipping in dystrophin pre-mRNA.

Suitably, the antisense oligonucleotide is operable to induce exon skipping of exon 51 in dystrophin pre-mRNA.

Suitably, the antisense oligonucleotide is operable to increase expression of a functional form of a dystrophin protein in muscle tissue, and is operable to increase muscle function in muscle tissue.

Suitably, the antisense oligonucleotide is operable to increase muscle function by at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% compared to muscle function in subjects with a muscular disorder such as DMD that have not received the antisense oligonucleotide.

Suitably, the antisense oligonucleotide is operable to increase the percentage of muscle fibres that express a functional dystrophin protein in about at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of muscle fibres compared to subjects with a muscular disorder such as DMD that have not received the antisense oligonucleotide.

Suitably, the antisense oligonucleotide is operable to induce expression of a functional form of a dystrophin protein to a level of at least 1, 2, 3, 4, 5, 6, 7, 8, 9, 10, 15, 20, 25, 30, 25, 40, 45, or 50% of the expression of dystrophin protein in wild type cells and/or subjects. Suitably, the antisense oligonucleotide is operable to induce expression of a functional form of a dystrophin protein to a level of at least 1, 2, 3, 4, 5, 6, 7, 8, 9, 10, 15, or 20% of the expression of dystrophin protein in wild type cells and/or subjects.

Suitably, the antisense oligonucleotide is operable to induce expression of a functional form of a dystrophin protein to a level of at least 10, 15, or 20% of the expression of dystrophin protein in wild type cells and/or subjects.

Suitably, the antisense oligonucleotide is operable to induce exon skipping in the dystrophin pre-mRNA to a level of at least 10%, 20%, 30%, 40%, 50%, 60%, 70%, 80%, 90%, or 100%.

Suitably, the antisense oligonucleotide is operable to induce exon skipping in the dystrophin pre-mRNA to a level of at least 60%, 70%, 80%, 90%, or 100%.

Suitably, the antisense oligonucleotide is operable to induce exon skipping in the dystrophin pre-mRNA to a level of between 60% to 80%.

An 'increased' or 'enhanced' amount may include an increase that is 1.1, 1.2, 1.5, 2, 2.5, 3, 4, 5, 6, 7, 8, 9, 10, 15, 20, 30, 40, 50 or more times the amount produced when no antisense oligonucleotide compound (the absence of an agent) or a control compound is administered under the same circumstances.

Suitably, an 'increased' or 'enhanced' amount is a statistically significant amount.

BRIEF DESCRIPTION OF THE DRAWINGS

Certain embodiments of the present invention will now be described with reference to the following figures and tables in which.

Figure 1:
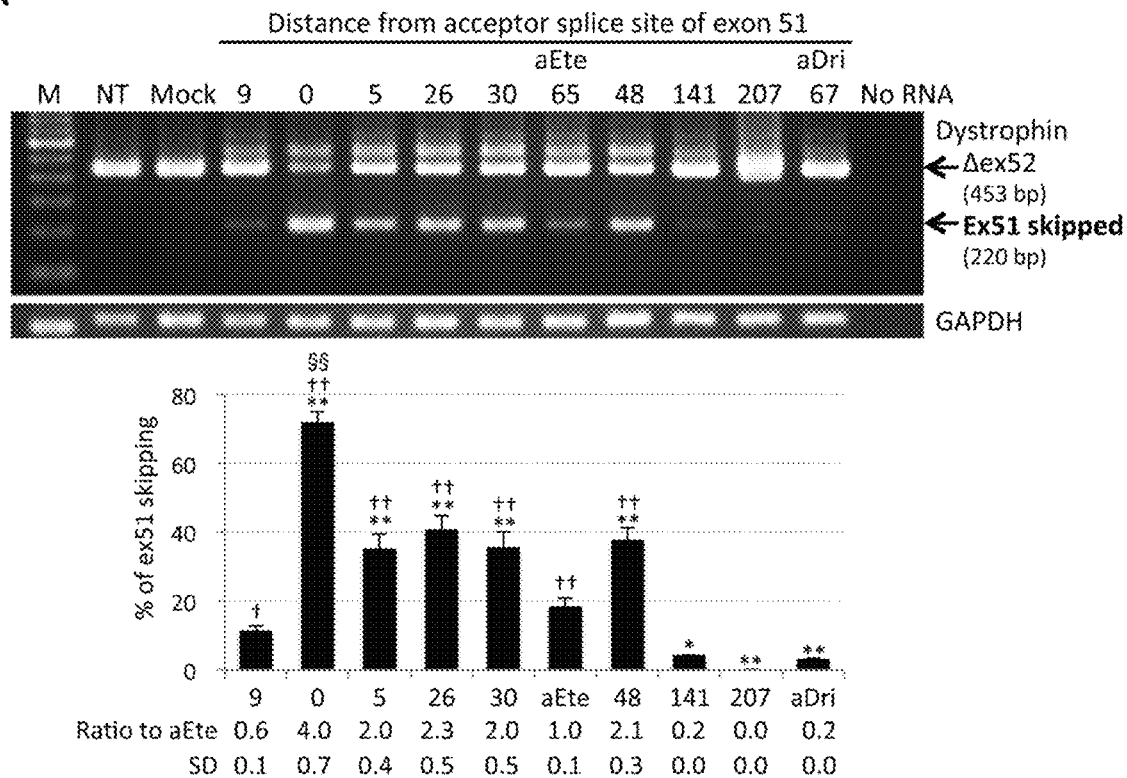
FIG. 1 Shows in vitro screening of antisense oligonucleotides (AOs) and analog AOs of eteplirsen (aEte) and drisapersen (aDri) at 10 µM, in immortalized clonal exon 52-deleted DMD skeletal muscle cells (KM571). Differentiated myotubes were harvested at day 5 following transfection (A) Efficiency of exon 51 skipping as measured by one-step RT-PCR. Representative images are shown. M, 100 bp marker; blank, no RNA template. (B) Efficiency in inducing truncated dystrophin protein as measured by quantitative Western blotting with the anti-dystrophin C-terminal antibody. Rescued dystrophin protein levels are calculated using calibration curves with healthy 8220 cells. Data represent mean±SD from 3-4 independent experiments. ** $p<0.01$ vs aEte, t $p<0.05$ and tt $p<0.01$ vs aDri, § § $p<0.01$ vs all of AOs in (A) and vs Ac0 in (B).
Figure 1:
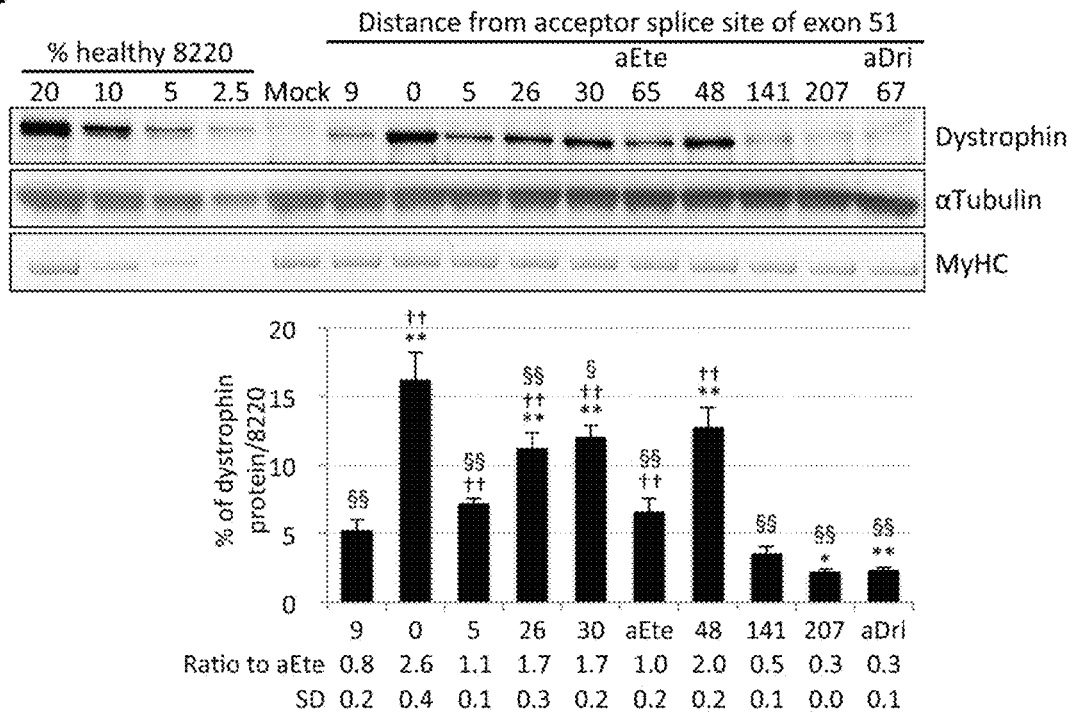

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or 27 process so disclosed, may be combined in any combination, except combinations where at least some of such features and/or steps are mutually exclusive.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The reader's attention is directed to all papers and documents which are filed concurrently with or previous to this specification in connection with this application and which are open to public inspection with this specification, and the contents of all such papers and documents are incorporated herein by reference.

EXAMPLES

Materials and Methods 1.1 Design and in Silico Screening of AOs.

413 30-mer and 25-mer AOs targeting exon 51 were designed and analysed using the AO predictive algorithm we recently developed (see Table 3). Table 3 shows in the columns from left to right; the exon number, the distance from acceptor splice site, the AO sequence (5' to 3'), the predicted skipping %, and the ranking within the screen. The left hand AOs are 30mers and the right hand AOs are 25-mers. Based on predicted exon skipping efficiencies, 8 AOs spaced at least 4 bases apart were selected for in vitro screening (Table 2). Target sequence specificities of selected AOs, eteplirsen, and drisapersen were analysed using The University of California, Santa Cruz Genome Browser (http://genome.ucsc.edu/index.html), confirming that the AO sequences theoretically do not bind any non-target RNA sequences with 100% identity.

1.2 Antisense Morpholinos.

All antisense sequences, including analog AOs of eteplirsen and drisapersen, were synthesized with the morpholino chemistry by Gene Tools (Philomath, Oreg.).

1.3 Cells.

Immortalized human skeletal muscle cells derived from three healthy subjects (IDs 8220, CHQ, and KM155) and two DMD patients harbouring deletion mutations of exon 52 (ID KM571) and exons 48-50 (ID 6594) in the DMD gene, respectively, were generated by transduction with human telomerase-expressing and cyclin-dependent kinase 4-expressing vectors in the Institute of Myology human cell immortalization platform, as previously described.33 The three immortalized healthy muscle cell lines were characterized and the clonal line 8220, which showed the highest dystrophin expression was selected as a positive control to prevent overestimation of rescued dystrophin expression in immortalized DMD cells. Primary skeletal muscle cells derived from DMD patients with deletion mutations of ex45-50 (ID 4546) and ex49-50 (ID 4555) and a healthy subject were prepared by the BioBank of Skeletal Muscle, Nerve Tissue, DNA and cell lines.

1.4 AO Transfection.

To mimic as closely as possible the in vivo effects of AO-mediated exon skipping therapy, mature, differentiated myotubes expressing sufficient levels of DMD mRNA were used for in vitro screening. Cells were cultured in proliferation conditions with growth medium (GM): DMEM/F12 with skeletal muscle supplement mix (Promocell, Heidelberg, Germany), 20% fetal bovine serum (Life Technologies, Waltham, Mass.), and antibiotics (50 units penicillin and 50 µg/ml streptomycin, Life Technologies, Waltham, Mass.). Immortalized and primary DMD skeletal muscle cells were seeded at 1.7×104/cm2 and 2.2×104/cm2, respectively, in collagen type I-coated 12 or 24-well culture plates. Two days after seeding, at approximately 80-90% confluence, GM was replaced with differentiation medium (DM): DMEM/F12 with 2% horse serum (GE Healthcare, Chicago, Ill.), lx ITS solution (Sigma, St. Louis, Mo.), and antibiotics. After three days in DM, cells were transfected with AO at 1, 3, 5 or 10 µM containing 6 µM of Endo-porter transfection reagent (Gene Tools, Philomath, Oreg.) (concentrated AOs at 1 mM were incubated at 65° C. for 10 min just before diluting with DM). Two days following AO transfection, AO-containing DM was replaced with regular DM. Cells were harvested at day 2, 5, or 11 after AO transfection (day 5, 8 or 14 following differentiation).

1.5 Mice.

Animal studies were approved by the Animal Care and Use Committee at the University of Alberta, Children's National Medical Center, and National Center of Neurology and Page 27 Header Psychiatry (NCNP). Male and female Dmd exon 52-deficient mdx5242 and wild-type mice (Jackson Laboratory, Bar Harbor, Me.) with a C57BL/6J background were prepared at age 4-8 weeks. Dmd mutation in affected mice was confirmed by genotyping with PCR. A transgenic mouse model harboring the human DMD gene and lacking the mouse Dmd gene (hDMD/Dmd-null mouse) was generated by cross-breeding male hDMD mice (Jackson Laboratory, Bar Harbor, Me.) with female Dmd-null mice.

1.6 Intramuscular Injection.

Mouse version morpholinos of Ac0, Ac48, eteplirsen or drisapersen at 5 or 20 µg in 40 µL saline were intramuscularly injected into tibialis anterior (TA) muscle under inhalation anesthesia with isoflurane as previously described.43 Fifty-µg of Ac0 morpholino and analog eteplirsen in 30 µL saline was injected into TA muscles of hDMD/Dmd-null mice. All muscle samples were harvested 2 weeks after intramuscular injection.

1.7 Exon Skipping Analysis by RT-PCR.

Total RNA was extracted with Trizol (Invitrogen, Waltham, Mass.) as previously described. RT-PCR to detect dystrophin mRNA was performed with the SuperScript III One-Step RT-PCR System (Invitrogen, Waltham, Mass.) and 0.2 µM of forward and reverse primers (see Table 1) for 200 ng and 320 ng of total RNA in immortalized and primary skeletal muscle cells, respectively. Primers were designed using Primer3Plus software and their specificity was confirmed in healthy human skeletal muscle cells (line 8220). The RT-PCR conditions were as follows: 50° C. for 5 minutes; 94° C. for 2 minutes; 35 cycles at 94° C. for 15 seconds, 60° C. for 30 seconds, and 68° C. for 35 seconds; and 68° C. for 5 minutes. PCR products were separated on a 1.5% agarose gel and visualized by SYBR Safe DNA Gel Stain (Invitrogen, Waltham, Mass.). Using ImageJ software (NIH) or the MCE-202 MultiNA system (Shimadzu, Kyoto, Japan), the efficiency of exon 51 skipping was calculated using the following formula:

$$\text{exon 51 - skipped transcript intensity}/(\text{native} + \text{intermediate} + \text{exon 51 - skipped transcript intensities}) \times 100(\%) \frac{Ex51 skipped transcript}{Native + Ex51 skipped transcript} \times d(\%)$$

Unknown top bands above the native band, possibly coming from unexpected splicing events, were excluded from quantification of skipping efficiency. The sequences of the PCR products were confirmed with Big Dye Terminator v3.1 (Applied Biosystems, Waltham, Mass.). GAPDH or 18S ribosomal RNA was used as an internal control.

TABLE 1

| Name | Sequence (5'→3') | Purpose |
| --- | --- | --- |
| Ex49/50_94-10_hDMD_Fwd SEQ ID NO. 16 | CAGCCAGTGAAGAGGAAGTTAG | Immortal KM571 DMD cells with ex52 del. |
| Ex53_80-99_hDMD_Rv SEQ ID NO.-17 | CCAGCCATTGTGTTGAATCC | Primary DMD and healthy cells hDMDIDmd-null mice |
| Ex47_60-79_hDMD_Fwd SEQ ID NO. 18 | AGGACCCGTGCTTGTAAGTG | Immortal 6594 DMD cells with ex48-50 del. |
| Ex52_83-105_hDMD_Rv SEQ ID NO. 19 | GATTGTTCTAGCCTCTTGATTGC | Primary 4555 DMD cells with ex49-50 del. |
| Ex43/44_167-12_hDMD_Fwd SEQ ID NO. 20 | GACAAGGGCGATTTGACAG | |
| Ex52_83-105_hDMD_Rv SEQ ID NO. 19 | GATTGTTCTAGCCTCTTGATTGC | Primary 4546 DMD cells with ex45-50 del. |
| Ex49/50_94-10_hDMD_Fwd SEQ ID NO. 16 | CAGCCAGTGAAGAGGAAGTTAG | Primary healthy cells |
| Ex52_83-105_hDMD_Rv SEQ ID NO. 19 | GATTGTTCTAGCCTCTTGATTGC | hDMD/Dmd-null mice |
| mDmd_ex49_83-102_Fwd SEQ ID NO. 21 | CAAGCACTCAGCCAGTGAAG | |
| deletion mDmd_ex53_81-100_Rv SEQ ID NO. 22 | TCCAGCCATTGTGTTGAATC | mdx52 mice with ex52 |

TABLE 1-continued

| Name | Sequence (5'→3') | Purpose |
|---|---|---|
| hGAPDH_662-81_Fwd SEQ ID NO. 23 | TCCCTGAGCTGAACGGGAAG | |
| control hGAPDH_860-79_Rv SEQ ID NO. 24 | GGAGGAGTGGGTGTCGCTGT | Internal |
| h18S_760-82_Fwd SEQ ID NO. 25 | TCGATGCTCTTAGCTGAGTGTCC | |
| control h18S_1039-58_Rv SEQ ID NO. 26 | TGATCGTCTTCGAACCTCCG | Internal |

1.8 Western Blotting

Cells were harvested with RIPA buffer (Thermo Scientific, Waltham, Mass.) containing cOmplete, Mini, EDTA-free protease inhibitor cocktail (Roche, Basel, Switzerland), and then homogenized by passing through a 21-gauge needle 10 times. The supernatants as loading samples were prepared by centrifugation at 14,000 g for 15 min at 4° C. Protein from muscle tissues were prepared as previously described. Protein concentrations were adjusted using the Bradford assay with supernatants diluted 100 times with distilled water. Proteins in a sample buffer containing 10% SDS, 70 mM Tris-HCl, pH 6.8, 5 mM EDTA, 20% glycerol, 0.004% bromophenol blue and 5% 2-mercaptoethanol were heated at 70° C. for 10 min. Western blotting was then done as previously described. 32,43,44 Twelve-µg and thirty-µg from cells and tissues, respectively, were used for sodium dodecyl sulfate-polyacrylamide gel electrophoresis. Blots were incubated with a rabbit polyclonal antibody against dystrophin C-terminal (1:2500, ab15278, Abcam, Cambridge, United Kingdom) in the blocking solution or DYS1 antibody against dystrophin rod domain (1:400, Leica Biosystems, Buffalo Grove, Ill.) for 1 hour at room temperature. The primary antibody was reacted with HRP-conjugated anti-rabbit or mouse IgG H+L antibody (1:10,000, Bio-Rad, Hercules, Calif.). Expression levels of dystrophin protein induced by AOs were quantified using calibration curves ($R^2$=0.93-0.99) from dystrophin protein of healthy 8220 skeletal muscle cells diluted with protein from non-treated DMD cells, or wild-type mouse using ImageJ (NIH). Alpha-tubulin was detected on the same membrane as a loading control. Myosin heavy chain (MyHC) on post-transferred gels was stained with Coomassie Brilliant Blue (Bio-Rad, Hercules, Calif.) as a loading control/differentiation marker.

1.9 Immunocytochemistry.

Cells were fixed with 4% paraformaldehyde for 5 min at room temperature. After washing with PBS containing 0.01% Triton X-100, cells were blocked with 10% goat serum (Life Technologies, Waltham, Mass.) in PBS with 0.05% Triton X-100 for 20 min and then incubated with anti-dystrophin C-terminal (ab15278) or rod-domain (DYS1) antibody at 1:50 dilution in blocking solution overnight at 4° C. Dystrophin signals were detected with Alexa 488- or 594-conjugated secondary antibody (1:500). Desmin (1:80, Abcam, Cambridge, United Kingdom) and MyHC-fast type (1:30, Leica Biosystems, Buffalo Grove, Ill.) were detected to confirm myogenic differentiation of cells. Cells were stored in SlowFade Gold Antifade Mountant with DAPI (Invitrogen, Waltham, Mass.) at 4° C. until analysed.

1.10 Immunohistochemistry.

Dystrophin-positive muscle fibers on cryosections from TA muscles of non-treated and treated mdx52 mice were detected with the ab15278 antibody as previously described. Signal intensity of dystrophin in the treated mice was compared with that in wild-type using neutral density filters (Eclipse TE 2000-U, Nikon, Tokyo, Japan).

1.11 Statistical Analysis.

For determining the significance of efficiencies in exon skipping and dystrophin protein rescue, data sets were prepared from at least three independent experiments in immortalized cells, triplicate wells in primary cells, and 3-7 mice. The statistical analysis between AO-treated groups was performed by one-way ANOVA followed by a post hoc Tukey-Kramer multiple comparison test. Simple linear regression analysis was performed for dose-responsiveness to AOs. Statistical significance was set at $p<0.05$ for all analyses.

2. Results 2.1 in Silico Screening of AOs for Exon 51 Skipping.

We designed total 413 AOs: 204 and 209 AOs with 30-mer and 25-mer lengths, respectively, which cover all possible target sites in DMD exon 51 (see Table 3). Our exon skipping efficiency algorithm (In Silico Screening Based on Predictive Algorithms as a Design Tool for Exon Skipping Oligonucleotides in Duchenne Muscular Dystrophy' Echigoya et al. PLOS ONE March 2015) predicted that the highest efficiency for exon 51 skipping was 80.5% for 30-mer AOs, and 41.2% for 25-mer AOs in the initial 5' site of exon 51. In silico screening indicated a very low exon skipping efficiency for the 30-base region targeted by eteplirsen (23.7%), which was ranked 92nd in all 413 AO candidates tested. It is noted that the drisapersen target site is completely encompassed by that of the 30-mer eteplirsen.

2.2 Characterization of Immortalized Clonal Healthy and DMD Skeletal Muscle Cell Lines.

Significant issues in preclinical testing with primary DMD muscle cells include low purity of muscle cells and insufficient amounts of mutant dystrophin mRNA, which present problems when trying to test AO efficacy. To overcome these hurdles, we generated immortalized clonal skeletal muscle cells from 3 healthy subjects and 2 DMD patients with exon 52 (ex52) and ex48-50 deletion (del.) mutations (IDs KM571 and 6594, respectively). All immortalized skeletal muscle cell lines tested expressed easily detectable dystrophin mRNA from day 3 Page 31 Header after induction of differentiation. To avoid overestimation of dystrophin protein levels induced by AOs in DMD cells, we selected a cell line (ID 8220) with the highest level of dystrophin protein among three immortalized healthy skeletal muscle cell lines as determined by Western blotting to serve as a positive control. Dystrophin protein expression in the 8220 cell line was also confirmed by immunocytochemistry.

2.3 In Vitro Screening of Exon 51 Skipping AOs.

Based on the in silico screening results, we selected eight 30-mer AOs, including both high-ranking and low-ranking sequences, spaced at least 4 bases apart from each other for in vitro screening (Table 2). In the present study, all tested AOs, including eteplirsen and drisapersen sequences, were synthesized using the morpholino chemistry that has been demonstrated to be well-tolerated in patients enrolled in clinical trials. Here, we termed control morpholino oligonucleotides having the same sequences as eteplirsen and drisapersen (produced by Gene Tools) as "analog eteplirsen" and "analog drisapersen". In RT-PCR, 5 of our morpholino AOs (Ac0, Ac5, Ac26, Ac30 and Ac48) at 10 μM showed significantly higher skipping efficiency compared to analog eteplirsen and drisapersen in immortalized DMD skeletal muscle cells harboring ex52 del. (FIG. 1A). Of the tested AOs, Ac0 in particular had the highest skipping efficiency, reaching up to 72%, which was 4 and 25 times more efficient than analogs of eteplirsen and drisapersen, respectively. In Western blotting, Ac0 also induced the highest levels of dystrophin protein, reaching up to 16% of levels in the healthy control cell line, followed by Ac48 at 13% (FIG. 1B). Interestingly, the two AOs, Ac0 and Ac48, with the highest skipping efficiency when tested were not those predicted to be the best from the algorithm.

TABLE 2

| Name | Oligo sequence (5' to 3') | Length (mer) | Distance from Ac | Predicted Skip % | Ranking |
|---|---|---|---|---|---|
| hEx51_Ac9 SEQ NO. 13 | CCACAGGTTGTGTCACCAGAGTAACAGTCT | 30 | 9 | 80.5 | 1 |
| hEx51_Ac0 SEQ ID No. 1 | GTGTCACCAGAGTAACAGTCTGAGTAGGAG | 30 | 0 | 80.1 | 2 |
| hEx51_Ac5 SEQ ID NO. 2 | AGGTTGTGTCACCAGAGTAACAGTCTGAGT | 30 | 5 | 73.0 | 4 |
| hEx51_Ac26 SEQ ID NO. 3 | GGCAGTTTCCTTAGTAACCACAGGTTGTGT | 30 | 26 | 66.3 | 12 |
| hEx51_Ac30 SEQ ID NO. 4 | AGATGGCAGTTTCCTTAGTAACCACAGGTT | 30 | 30 | 55.5 | 25 |
| Eteplirsen SEQ ID NO. 6 | CTCCAACATCAAGGAAGATGGCATTTC TAG | 30 | 65 | 23.7 | 67 |
| hEx51_Ac48 SEQ ID NO. 5 | ATGGCATTTCTAGTTTGGAGATGGCAGTTT | 30 | 48 | 10.6 | 128 |
| hEx51_Ac141 SEQ ID NO. 14 | TTATAACTTGATCAAGCAGAGAAAGCCAGT | 30 | 141 | 1.8 | 142 |
| hEx51_Ac207 SEQ ED NO. 15 | atacCTTCTGCTTGATGATCATCTCGTTGA | 30 | 207 | NA | NA |
| Drisapersen SEQ ID NO. 7 | TCAAGGAAGATGGCATTTCT | 20 | 67 | NA | NA |
| hEx51_Ac0-29mer SEQ ID NO. 8 | TGTCACCAGAGTAACAGTCTGAGTAGGAG | 29 | 0 | NA | NA |
| hEx51_Ac0-28mer SEQ ID NO. 9 | GTCACCAGAGTAACAGTCTGAGTAGGAG | 28 | 0 | NA | NA |
| hEx51_Ac0-27mer SEQ ID NO. 10 | TCACCAGAGTAACAGTCTGAGTAGGAG | 27 | 0 | NA | NA |
| hEx51_Ac0-26mer SEQ ID NO. 11 | CACCAGAGTAACAGTCTGAGTAGGAG | 26 | 0 | NA | NA |
| hEx51_Ac0-25mer SEQ ID NO. 12 | ACCAGAGTAACAGTCTGAGTAGGAG | 25 | 0 | 33.3 | 10a |

Ac, acceptor splice site.
Uncapitalized nucleotides indicate intronic sequence.
athe ranking in 25-mer AOs.

2.4 Time-Course Analysis with Ac0, Ac48, and Analog AOs of Eteplirsen and Drisapersen.

Figure 2:
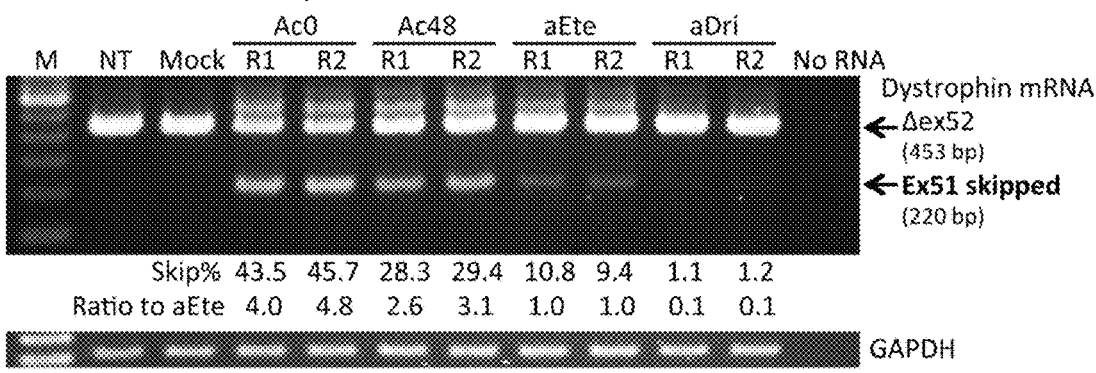
FIG. 2 Shows a time-course analysis of dystrophin exon 51 skipping and protein in an exon 52-deleted DMD-KM571 cell line transfected with Ac0, Ac48, and analog AOs of Page 23 Header eteplirsen and drisapersen at 5 µM. Samples were collected at days 2 and 11 post-transfection (A) RT-PCR analysis of exon 51 skipping. M, 100 bp marker; R, replicate number; blank, no RNA templates. (B) Quantification of induced dystrophin protein by Western blotting with the anti-dystrophin C-terminal antibody. Representative replicates from 3 independent experiments are shown.
Figure 2:
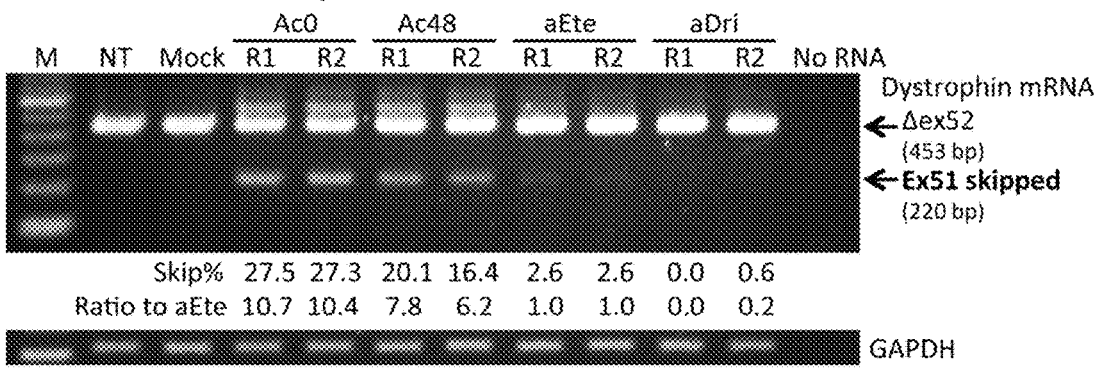
Figure 2:
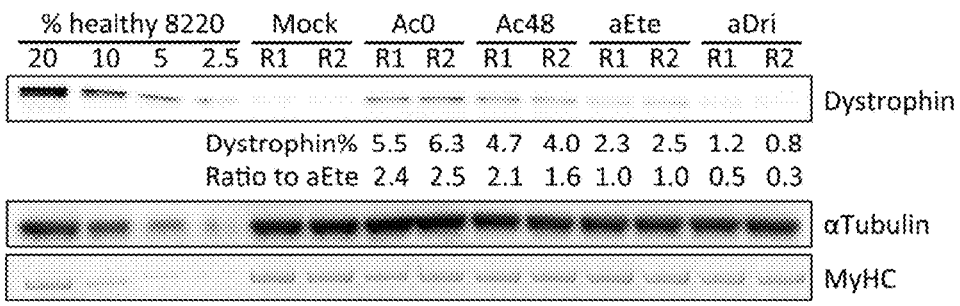
Figure 2:
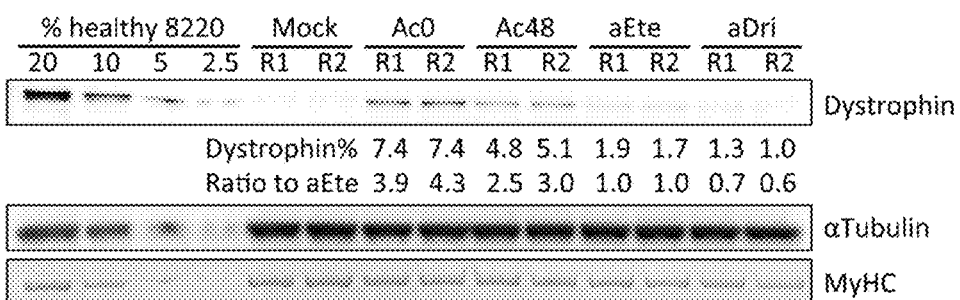

The persistent effects of Ac0, Ac48, and analogs of eteplirsen and drisapersen at 5 μM were examined in ex52 del. KM571 cells. The superiority of the oligonucleotides Ac0 and Ac48 of the present invention, with respect to exon skipping efficiency and dystrophin protein rescue, was observed at days 2 and 11 post-transfection compared to analog AOs of eteplirsen and drisapersen (FIG. 2).

2.5 Dose-Dependent Effects of Ac0, Ac48, and Analog Eteplirsen and Drisapersen.

Figure 3:
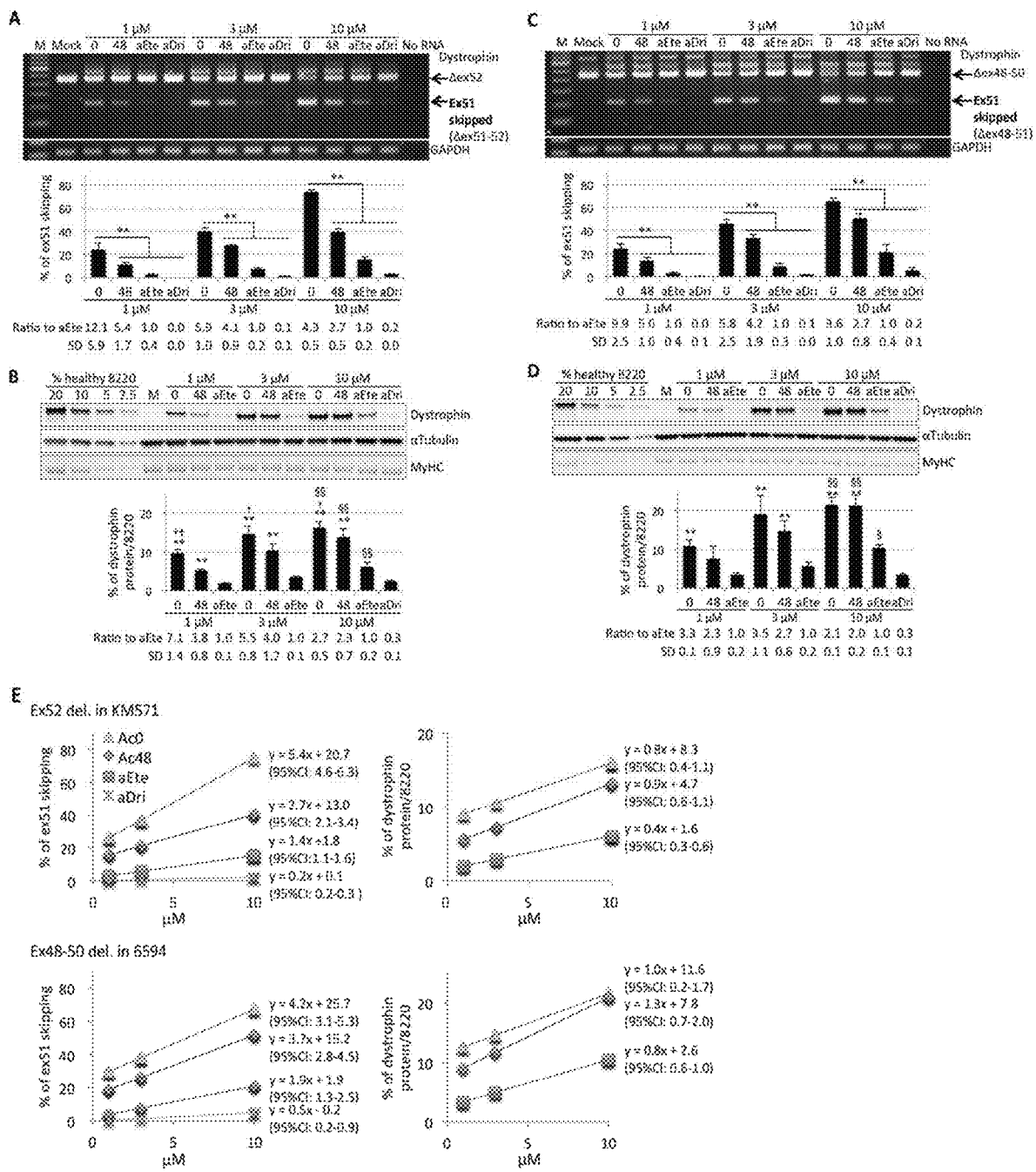
FIG. 3 Shows the dose-dependent effects of Ac0, Ac48, and analogs AOs of eteplirsen and drisapersen in immortalized DMD skeletal muscle cells as measured by one-step RT-PCR and quantitative Western blotting. DMD skeletal muscle cells were transfected with AOs at 1, 3, and 10 µM and harvested at day 5 post-transfection. (A) and (B) show exon 51 skipping efficiency and expression levels of rescued dystrophin protein, respectively, in DMD muscle cells with exon 52 deletion mutation (ID KM 571). Efficacy of skipping exon 51 and rescuing dystrophin protein expression is shown in (C) and (D), respectively, in DMD muscle cells harboring exons 48-50 deletion mutation (ID 6594). Data represent mean±SD from 3-7 independent experiments in the KM571 cell line and from 3-4 independent experiments in the 6594 cell line. * $p<0.05$, ** $p<0.01$ vs aEte; t $p<0.05$ and tt $p<0.01$ vs Ac48; § $p<0.05$, § § $p<0.01$ vs aDri in the same concentration, NS, no significance vs Ac0 at the next dose; ns, no significance vs Ac0 at 10 µM. (E) Dose-responsiveness to the AOs analysed by regression model. Statistical validity of regression equations in skipping and producing dystrophin protein was $p<0.008$ and $p<0.014$, respectively. Plots indicate values of exon skipping or dystrophin protein levels predicted in the regression analysis. The regression slope and 95% confidence interval (CI) are shown in individual AOs.

RT-PCR showed that Ac0 at the highest concentration of 10 μM induced up to 74% and 64% exon 51 skipping in DMD KM571 (ex52 del.) and 6594 cells (ex48-50 del.), respectively, which were significantly higher than analogs of eteplirsen and drisapersen (FIG. 3). At the lowest concentration (1 μM), Ac0 showed 12 and 10 times higher exon skipping efficiency compared to analog eteplirsen in KM571 and 6594 cells, respectively. Interestingly, even a concentration of 1 µM Ac0 induced higher levels of exon 51 skipping than 10 µM analog eteplirsen (24% efficiency vs 15% in KM571 and 24% efficiency vs 21% in 6594, respectively). Quantitative Western blotting revealed that 10 µM Ac0 rescued dystrophin protein expression in DMD cell lines up to 21% of healthy cell line levels (FIG. 3A to D). Even at 1 µM, the relative ratio of Ac0 to analog eteplirsen represented 7.1 and 3.3 times higher efficiency in producing dystrophin protein in KM571 and 6594 cell lines, respectively. Ac0 at 1 µM enabled the production of rescued dystrophin protein at higher or comparable levels than analog eteplirsen at 10 µM (10% vs 6% in KM571 and 11% vs 10% in 6594, respectively), confirming that Ac0 is more than 10-fold effective at producing Page 33 Header dystrophin protein compared to analog eteplirsen concentration-wise. Analog drisapersen did not work effectively for either of exon skipping or dystrophin production in the DMD muscle cell lines. The exon skipping response to Ac0 and Ac48 occurred in a dose-dependent manner that was greater than both analog eteplirsen, and analog drisapersen (FIGS. 3A and C). The dose-responsiveness of Ac0 with respect to dystrophin protein production was also higher than the control analogs in both DMD cell lines (FIG. 3E).

2.6 Immunocytochemical Assessment of Dystrophin Protein Rescue.

Figure 4:
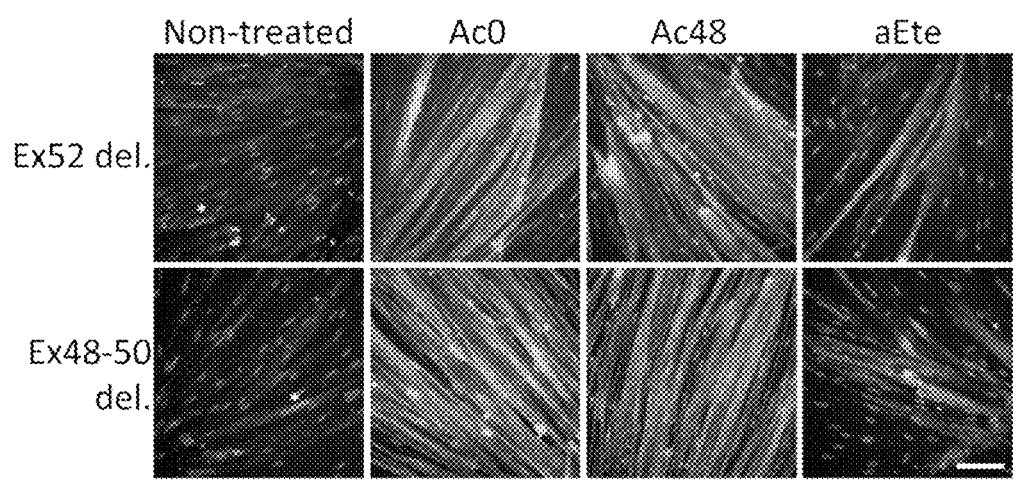
FIG. 4 Shows Immunocytochemistry in immortalized DMD patient-derived skeletal muscle cells with exon 52 (ID KM571) and exons 48-50 deletion mutations (ID 6594). Cells at day 5 post-transfection with 10 µM Ac0, Ac48, and analog eteplirsen (aEte) were stained with anti-dystrophin C-terminal antibody. Grey lines indicate dystrophin-positive myotubes. White dots indicate nuclei counter-stained with DAPI. * indicates representative false-positive myotubes due to their contraction or detachment from the culture plate. Representative images are shown from 3 independent experiments. Scale bar: 100 µm.

Immunocytochemistry revealed that Ac0 and Ac48 at 10 µM yielded more dystrophin-positive myotubes and displayed stronger signal intensity in DMD skeletal muscle cell lines harboring ex52 and ex48-50 del. mutations compared to analog eteplirsen (FIG. 4).

2.7 Length Optimization of Ac0 Morpholino.

Figure 5:
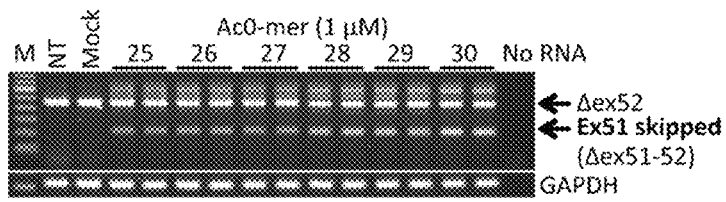
FIG. 5 Shows Length optimization of the Ac0 morpholino antisense oligonucleotide. Immortalized DMD muscle cells were transfected with Ac0 morpholinos composed of 25-, 26-, 27-, 28-, 29-, and 30-mer lengths. A representative image and quantification of exon 51 skipping induced by Ac0 morpholinos at 1 µM (A and B) and 3 µM (C and D) in DMD muscle cells with exon 52 deletion (KM571) are shown as represented by RT-PCR. (E-H) indicate the results in immortalized DMD cells with exons 48-50 deletion. The data are shown from 3 independent experiments.
Figure 5:
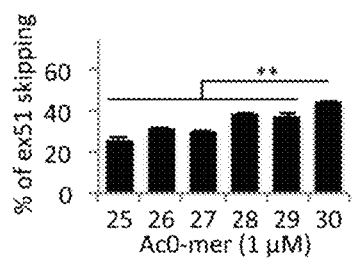
Figure 5:
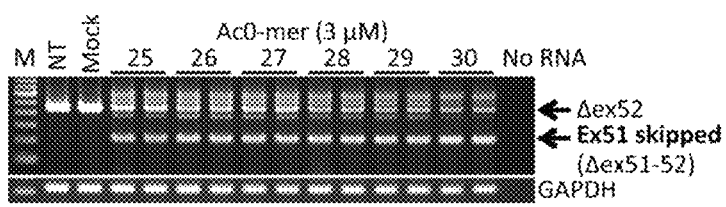
Figure 5:
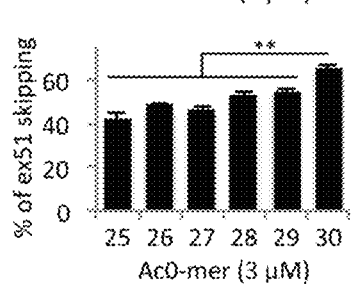
Figure 5:
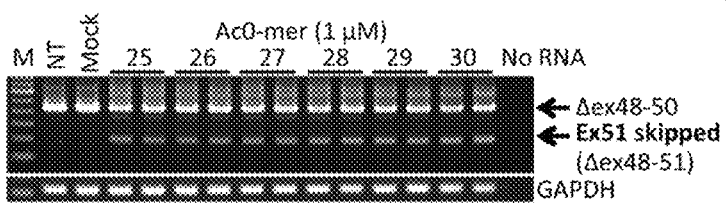
Figure 5:
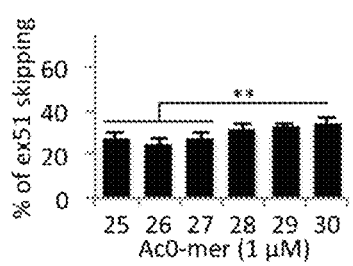
Figure 5:
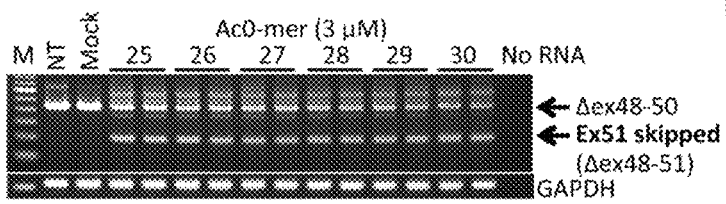
Figure 5:
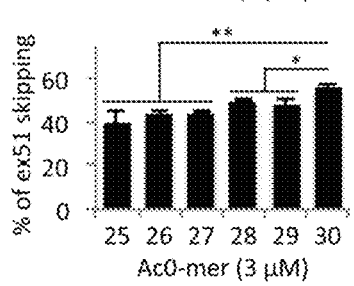

In silico and in vitro screening revealed that the initial 5' region of exon 51 between 0 and +89 is an important region for influencing exon 51 skipping. To optimize the sequence length of Ac0 targeting this region, we compared the skipping efficiencies of Ac0 morpholinos of different lengths (25- to 30-mer), in which nucleotides at the 5' site were systematically removed one at a time (see Table 2). In vitro testing in immortalized DMD muscle cells treated with 1 µM of these AOs showed that 25-30-mer Ac0 morpholinos produced efficient exon skipping (>20%) (FIG. 5), an effect that was not observed analog eteplirsen, and analog drisapersen at the same dose (FIG. 3). However, the efficiency of exon skipping increased as the length of the AO was increased. The statistically significant effectiveness of 30-mer Ac0 was confirmed at 1 and 3 µM doses compared to the shorter Ac0 morpholinos in both cell lines, even those AOs that are only 1 or 2 bases shorter.

2.8 Effect of Ac0, Ac48, and Analog Eteplirsen and Drisapersen on Primary DMD Patient-Derived Skeletal Muscle Cells.

Figure 6:
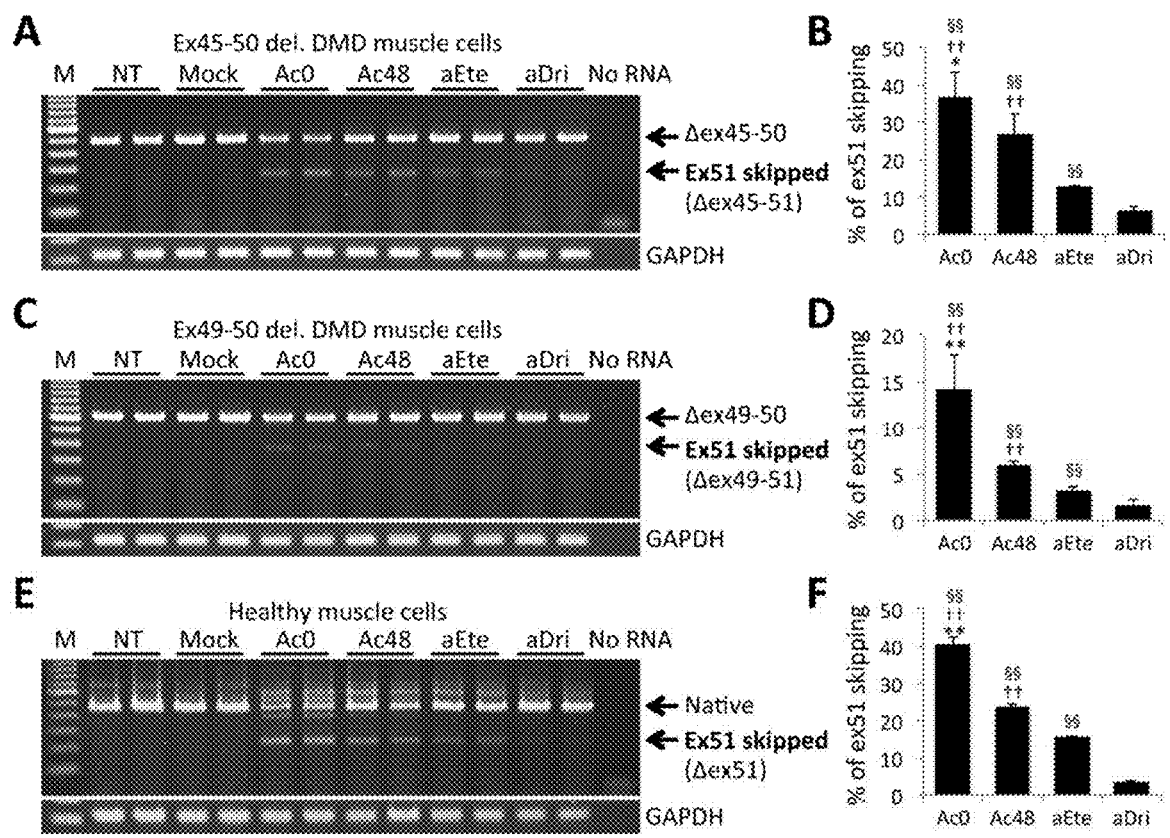
FIG. 6 shows Exon 51 skipping efficiency induced by Ac0, Ac48, analog AOs of eteplirsen (aEte) and drisapersen (aDri) in primary DMD and healthy skeletal muscle cells. Differentiated myotubes were transfected with Ac0, Ac48, and analog eteplirsen and drisapersen at 10 µM, and then harvested 3 days later. Exon 51 skipping efficiency as represented by one-step RT-PCR was shown in primary DMD cells with the deletion mutation of exons 45-50 (ID 4546) (A and B) or exons 49-50 (ID 4555) (C and D), and primary healthy muscle cells (E and F). Data represent mean±SD from at least triplicate wells in each condition. M, 100 bp marker. * $p<0.05$ and ** $p<0.01$ vs Ac48, tt $p<0.01$ vs aEte, § § $<0.01$ vs aDri.

We also tested the AOs in primary DMD skeletal muscle cells with exons 45-50 (ID 4546) or exons 49-50 del. mutations (ID 4555) to validate if the superior efficacy of 30-mer Ac0 is consistent for other muscle cell types and deletion mutation patterns. RT-PCR showed that Ac0 achieved significantly higher exon skipping efficiency in both primary DMD muscle cells compared to analog eteplirsen, or analog drisapersen (FIG. 6A to D): up to 5 and 7 times higher efficiency were observed compared to analog eteplirsen and drisapersen, respectively. A significant efficiency of Ac0-mediated exon 51 skipping was also confirmed Page 34 Header in primary healthy skeletal muscle cells (FIGS. 6E and F). Interestingly, with increasing exon 51 skipping efficiency, spontaneous exon 52 skipping, which does not disrupt the reading frame, was observed in primary healthy and DMD muscle cells, and an immortalized DMD muscle cell line with ex48-50 del. (6594).

2.10 In Vivo Efficacy of Ac0 Morpholino and Analog Eteplirsen in hDMD/Dmd-Null Mice.

Figure 7:
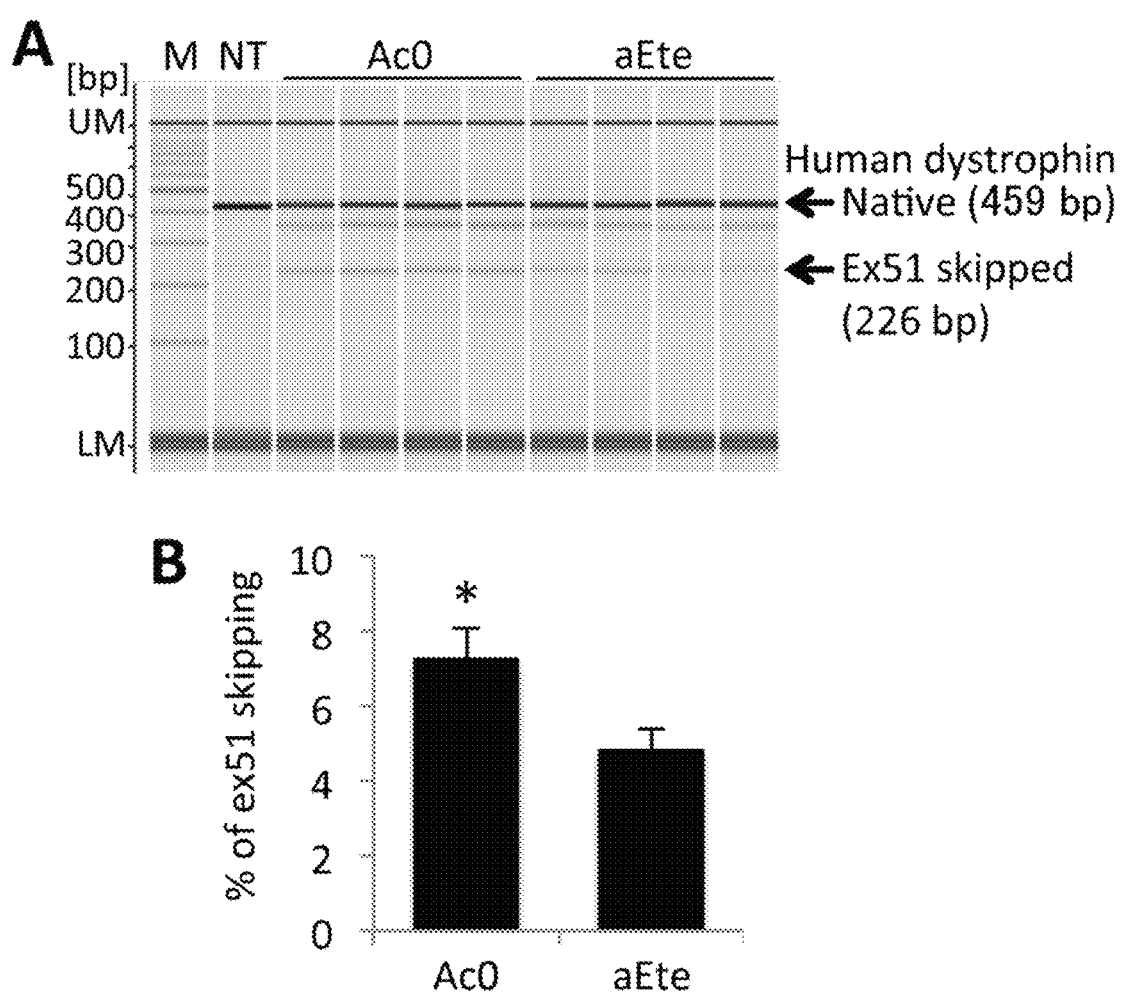
FIG. 7 shows In vivo efficacy of 30-mer Ac0 antisense morpholino oligonucleotide in the hDMD/Dmd-null mouse model. Exon skipping efficacy was analysed by RT-PCR with tibialis anterior muscles 2 weeks after the intramuscular injection of Ac0 morpholino or analog eteplirsen, aEte (50 µg in 30 µL saline). (A) Densitometry analysis of exon 51 skipping as represented by a microchip-based capillary electrophoresis system. (B) Averaged percentage of exon 51 skipping efficiency (mean±SE). N=7 in each group. M, marker; NT, non-treated muscle, UM, upper marker dye; LM, lower marker dye.
Figure 8:
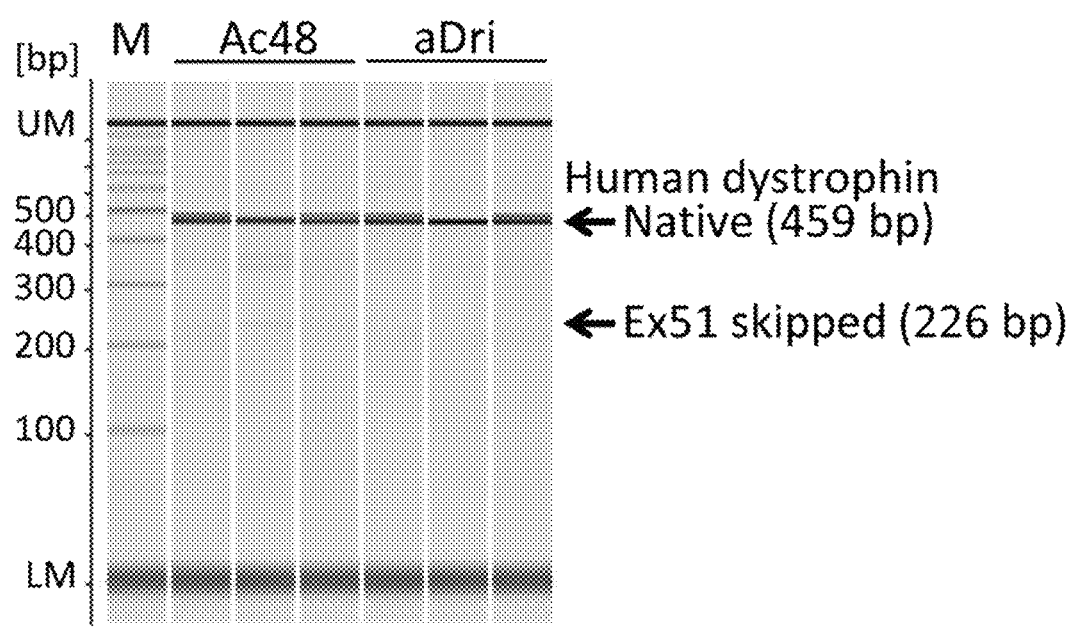
FIG. 8 shows In vivo efficacy of 30-mer Ac48 antisense morpholino oligonucleotide in the hDMD/Dmd-null mouse model. Exon skipping efficacy was analysed by RT-PCR with tibialis anterior muscles 2 weeks after the intramuscular injection of Ac48 morpholino or analog drisapersen aDri (50 µg in 30 µL saline). (A) Densitometry analysis of exon 51 skipping as represented by a microchip-based capillary electrophoresis system. (B) Averaged percentage of exon 51 skipping efficiency (mean±SE). N=7 in each group. M, marker; NT, non-treated muscle, UM, upper marker dye; LM, lower marker dye.

A major hurdle in the development of exon skipping therapy is that human-specific AOs cannot always be tested in an appropriate animal model. This limits the evaluation of in vivo effects of AOs designed for patients. Here, we developed a new mouse model that has the full-length human DMD gene but lacks the entire mouse Dmd gene (hDMD/Dmd-null) to test the in vivo efficacy of human AOs. This mouse model was employed to avoid the cross-reaction between human sequences and mouse sequences (note that conventional mdx mice still have the mouse dystrophin mRNA, which can cross-react with human-targeting AOs), and obtained by cross-breeding between hDMD mice34 and Dmd-null mice35. Ac0, Ac48, analog eteplirsen or analog drisapersen was injected into TA muscles of these mice, and the effectiveness of in vivo exon 51 skipping was analysed 2 weeks after the injection. The result showed significantly greater exon skipping efficiency in mice treated with Ac0 compared to analog eteplirsen (FIG. 7). Visible exon 51-skipped bands were found in Ac48-treated mice, with an average exon skipping efficiency of 1.11% (±0.46%, SE). On the other hand, no quantifiable exon 51-skipped bands were observed in mice treated with analog drisapersen (FIG. 8).

| SEQUENCES | |
|---|---|
| GTGTCACCAGAGTAACAGTCTGAGTAGGAG | Ac0 (SEQ ID NO. 1) |
| AGGTTGTGTCACCAGAGTAACAGTCTGAGT | Ac5 (SEQ ID NO. 2) |
| GGCAGTTTCCTTAGTAACCACAGGTTGTGT | Ac26 (SEQ ID NO. 3) |
| AGATGGCAGTTTCCTTAGTAACCACAGGTT | Ac30 (SEQ ID NO. 4) |
| ATGGCATTTCTAGTTTGGAGATGGCAGTTT | Ac48 (SEQ ID NO. 5) |
| CTCCAACATCAAGGAAGATGGCATTTCTAG | Eteplirsen (SEQ ID NO. 6) |
| TCAAGGAAGATGGCATTTCT | Drisapersen (SEQ ID NO. 7) |
| TGTCACCAGAGTAACAGTCTGAGTAGGAG | hEx51_Ac0-29mer (SEQ ID NO. 8) |
| GTCACCAGAGTAACAGTCTGAGTAGGAG | hEx51_Ac0-28mer (SEQ ID NO. 9) |
| TCACCAGAGTAACAGTCTGAGTAGGAG | hEx51_Ac0-27mer (SEQ ID NO. 10) |

| SEQUENCES | |
|---|---|
| CACCAGAGTAACAGTCTGAGTAGGAG | hEx51_Ac0-26mer (SEQ ID NO. 11) |
| ACCAGAGTAACAGTCTGAGTAGGAG | hEx51_Ac0-25mer (SEQ ID NO. 12) |
| CCACAGGTTGTGTCACCAGAGTAACAGTCT | Ac9 (SEQ ID NO. 13) |
| TTATAACTTGATCAAGCAGAGAAAGCCAGT | Ac141 (SEQ ID NO. 14) |
| atacCTTCTGCTTGATGATCATCTCGTTGA | Ac207 (SEQ ID NO. 15) |
| CAGCCAGTGAAGAGGAAGTTAG | Ex49/50_94-10_hDMD_Fwd (SEQ ID NO. 16) |
| CCAGCCATTGTGTTGAATCC | Ex53_80-99_hDMD_Rv (SEQ ID NO. 17) |
| AGGACCCGTGCTTGTAAGTG | Ex47_60-79_hDMD_Fwd (SEQ ID NO. 18) |
| GATTGTTCTAGCCTCTTGATTGC | Ex52_83-105_hDMD_Rv (SEQ ID NO. 19) |
| GACAAGGGCGATTTGACAG | Ex43/44_167-12_hDMD_Fwd (SEQ ID NO. 20) |
| CAAGCACTCAGCCAGTGAAG | mDmd_ex49_83-102_Fwd (SEQ ID NO 21) |
| TCCAGCCATTGTGTTGAATC | deletionmDmd_ex53_81-100_Rv (SEQ ID NO. 22) |
| TCCCTGAGCTGAACGGGAAG | hGAPDH_662-81_Fwd (SEQ ID NO. 23) |
| TCCAGCCATTGTGTTGAATC | controlhGAPDH_860-79_Rv (SEQ ID NO. 24) |
| TCGATGCTCTTAGCTGAGTGTCC | h18S_760-82_Fwd (SEQ ID NO. 25) |
| TGATCGTCTTCGAACCTCCG | control h18S_1039-58_Rv (SEQ ID NO. 26) |

TABLE 3

| | | | | | | | | | |
|---|---|---|---|---|---|---|---|---|---|
| 51 | 9 | CCACAGGTTGTGTCACCAGAGTAACAGTCT | 80.49 | 1 | 18 | GTAACCACAGGTTGTGTCACCAGAG | 41.20 | 1 |
| 51 | 0 | GTGTCACCAGAGTAACAGTCTGAGTAGGAG | 80.11 | 2 | 16 | AACCACAGGTTGTGTCACCAGAGTA | 39.94 | 2 |
| 51 | 10 | ACCACAGGTTGTGTCACCAGAGTAACAGTC | 79.98 | 3 | 12 | ACAGGTTGTGTCACCAGAGTAACAG | 38.08 | 3 |
| 51 | 5 | AGGTTGTGTCACCAGAGTAACAGTCTGAGT | 72.97 | 4 | 14 | CCACAGGTTGTGTCACCAGAGTAAC | 37.52 | 4 |
| 51 | 8 | CACAGGTTGTGTCACCAGAGTAACAGTCTG | 72.01 | 5 | 15 | ACCACAGGTTGTGTCACCAGAGTAA | 37.23 | 5 |
| 51 | 1 | TGTGTCACCAGAGTAACAGTCTGAGTAGGA | 71.94 | 6 | 31 | GGCAGTTTCCTTAGTAACCACAGGT | 37.18 | 6 |
| 51 | 2 | TTGTGTCACCAGAGTAACAGTCTGAGTAGG | 71.51 | 7 | 13 | CACAGGTTGTGTCACCAGAGTAACA | 36.66 | 7 |
| 51 | 11 | AACCACAGGTTGTGTCACCAGAGTAACAGT | 70.65 | 8 | 10 | AGGTTGTGTCACCAGAGTAACAGTC | 35.56 | 8 |
| 51 | 6 | CAGGTTGTGTCACCAGAGTAACAGTCTGAG | 68.18 | 9 | 11 | CAGGTTGTGTCACCAGAGTAACAGT | 33.75 | 9 |
| 51 | 7 | ACAGGTTGTGTCACCAGAGTAACAGTCTGA | 68.14 | 10 | 0 | ACCAGAGTAACAGTCTGAGTAGGAG | 33.34 | 10 |
| 51 | 4 | GGTTGTGTCACCAGAGTAACAGTCTGAGTA | 66.65 | 11 | 9 | GGTTGTGTCACCAGAGTAACAGTCT | 33.10 | 11 |
| 51 | 26 | GGCAGTTTCCTTAGTAACCACAGGTTGTGT | 66.32 | 12 | 17 | TAACCACAGGTTGTGTCACCAGAGT | 32.95 | 12 |
| 51 | 18 | CCTTAGTAACCACAGGTTGTGTCACCAGAG | 65.25 | 13 | 32 | TGGCAGTTTCCTTAGTAACCACAGG | 32.77 | 13 |
| 51 | 19 | TCCTTAGTAACCACAGGTTGTGTCACCAGA | 64.81 | 14 | 30 | GCAGTTTCCTTAGTAACCACAGGTT | 31.61 | 14 |
| 51 | 27 | TGGCAGTTTCCTTAGTAACCACAGGTTGTG | 64.09 | 15 | 19 | AGTAACCACAGGTTGTGTCACCAGA | 30.95 | 15 |
| 51 | 12 | TAACCACAGGTTGTGTCACCAGAGTAACAG | 64.08 | 16 | 23 | CCTTAGTAACCACAGGTTGTGTCAC | 30.66 | 16 |
| 51 | 13 | GTAACCACAGGTTGTGTCACCAGAGTAACA | 63.65 | 17 | 5 | GTGTCACCAGAGTAACAGTCTGAGT | 30.54 | 17 |
| 51 | 25 | GCAGTTTCCTTAGTAACCACAGGTTGTGTC | 61.81 | 18 | 1 | CACCAGAGTAACAGTCTGAGTAGGA | 30.26 | 18 |
| 51 | 29 | GATGGCAGTTTCCTTAGTAACCACAGGTTG | 61.44 | 19 | 6 | TGTGTCACCAGAGTAACAGTCTGAG | 29.52 | 19 |
| 51 | 14 | AGTAACCACAGGTTGTGTCACCAGAGTAAC | 57.56 | 20 | 24 | TCCTTAGTAACCACAGGTTGTGTCA | 28.97 | 20 |

TABLE 3-continued

| | | | | | | | | | |
|---|---|---|---|---|---|---|---|---|---|
| 51 | 23 | AGTTTCCTTAGTAACCACAGGTTGTGTCAC | 57.29 | 21 | 2 | TCACCAGAGTAACAGTCTGAGTAGG | 28.83 | 21 |
| 51 | 3 | GTTGTGTCACCAGAGTAACAGTCTGAGTAG | 56.65 | 22 | 3 | GTCACCAGAGTAACAGTCTGAGTAG | 26.60 | 22 |
| 51 | 17 | CTTAGTAACCACAGGTTGTGTCACCAGAGT | 56.39 | 23 | 25 | TTCCTTAGTAACCACAGGTTGTGTC | 26.23 | 23 |
| 51 | 24 | CAGTTTCCTTAGTAACCACAGGTTGTGTCA | 56.16 | 24 | 27 | GTTTCCTTAGTAACCACAGGTTGTG | 26.11 | 24 |
| 51 | 30 | AGATGGCAGTTTCCTTAGTAACCACAGGTT | 55.46 | 25 | 29 | CAGTTTCCTTAGTAACCACAGGTTG | 24.24 | 25 |
| 51 | 20 | TTCCTTAGTAACCACAGGTTGTGTCACCAG | 53.39 | 26 | 34 | GATGGCAGTTTCCTTAGTAACCACA | 22.08 | 26 |
| 51 | 16 | TTAGTAACCACAGGTTGTGTCACCAGAGTA | 53.04 | 27 | 8 | GTTGTGTCACCAGAGTAACAGTCTG | 21.25 | 27 |
| 51 | 15 | TAGTAACCACAGGTTGTGTCACCAGAGTAA | 52.28 | 28 | 7 | TTGTGTCACCAGAGTAACAGTCTGA | 21.05 | 28 |
| 51 | 22 | GTTTCCTTAGTAACCACAGGTTGTGTCACC | 51.90 | 29 | 4 | TGTCACCAGAGTAACAGTCTGAGTA | 20.02 | 29 |
| 51 | 28 | ATGGCAGTTTCCTTAGTAACCACAGGTTGT | 46.50 | 30 | 26 | TTTCCTTAGTAACCACAGGTTGTGT | 19.62 | 30 |
| 51 | 21 | TTTCCTTAGTAACCACAGGTTGTGTCACCA | 45.73 | 31 | 22 | CTTAGTAACCACAGGTTGTGTCACC | 18.61 | 31 |
| 51 | 31 | GAGATGGCAGTTTCCTTAGTAACCACAGGT | 43.71 | 32 | 33 | ATGGCAGTTTCCTTAGTAACCACAG | 18.23 | 32 |
| 51 | 32 | GGAGATGGCAGTTTCCTTAGTAACCACAGG | 38.58 | 33 | 108 | TCTGTCCAAGCCCGGTTGAAATCTG | 18.06 | 33 |
| 51 | 98 | CCAAGCCCGGTTGAAATCTGCCAGAGCAGG | 36.79 | 34 | 87 | TCTGCCAGAGCAGGTACCTCCAACA | 18.04 | 34 |
| 51 | 77 | CAGAGCAGGTACCTCCAACATCAAGGAAGA | 36.22 | 35 | 98 | CCCGGTTGAAATCTGCCAGAGCAGG | 17.52 | 35 |
| 51 | 46 | GGCATTTCTAGTTTGGAGATGGCAGTTTCC | 35.05 | 36 | 28 | AGTTTCCTTAGTAACCACAGGTTGT | 16.78 | 36 |
| 51 | 102 | CTGTCCAAGCCCGGTTGAAATCTGCCAGAG | 33.96 | 37 | 35 | AGATGGCAGTTTCCTTAGTAACCAC | 16.49 | 37 |
| 51 | 103 | TCTGTCCAAGCCCGGTTGAAATCTGCCAGA | 33.85 | 38 | 20 | TAGTAACCACAGGTTGTGTCACCAG | 16.42 | 38 |
| 51 | 78 | CCAGAGCAGGTACCTCCAACATCAAGGAAG | 32.83 | 39 | 83 | CCAGAGCAGGTACCTCCAACATCAA | 15.89 | 39 |
| 51 | 100 | GTCCAAGCCCGGTTGAAATCTGCCAGAGCA | 32.12 | 40 | 86 | CTGCCAGAGCAGGTACCTCCAACAT | 15.09 | 40 |
| 51 | 101 | TGTCCAAGCCCGGTTGAAATCTGCCAGAGC | 31.85 | 41 | 82 | CAGAGCAGGTACCTCCAACATCAAG | 14.95 | 41 |
| 51 | 53 | GGAAGATGGCATTTCTAGTTTGGAGATGGC | 31.58 | 42 | 84 | GCCAGAGCAGGTACCTCCAACATCA | 14.91 | 42 |
| 51 | 99 | TCCAAGCCCGGTTGAAATCTGCCAGAGCAG | 31.36 | 43 | 85 | TGCCAGAGCAGGTACCTCCAACATC | 14.66 | 43 |
| 51 | 106 | AGTTCTGTCCAAGCCCGGTTGAAATCTGCC | 31.20 | 44 | 110 | GTTCTGTCCAAGCCCGGTTGAAATC | 13.87 | 44 |
| 51 | 33 | TGGAGATGGCAGTTTCCTTAGTAACCACAG | 30.45 | 45 | 107 | CTGTCCAAGCCCGGTTGAAATCTGC | 12.76 | 45 |
| 51 | 105 | GTTCTGTCCAAGCCCGGTTGAAATCTGCCA | 29.76 | 46 | 109 | TTCTGTCCAAGCCCGGTTGAAATCT | 12.71 | 46 |
| 51 | 104 | TTCTGTCCAAGCCCGGTTGAAATCTGCCAG | 29.45 | 47 | 99 | GCCCGGTTGAAATCTGCCAGAGCAG | 12.07 | 47 |
| 51 | 117 | GCCAGTCGGTAAGTTCTGTCCAAGCCCGGT | 28.99 | 48 | 81 | AGAGCAGGTACCTCCAACATCAAGG | 11.09 | 48 |
| 51 | 87 | TGAAATCTGCCAGAGCAGGTACCTCCAACA | 27.92 | 49 | 36 | GAGATGGCAGTTTCCTTAGTAACCA | 10.96 | 49 |
| 51 | 37 | AGTTTGGAGATGGCAGTTTCCTTAGTAACC | 27.37 | 50 | 51 | GGCATTTCTAGTTTGGAGATGGCAG | 10.71 | 50 |
| 51 | 97 | CAAGCCCGGTTGAAATCTGCCAGAGCAGGT | 27.25 | 51 | 111 | AGTTCTGTCCAAGCCCGGTTGAAAT | 10.66 | 51 |
| 51 | 40 | TCTAGTTTGGAGATGGCAGTTTCCTTAGTA | 27.24 | 52 | 21 | TTAGTAACCACAGGTTGTGTCACCA | 10.43 | 52 |
| 51 | 76 | AGAGCAGGTACCTCCAACATCAAGGAAGAT | 27.06 | 53 | 106 | TGTCCAAGCCCGGTTGAAATCTGCC | 10.38 | 53 |
| 51 | 81 | CTGCCAGAGCAGGTACCTCCAACATCAAGG | 26.57 | 54 | 112 | AAGTTCTGTCCAAGCCCGGTTGAAA | 9.48 | 54 |
| 51 | 95 | AGCCCGGTTGAAATCTGCCAGAGCAGGTAC | 26.37 | 55 | 115 | GGTAAGTTCTGTCCAAGCCCGGTTG | 9.33 | 55 |
| 51 | 86 | GAAATCTGCCAGAGCAGGTACCTCCAACAT | 25.98 | 56 | 50 | GCATTTCTAGTTTGGAGATGGCAGT | 9.05 | 56 |
| 51 | 80 | TGCCAGAGCAGGTACCTCCAACATCAAGGA | 25.94 | 57 | 101 | AAGCCCGGTTGAAATCTGCCAGAGC | 8.92 | 57 |
| 51 | 96 | AAGCCCGGTTGAAATCTGCCAGAGCAGGTA | 25.55 | 58 | 103 | CCAAGCCCGGTTGAAATCTGCCAGA | 8.24 | 58 |
| 51 | 79 | GCCAGAGCAGGTACCTCCAACATCAAGGAA | 25.55 | 59 | 113 | TAAGTTCTGTCCAAGCCCGGTTGAA | 7.96 | 59 |
| 51 | 108 | TAAGTTCTGTCCAAGCCCGGTTGAAATCTG | 25.54 | 60 | 105 | GTCCAAGCCCGGTTGAAATCTGCCA | 7.95 | 60 |

TABLE 3-continued

| | | | | | | | |
|---|---|---|---|---|---|---|---|
| 51 | 90 | GGTTGAAATCTGCCAGAGCAGGTACCTCCA | 25.44 | 61 | 53 | ATGGCATTTCTAGTTTGGAGATGGC | 7.67 | 61 |
| 51 | 50 | AGATGGCATTTCTAGTTTGGAGATGGCAGT | 25.21 | 62 | 100 | AGCCCGGTTGAAATCTGCCAGAGCA | 7.33 | 62 |
| 51 | 89 | GTTGAAATCTGCCAGAGCAGGTACCTCCAA | 24.68 | 63 | 116 | CGGTAAGTTCTGTCCAAGCCCGGTT | 7.17 | 63 |
| 51 | 94 | GCCCGGTTGAAATCTGCCAGAGCAGGTACC | 23.96 | 64 | 97 | CCGGTTGAAATCTGCCAGAGCAGGT | 6.96 | 64 |
| 51 | 88 | TTGAAATCTGCCAGAGCAGGTACCTCCAAC | 23.90 | 65 | 117 | TCGGTAAGTTCTGTCCAAGCCCGGT | 6.90 | 65 |
| 51 | 34 | TTGGAGATGGCAGTTTCCTTAGTAACCACA | 23.77 | 66 | 102 | CAAGCCCGGTTGAAATCTGCCAGAG | 6.69 | 66 |
| 51 | 65 | CTCCAACATCAAGGAAGATGGCATTTCTAG | 23.66 | 67 | 114 | GTAAGTTCTGTCCAAGCCCGGTTGA | 6.65 | 67 |
| 51 | 35 | TTTGGAGATGGCAGTTTCCTTAGTAACCAC | 23.53 | 68 | 104 | TCCAAGCCCGGTTGAAATCTGCCAG | 6.63 | 68 |
| 51 | 91 | CGGTTGAAATCTGCCAGAGCAGGTACCTCC | 23.52 | 69 | 91 | GAAATCTGCCAGAGCAGGTACCTCC | 6.24 | 69 |
| 51 | 45 | GCATTTCTAGTTTGGAGATGGCAGTTTCCT | 23.40 | 70 | 37 | GGAGATGGCAGTTTCCTTAGTAACC | 6.17 | 70 |
| 51 | 57 | TCAAGGAAGATGGCATTTCTAGTTTGGAGA | 23.34 | 71 | 88 | ATCTGCCAGAGCAGGTACCTCCAAC | 6.14 | 71 |
| 51 | 118 | AGCCAGTCGGTAAGTTCTGTCCAAGCCCGG | 23.29 | 72 | 118 | GTCGGTAAGTTCTGTCCAAGCCCGG | 5.97 | 72 |
| 51 | 82 | TCTGCCAGAGCAGGTACCTCCAACATCAAG | 22.86 | 73 | 95 | GGTTGAAATCTGCCAGAGCAGGTAC | 5.25 | 73 |
| 51 | 93 | CCCGGTTGAAATCTGCCAGAGCAGGTACCT | 22.81 | 74 | 57 | GAAGATGGCATTTCTAGTTTGGAGA | 5.02 | 74 |
| 51 | 107 | AAGTTCTGTCCAAGCCCGGTTGAAATCTGC | 22.77 | 75 | 46 | TTCTAGTTTGGAGATGGCAGTTTCC | 5.00 | 75 |
| 51 | 116 | CCAGTCGGTAAGTTCTGTCCAAGCCCGGTT | 22.52 | 76 | 47 | TTTCTAGTTTGGAGATGGCAGTTTC | 4.87 | 76 |
| 51 | 109 | GTAAGTTCTGTCCAAGCCCGGTTGAAATCT | 22.51 | 77 | 89 | AATCTGCCAGAGCAGGTACCTCCAA | 4.60 | 77 |
| 51 | 110 | GGTAAGTTCTGTCCAAGCCCGGTTGAAATC | 22.46 | 78 | 58 | GGAAGATGGCATTTCTAGTTTGGAG | 4.30 | 78 |
| 51 | 92 | CCGGTTGAAATCTGCCAGAGCAGGTACCTC | 22.07 | 79 | 96 | CGGTTGAAATCTGCCAGAGCAGGTA | 3.79 | 79 |
| 51 | 36 | GTTTGGAGATGGCAGTTTCCTTAGTAACCA | 21.97 | 80 | 131 | GCAGAGAAAGCCAGTCGGTAAGTTC | 3.63 | 80 |
| 51 | 56 | CAAGGAAGATGGCATTTCTAGTTTGGAGAT | 21.85 | 81 | 80 | GAGCAGGTACCTCCAACATCAAGGA | 3.51 | 81 |
| 51 | 75 | GAGCAGGTACCTCCAACATCAAGGAAGATG | 21.81 | 82 | 120 | CAGTCGGTAAGTTCTGTCCAAGCCC | 3.35 | 82 |
| 51 | 39 | CTAGTTTGGAGATGGCAGTTTCCTTAGTAA | 21.62 | 83 | 128 | GAGAAAGCCAGTCGGTAAGTTCTGT | 3.12 | 83 |
| 51 | 64 | TCCAACATCAAGGAAGATGGCATTTCTAGT | 21.18 | 84 | 119 | AGTCGGTAAGTTCTGTCCAAGCCCG | 3.09 | 84 |
| 51 | 115 | CAGTCGGTAAGTTCTGTCCAAGCCCGGTTG | 20.90 | 85 | 92 | TGAAATCTGCCAGAGCAGGTACCTC | 2.10 | 85 |
| 51 | 52 | GAAGATGGCATTTCTAGTTTGGAGATGGCA | 20.77 | 86 | 40 | TTTGGAGATGGCAGTTTCCTTAGTA | 1.87 | 86 |
| 51 | 63 | CCAACATCAAGGAAGATGGCATTTCTAGTT | 20.61 | 87 | 90 | AAATCTGCCAGAGCAGGTACCTCCA | 1.74 | 87 |
| 51 | 111 | CGGTAAGTTCTGTCCAAGCCCGGTTGAAAT | 20.60 | 88 | 129 | AGAGAAAGCCAGTCGGTAAGTTCTG | 1.57 | 88 |
| 51 | 41 | TTCTAGTTTGGAGATGGCAGTTTCCTTAGT | 20.19 | 89 | 121 | CCAGTCGGTAAGTTCTGTCCAAGCC | 1.52 | 89 |
| 51 | 84 | AATCTGCCAGAGCAGGTACCTCCAACATCA | 19.86 | 90 | 122 | GCCAGTCGGTAAGTTCTGTCCAAGC | 0.99 | 90 |
| 51 | 113 | GTCGGTAAGTTCTGTCCAAGCCCGGTTGAA | 19.80 | 91 | 38 | TGGAGATGGCAGTTTCCTTAGTAAC | 0.44 | 91 |
| 51 | 114 | AGTCGGTAAGTTCTGTCCAAGCCCGGTTGA | 19.75 | 92 | 45 | TCTAGTTTGGAGATGGCAGTTTCCT | 0.40 | 92 |
| 51 | 73 | GCAGGTACCTCCAACATCAAGGAAGATGGC | 19.30 | 93 | 78 | GCAGGTACCTCCAACATCAAGGAAG | 0.10 | 93 |
| 51 | 38 | TAGTTTGGAGATGGCAGTTTCCTTAGTAAC | 19.21 | 94 | 48 | ATTTCTAGTTTGGAGATGGCAGTTT | -0.21 | 94 |
| 51 | 119 | AAGCCAGTCGGTAAGTTCTGTCCAAGCCCG | 19.04 | 95 | 125 | AAAGCCAGTCGGTAAGTTCTGTCCA | -0.23 | 95 |
| 51 | 67 | ACCTCCAACATCAAGGAAGATGGCATTTCT | 19.03 | 96 | 126 | GAAAGCCAGTCGGTAAGTTCTGTCC | -0.58 | 96 |
| 51 | 83 | ATCTGCCAGAGCAGGTACCTCCAACATCAA | 18.98 | 97 | 39 | TTGGAGATGGCAGTTTCCTTAGTAA | -0.64 | 97 |
| 51 | 58 | ATCAAGGAAGATGGCATTTCTAGTTTGGAG | 18.74 | 98 | 134 | CAAGCAGAGAAAGCCAGTCGGTAAG | -0.80 | 98 |
| 51 | 112 | TCGGTAAGTTCTGTCCAAGCCCGGTTGAAA | 18.59 | 99 | 132 | AGCAGAGAAAGCCAGTCGGTAAGTT | -0.92 | 99 |
| 51 | 54 | AGGAAGATGGCATTTCTAGTTTGGAGATGG | 18.20 | 100 | 137 | GATCAAGCAGAGAAAGCCAGTCGGT | -0.94 | 100 |

TABLE 3-continued

| 51 | 85 | AAATCTGCCAGAGCAGGTACCTCCAACATC | 17.93 | 101 | 133 | AAGCAGAGAAAGCCAGTCGGTAAGT | -1.00 | 101 |
|---|---|---|---|---|---|---|---|---|
| 51 | 66 | CCTCCAACATCAAGGAAGATGGCATTTCTA | 17.65 | 102 | 138 | TGATCAAGCAGAGAAAGCCAGTCGG | -1.03 | 102 |
| 51 | 49 | GATGGCATTTCTAGTTTGGAGATGGCAGTT | 17.50 | 103 | 127 | AGAAAGCCAGTCGGTAAGTTCTGTC | -1.07 | 103 |
| 51 | 42 | TTTCTAGTTTGGAGATGGCAGTTTCCTTAG | 17.40 | 104 | 136 | ATCAAGCAGAGAAAGCCAGTCGGTA | -1.36 | 104 |
| 51 | 44 | CATTTCTAGTTTGGAGATGGCAGTTTCCTT | 16.99 | 105 | 72 | ACCTCCAACATCAAGGAAGATGGCA | -1.50 | 105 |
| 51 | 51 | AAGATGGCATTTCTAGTTTGGAGATGGCAG | 16.77 | 106 | 79 | AGCAGGTACCTCCAACATCAAGGAA | -1.50 | 106 |
| 51 | 55 | AAGGAAGATGGCATTTCTAGTTTGGAGATG | 16.50 | 107 | 130 | CAGAGAAAGCCAGTCGGTAAGTTCT | -1.79 | 107 |
| 51 | 68 | TACCTCCAACATCAAGGAAGATGGCATTTC | 16.36 | 108 | 94 | GTTGAAATCTGCCAGAGCAGGTACC | -1.88 | 108 |
| 51 | 121 | GAAAGCCAGTCGGTAAGTTCTGTCCAAGCC | 16.27 | 109 | 59 | AGGAAGATGGCATTTCTAGTTTGGA | -2.14 | 109 |
| 51 | 120 | AAAGCCAGTCGGTAAGTTCTGTCCAAGCCC | 16.02 | 110 | 56 | AAGATGGCATTTCTAGTTTGGAGAT | -2.16 | 110 |
| 51 | 74 | AGCAGGTACCTCCAACATCAAGGAAGATGG | 15.45 | 111 | 93 | TTGAAATCTGCCAGAGCAGGTACCT | -2.19 | 111 |
| 51 | 122 | AGAAAGCCAGTCGGTAAGTTCTGTCCAAGC | 15.40 | 112 | 140 | CTTGATCAAGCAGAGAAAGCCAGTC | -2.58 | 112 |
| 51 | 59 | CATCAAGGAAGATGGCATTTCTAGTTTGGA | 15.35 | 113 | 70 | CTCCAACATCAAGGAAGATGGCATT | -2.88 | 113 |
| 51 | 123 | GAGAAAGCCAGTCGGTAAGTTCTGTCCAAG | 15.01 | 114 | 71 | CCTCCAACATCAAGGAAGATGGCAT | -2.97 | 114 |
| 51 | 69 | GTACCTCCAACATCAAGGAAGATGGCATTT | 14.79 | 115 | 52 | TGGCATTTCTAGTTTGGAGATGGCA | -3.00 | 115 |
| 51 | 60 | ACATCAAGGAAGATGGCATTTCTAGTTTGG | 14.56 | 116 | 63 | ATCAAGGAAGATGGCATTTCTAGTT | -3.06 | 116 |
| 51 | 72 | CAGGTACCTCCAACATCAAGGAAGATGGCA | 13.59 | 117 | 42 | AGTTTGGAGATGGCAGTTTCCTTAG | -3.16 | 117 |
| 51 | 124 | AGAGAAAGCCAGTCGGTAAGTTCTGTCCAA | 12.92 | 118 | 54 | GATGGCATTTCTAGTTTGGAGATGG | -3.16 | 118 |
| 51 | 70 | GGTACCTCCAACATCAAGGAAGATGGCATT | 12.45 | 119 | 49 | CATTTCTAGTTTGGAGATGGCAGTT | -3.37 | 119 |
| 51 | 71 | AGGTACCTCCAACATCAAGGAAGATGGCAT | 12.24 | 120 | 135 | TCAAGCAGAGAAAGCCAGTCGGTAA | -3.39 | 120 |
| 51 | 62 | CAACATCAAGGAAGATGGCATTTCTAGTTT | 12.18 | 121 | 123 | AGCCAGTCGGTAAGTTCTGTCCAAG | -3.44 | 121 |
| 51 | 61 | AACATCAAGGAAGATGGCATTTCTAGTTTG | 12.09 | 122 | 141 | ACTTGATCAAGCAGAGAAAGCCAGT | -3.99 | 122 |
| 51 | 126 | GCAGAGAAAGCCAGTCGGTAAGTTCTGTCC | 12.04 | 123 | 68 | CCAACATCAAGGAAGATGGCATTTC | -4.03 | 123 |
| 51 | 125 | CAGAGAAAGCCAGTCGGTAAGTTCTGTCCA | 11.49 | 124 | 124 | AAGCCAGTCGGTAAGTTCTGTCCAA | -4.20 | 124 |
| 51 | 43 | ATTTCTAGTTTGGAGATGGCAGTTTCCTTA | 11.13 | 125 | 60 | AAGGAAGATGGCATTTCTAGTTTGG | -4.22 | 125 |
| 51 | 47 | TGGCATTTCTAGTTTGGAGATGGCAGTTTC | 11.09 | 126 | 55 | AGATGGCATTTCTAGTTTGGAGATG | -4.42 | 126 |
| 51 | 129 | CAAGCAGAGAAAGCCAGTCGGTAAGTTCTG | 10.80 | 127 | 142 | AACTTGATCAAGCAGAGAAAGCCAG | -4.53 | 127 |
| 51 | 48 | ATGGCATTTCTAGTTTGGAGATGGCAGTTT | 10.61 | 128 | 73 | TACCTCCAACATCAAGGAAGATGGC | -4.70 | 128 |
| 51 | 130 | TCAAGCAGAGAAAGCCAGTCGGTAAGTTCT | 10.43 | 129 | 139 | TTGATCAAGCAGAGAAAGCCAGTCG | -4.97 | 129 |
| 51 | 128 | AAGCAGAGAAAGCCAGTCGGTAAGTTCTGT | 9.84 | 130 | 41 | GTTTGGAGATGGCAGTTTCCTTAGT | -5.02 | 130 |
| 51 | 131 | ATCAAGCAGAGAAAGCCAGTCGGTAAGTTC | 8.53 | 131 | 74 | GTACCTCCAACATCAAGGAAGATGG | -5.30 | 131 |
| 51 | 127 | AGCAGAGAAAGCCAGTCGGTAAGTTCTGTC | 8.26 | 132 | 64 | CATCAAGGAAGATGGCATTTCTAGT | -5.36 | 132 |
| 51 | 136 | ACTTGATCAAGCAGAGAAAGCCAGTCGGTA | 6.43 | 133 | 65 | ACATCAAGGAAGATGGCATTTCTAG | -5.43 | 133 |
| 51 | 137 | AACTTGATCAAGCAGAGAAAGCCAGTCGGT | 5.84 | 134 | 44 | CTAGTTTGGAGATGGCAGTTTCCTT | -6.16 | 134 |
| 51 | 138 | TAACTTGATCAAGCAGAGAAAGCCAGTCGG | 5.26 | 135 | 61 | CAAGGAAGATGGCATTTCTAGTTTG | -6.27 | 135 |
| 51 | 132 | GATCAAGCAGAGAAAGCCAGTCGGTAAGTT | 4.60 | 136 | 172 | GTCACCCACCATCACCCTCTGTGAT | -7.68 | 136 |
| 51 | 140 | TATAACTTGATCAAGCAGAGAAAGCCAGTC | 4.36 | 137 | 69 | TCCAACATCAAGGAAGATGGCATTT | -7.84 | 137 |
| 51 | 133 | TGATCAAGCAGAGAAAGCCAGTCGGTAAGT | 4.31 | 138 | 143 | TAACTTGATCAAGCAGAGAAAGCCA | -8.29 | 138 |
| 51 | 134 | TTGATCAAGCAGAGAAAGCCAGTCGGTAAG | 3.75 | 139 | 62 | TCAAGGAAGATGGCATTTCTAGTTT | -8.30 | 139 |
| 51 | 139 | ATAACTTGATCAAGCAGAGAAAGCCAGTCG | 2.70 | 140 | 77 | CAGGTACCTCCAACATCAAGGAAGA | -8.53 | 140 |

TABLE 3-continued

| | | | | | | | | |
|---|---|---|---|---|---|---|---|---|
| 51 | 135 | CTTGATCAAGCAGAGAAAGCCAGTCGGTAA | 2.28 | 141 | 67 | CAACATCAAGGAAGATGGCATTTCT | −8.81 | 141 |
| 51 | 141 | TTATAACTTGATCAAGCAGAGAAAGCCAGT | 1.76 | 142 | 173 | GGTCACCCACCATCACCCTCTGTGA | −8.87 | 142 |
| 51 | 142 | TTTATAACTTGATCAAGCAGAGAAAGCCAG | −0.17 | 143 | 144 | ATAACTTGATCAAGCAGAGAAAGCC | −8.98 | 143 |
| 51 | 146 | TGATTTTATAACTTGATCAAGCAGAGAAAG | −3.06 | 144 | 75 | GGTACCTCCAACATCAAGGAAGATG | −9.18 | 144 |
| 51 | 145 | GATTTTATAACTTGATCAAGCAGAGAAAGC | −3.17 | 145 | 174 | AGGTCACCCACCATCACCCTCTGTG | −9.52 | 145 |
| 51 | 156 | TCACCCTCTGTGATTTTATAACTTGATCAA | −3.49 | 146 | 66 | AACATCAAGGAAGATGGCATTTCTA | −9.58 | 146 |
| 51 | 167 | GTCACCCACCATCACCCTCTGTGATTTTAT | −3.97 | 147 | 43 | TAGTTTGGAGATGGCAGTTTCCTTA | −9.61 | 147 |
| 51 | 143 | TTTTATAACTTGATCAAGCAGAGAAAGCCA | −4.01 | 148 | 146 | TTATAACTTGATCAAGCAGAGAAAG | −9.74 | 148 |
| 51 | 174 | CCTCAAGGTCACCCACCATCACCCTCTGTG | −4.37 | 149 | 171 | TCACCCACCATCACCCTCTGTGATT | −10.00 | 149 |
| 51 | 144 | ATTTTATAACTTGATCAAGCAGAGAAAGCC | −4.66 | 150 | 170 | CACCCACCATCACCCTCTGTGATTT | −10.19 | 150 |
| 51 | 155 | CACCCTCTGTGATTTTATAACTTGATCAAG | −5.42 | 151 | 147 | TTTATAACTTGATCAAGCAGAGAAA | −10.27 | 151 |
| 51 | 168 | GGTCACCCACCATCACCCTCTGTGATTTTA | −5.53 | 152 | 176 | CAAGGTCACCCACCATCACCCTCTG | −11.06 | 152 |
| 51 | 175 | TCCTCAAGGTCACCCACCATCACCCTCTGT | −5.64 | 153 | 145 | TATAACTTGATCAAGCAGAGAAAGC | −11.20 | 153 |
| 51 | 157 | ATCCCTCTGTGATTTTATAACTTGATCA | −5.75 | 154 | 168 | CCCACCATCACCCTCTGTGATTTTA | −11.23 | 154 |
| 51 | 173 | CTCAAGGTCACCCACCATCACCCTCTGTGA | −6.14 | 155 | 169 | ACCCACCATCACCCTCTGTGATTTT | −11.29 | 155 |
| 51 | 176 | ATCCTCAAGGTCACCCACCATCACCCTCTG | −6.36 | 156 | 177 | TCAAGGTCACCCACCATCACCCTCT | −11.45 | 156 |
| 51 | 172 | TCAAGGTCACCCACCATCACCCTCTGTGAT | −6.44 | 157 | 181 | ATCCTCAAGGTCACCCACCATCACC | −11.50 | 157 |
| 51 | 166 | TCACCCACCATCACCCTCTGTGATTTTATA | −6.45 | 158 | 175 | AAGGTCACCCACCATCACCCTCTGT | −11.55 | 158 |
| 51 | 163 | CCCACCATCACCCTCTGTGATTTTATAACT | −6.75 | 159 | 180 | TCCTCAAGGTCACCCACCATCACCC | −11.59 | 159 |
| 51 | 161 | CACCATCACCCTCTGTGATTTTATAACTTG | −6.93 | 160 | 179 | CCTCAAGGTCACCCACCATCACCCT | −11.76 | 160 |
| 51 | 147 | GTGATTTTATAACTTGATCAAGCAGAGAAA | −7.04 | 161 | 183 | ATATCCTCAAGGTCACCCACCATCA | −11.76 | 161 |
| 51 | 164 | ACCCACCATCACCCTCTGTGATTTTATAAC | −7.04 | 162 | 178 | CTCAAGGTCACCCACCATCACCCTC | −11.79 | 162 |
| 51 | 171 | CAAGGTCACCCACCATCACCCTCTGTGATT | −7.07 | 163 | 76 | AGGTACCTCCAACATCAAGGAAGAT | −12.00 | 163 |
| 51 | 169 | AGGTCACCCACCATCACCCTCTGTGATTTT | −7.08 | 164 | 182 | TATCCTCAAGGTCACCCACCATCAC | −12.19 | 164 |
| 51 | 153 | CCCTCTGTGATTTTATAACTTGATCAAGCA | −7.09 | 165 | 156 | CTCTGTGATTTTATAACTTGATCAA | −12.23 | 165 |
| 51 | 165 | CACCCACCATCACCCTCTGTGATTTTATAA | −7.12 | 166 | 167 | CCACCATCACCCTCTGTGATTTTAT | −12.52 | 166 |
| 51 | 178 | ATATCCTCAAGGTCACCCACCATCACCCTC | −7.12 | 167 | 157 | CCTCTGTGATTTTATAACTTGATCA | −12.99 | 167 |
| 51 | 160 | ACCATCACCCTCTGTGATTTTATAACTTGA | −7.13 | 168 | 184 | GATATCCTCAAGGTCACCCACCATC | −13.02 | 168 |
| 51 | 177 | TATCCTCAAGGTCACCCACCATCACCCTCT | −7.18 | 169 | 148 | TTTTATAACTTGATCAAGCAGAGAA | −13.20 | 169 |
| 51 | 154 | ACCCTCTGTGATTTTATAACTTGATCAAGC | −7.53 | 170 | 190 | CTCGTTGATATCCTCAAGGTCACCC | −13.32 | 170 |
| 51 | 170 | AAGGTCACCCACCATCACCCTCTGTGATTT | −7.89 | 171 | 189 | TCGTTGATATCCTCAAGGTCACCCA | −13.68 | 171 |
| 51 | 162 | CCACCATCACCCTCTGTGATTTTATAACTT | −8.37 | 172 | 185 | TGATATCCTCAAGGTCACCCACCAT | −13.68 | 172 |
| 51 | 159 | CCATCACCCTCTGTGATTTTATAACTTGAT | −8.43 | 173 | 188 | CGTTGATATCCTCAAGGTCACCCAC | −13.80 | 173 |
| 51 | 158 | CATCACCCTCTGTGATTTTATAACTTGATC | −8.95 | 174 | 149 | ATTTTATAACTTGATCAAGCAGAGA | −13.86 | 174 |
| 51 | 179 | GATATCCTCAAGGTCACCCACCATCACCCT | −9.14 | 175 | 191 | TCTCGTTGATATCCTCAAGGTCACC | −13.88 | 175 |
| 51 | 152 | CCTCTGTGATTTTATAACTTGATCAAGCAG | −9.35 | 176 | 160 | CACCCTCTGTGATTTTATAACTTGA | −13.94 | 176 |
| 51 | 149 | CTGTGATTTTATAACTTGATCAAGCAGAGA | −9.51 | 177 | 187 | GTTGATATCCTCAAGGTCACCCACC | −14.07 | 177 |
| 51 | 180 | TGATATCCTCAAGGTCACCCACCATCACCC | −9.82 | 178 | 155 | TCTGTGATTTTATAACTTGATCAAG | −14.17 | 178 |
| 51 | 181 | TTGATATCCTCAAGGTCACCCACCATCACC | −9.89 | 179 | 158 | CCCTCTGTGATTTTATAACTTGATC | −14.23 | 179 |
| 51 | 148 | TGTGATTTTATAACTTGATCAAGCAGAGAA | −10.04 | 180 | 192 | ATCTCGTTGATATCCTCAAGGTCAC | −14.36 | 180 |

TABLE 3-continued

| | | | | | | | | |
|---|---|---|---|---|---|---|---|---|
| 51 | 182 | GTTGATATCCTCAAGGTCACCCACCATCAC | −10.09 | 181 | 186 | TTGATATCCTCAAGGTCACCCACCA | −14.42 | 181 |
| 51 | 183 | CGTTGATATCCTCAAGGTCACCCACCATCA | −10.50 | 182 | 193 | CATCTCGTTGATATCCTCAAGGTCA | −14.55 | 182 |
| 51 | 184 | TCGTTGATATCCTCAAGGTCACCCACCATC | −10.67 | 183 | 161 | TCACCCTCTGTGATTTTATAACTTG | −14.60 | 183 |
| 51 | 185 | CTCGTTGATATCCTCAAGGTCACCCACCAT | −10.79 | 184 | 166 | CACCATCACCCTCTGTGATITTATA | −14.64 | 184 |
| 51 | 186 | TCTCGTTGATATCCTCAAGGTCACCCACCA | −11.32 | 185 | 194 | TCATCTCGTTGATATCCTCAAGGTC | −14.75 | 185 |
| 51 | 188 | CATCTCGTTGATATCCTCAAGGTCACCCAC | −11.44 | 186 | 196 | GATCATCTCGTTGATATCCTCAAGG | −14.84 | 186 |
| 51 | 189 | TCATCTCGTTGATATCCTCAAGGTCACCCA | −11.81 | 187 | 150 | GATTTTATAACTTGATCAAGCAGAG | −14.89 | 187 |
| 51 | 187 | ATCTCGTTGATATCCTCAAGGTCACCCACC | −11.82 | 188 | 197 | TGATCATCTCGTTGATATCCTCAAG | −14.91 | 188 |
| 51 | 190 | ATCATCTCGTTGATATCCTCAAGGTCACCC | −12.10 | 189 | 199 | GATGATCATCTCGTTGATATCCTCA | −14.93 | 189 |
| 51 | 191 | GATCATCTCGTTGATATCCTCAAGGTCACC | −12.59 | 190 | 198 | ATGATCATCTCGTTGATATCCTCAA | −14.94 | 190 |
| 51 | 151 | CTCTGTGATTTTATAACTTGATCAAGCAGA | −12.71 | 191 | 200 | TGATGATCATCTCGTTGATATCCTC | −14.98 | 191 |
| 51 | 192 | TGATCATCTCGTTGATATCCTCAAGGTCAC | −13.26 | 192 | 201 | TTGATGATCATCTCGTTGATATCCT | −15.00 | 192 |
| 51 | 150 | TCTGTGATTTTATAACTTGATCAAGCAGAG | −13.47 | 193 | 195 | ATCATCTCGTTGATATCCTCAAGGT | −15.11 | 193 |
| 51 | 193 | ATGATCATCTCGTTGATATCCTCAAGGTCA | −13.85 | 194 | 202 | CTTGATGATCATCTCGTTGATATCC | −15.16 | 194 |
| 51 | 194 | GATGATCATCTCGTTGATATCCTCAAGGTC | −13.95 | 195 | 159 | ACCCTCTGTGATTTTATAACTTGAT | −15.57 | 195 |
| 51 | 195 | TGATGATCATCTCGTTGATATCCTCAAGGT | −14.35 | 196 | 204 | TGCTTGATGATCATCrCGTTGATAT | −15.61 | 196 |
| 51 | 196 | TTGATGATCATCTCGTTGATATCCTCAAGG | −14.51 | 197 | 203 | GCTTGATGATCATCTCGTTGATATC | −15.64 | 197 |
| 51 | 198 | GCTTGATGATCATCTCGTTGATATCCTCAA | −14.58 | 198 | 164 | CCATCACCCrCTGTGATTTTATAAC | −15.79 | 198 |
| 51 | 197 | CTTGATGATCATCTCGTTGATATCCTCAAG | −14.70 | 199 | 205 | CTGCTTGATGATCATCTCGTTGATA | −16.24 | 199 |
| 51 | 199 | TGCTTGATGATCATCTCGTTGATATCCTCA | −14.77 | 200 | 165 | ACCATCACCCTCTGTGATTTTATAA | −16.41 | 200 |
| 51 | 200 | CTGCTTGATGATCATCTCGTTGATATCCTC | −15.02 | 201 | 163 | CATCACCCTCTGTGATTTTATAACT | −16.49 | 201 |
| 51 | 201 | TCTGCTTGATGATCATCTCGTTGATATCCT | −15.29 | 202 | 206 | TCTGCTTGATGATCATCTCGTTGAT | −16.57 | 202 |
| 51 | 202 | TTCTGCTTGATGATCATCTCGTTGATATCC | −15.67 | 203 | 207 | TTCTGCTTGATGATCATCTCGTTGA | −16.92 | 203 |
| 51 | 203 | CTTCTGCTTGATGATCATCTCGTTGATATC | −16.24 | 204 | 208 | CTTCTGCTTGATGATCATCTCGTTG | −17.32 | 204 |
| 51 | | | | | 154 | CTGTGATTTTATAACTTGATCAAGC | −17.42 | 205 |
| 51 | | | | | 162 | ATCACCCTCTGTGATTTTATAACTT | −17.53 | 206 |
| 51 | | | | | 152 | GTGATTTTATAACTTGATCAAGCAG | −17.91 | 207 |
| 51 | | | | | 151 | TGATTTTATAACTTGATCAAGCAGA | −17.98 | 208 |
| 51 | | | | | 153 | TGTGATTTTATAACTTGATCAAGCA | −19.57 | 209 |

What is claimed is:

1. A modified synthetic antisense oligonucleotide analogue consisting of SEQ ID NO:1 (Ac0), SEQ ID NO:2 (Ac5), SEQ ID NO:3 (Ac26), SEQ ID NO:4 (Ac30), or SEQ ID NO:5 (Ac48).

2. The modified synthetic antisense oligonucleotide analogue of claim 1, wherein the modified synthetic antisense oligonucleotide analogue is selected from a peptide nucleic acid (PNA), a morpholino oligonucleotide, a phosphorothioate oligonucleotide, a phosphorodithioate oligonucleotide, an alkylphosphonate oligonucleotide, an acylphosphonate oligonucleotide, and a phosphoramidite oligonucleotide.

3. A conjugate comprising the modified synthetic antisense oligonucleotide analogue of claim 1 and a carrier, wherein the carrier is conjugated to the antisense oligonucleotide analogue.

4. The conjugate of claim 3, wherein the carrier is operable to transport the modified synthetic antisense oligonucleotide analogue into a target cell.

5. The conjugate of claim 3, wherein the carrier is selected from a peptide, a small molecule chemical, a polymer, a nanoparticle, a lipid, a liposome, and an exosome.

6. The conjugate of claim 3, wherein the carrier is a cell penetrating peptide.

7. The conjugate of claim 3, wherein the carrier is an arginine-rich cell penetrating peptide.

8. A method of treating a muscular disorder in a subject in need thereof, the method comprising administering the modified synthetic antisense oligonucleotide analogue of claim 1 to said subject.

9. The method of claim 8, wherein the muscular disorder is a disorder associated with a genetic mutation in a gene associated with muscle function.

10. The method of claim 8, wherein the muscular disorder is Duchenne muscular dystrophy or Becker muscular dystrophy.

* * * * *